(12) United States Patent
Kim et al.

(10) Patent No.: US 7,642,269 B2
(45) Date of Patent: Jan. 5, 2010

(54) PYRROLO[3,2-B]PYRIDINE DERIVATIVES AND PROCESSES FOR THE PREPARATION THEREOF

(75) Inventors: Jae-Gyu Kim, Seoul (KR); Byung-Nak Ahn, Seoul (KR); Hyouk-Woo Lee, Yongin (KR); Suk-Won Yoon, Seoul (KR); Young-Ae Yoon, Seoul (KR); Choong-Hyun Lee, Anyang (KR); Myung-Hun Cha, Anyang (KR); Heui-Il Kang, Gunpo (KR); Sun-Young Jang, Suwon (KR)

(73) Assignee: Yuhan Corporation, Seoul (KR)

( * ) Notice: Subject to any disclaimer, the term of this patent is extended or adjusted under 35 U.S.C. 154(b) by 127 days.

(21) Appl. No.: 11/574,398

(22) PCT Filed: Sep. 3, 2005

(86) PCT No.: PCT/KR2005/002926

§ 371 (c)(1),
(2), (4) Date: Feb. 27, 2007

(87) PCT Pub. No.: WO2006/038773

PCT Pub. Date: Apr. 13, 2006

(65) Prior Publication Data

US 2007/0213358 A1    Sep. 13, 2007

(30) Foreign Application Priority Data

Sep. 3, 2005 (KR) ...................... 10-2004-0070535

(51) Int. Cl.
*A61K 31/4745* (2006.01)
*C07D 471/02* (2006.01)

(52) U.S. Cl. ...................................... 514/300; 546/113
(58) Field of Classification Search ................. 546/113; 514/300
See application file for complete search history.

(56) References Cited

U.S. PATENT DOCUMENTS

| 4,450,164 | A | 5/1984 | Bristol et al. |
| 5,714,495 | A | 2/1998 | Viaud et al. |
| 6,476,034 | B2 * | 11/2002 | Wang et al. ............ 514/253.04 |
| 2003/0069266 | A1 | 4/2003 | Wang et al. |
| 2007/0287726 | A1 * | 12/2007 | Palmer ...................... 514/300 |

FOREIGN PATENT DOCUMENTS

| EP | 775120 | 2/1996 |
| EP | 1186607 | 3/2002 |
| EP | 1254907 | 11/2002 |
| WO | 9414795 | 7/1994 |
| WO | WO 9837080 | 8/1998 |
| WO | WO 9928322 | 6/1999 |
| WO | 0017200 | 3/2000 |
| WO | 2006013195 | 2/2006 |

OTHER PUBLICATIONS

Al-Mousawi, S.M., et al., "Studies with Condensed Azines: New Routes to Pyrazolo[3,4-b]pyridines and Pyrrolo[3,2-b]pyridines," J. Chem. Research, 1997, pp. 318-319.

Birnberg, G.H., et al., "The Synthesis of 5-Arylpyrrolo[3,2-b]pyridines and 7-Aryl-pyrrolo[3,2-b]pyridines: Addition of 3-Aminopyrroles to Aryl Enaminones," J. of Heterocyclic Chemistry, 1995, 32(4), pp. 1293-1298.

Pope, A.J., et al., "Reversible inhibitors of the gastric H+/K+-tranporting ATPase: a new class of anti-secretary agent," Trends in Pharm. Sci., 14:9, Sept. 1, 1993, 323-325.

* cited by examiner

*Primary Examiner*—Janet L Andres
*Assistant Examiner*—Niloofar Rahmani
(74) *Attorney, Agent, or Firm*—Sughrue Mion, PLLC

(57) ABSTRACT

The present invention provides novel pyrrolo[3,2-b]pyridine derivatives or pharmaceutically acceptable salts thereof, processes for the preparation thereof, and compositions comprising the same. The pyrrolo[3,2-b]pyridine derivatives or pharmaceutically acceptable salts thereof of the present invention have excellent proton pump inhibition effects and possess the ability to attain a reversible proton pump inhibitory effect.

5 Claims, No Drawings

PYRROLO[3,2-B]PYRIDINE DERIVATIVES AND PROCESSES FOR THE PREPARATION THEREOF

TECHNICAL FIELD

The present invention relates to novel pyrrolo[3,2-b]pyridine derivatives or pharmaceutically acceptable salts thereof which have an excellent inhibitory activity against gastric acid secretion, processes for the preparation thereof, and pharmaceutical compositions comprising the same.

BACKGROUND ART

Peptic ulcer disease occurs when offensive factors involving gastric acid secretion are strong or defensive factors of gastric mucous are weak. For the treatment of peptic ulcer disease, various drugs such as antacid, anticholinergic agent, $H_2$-receptor antagonist, and proton pump inhibitor have been used. The advent of omeprazole as a proton pump inhibitor has rekindled research activities in this field.

However, it has been pointed out that proton pump inhibition by omeprazole is irreversible, thereby incurring long-term inhibition of gastric acid secretion, which may induce side effects. Accordingly, various attempts to develop a reversible proton pump inhibitor are being made. For example, imidazopyridine derivatives are disclosed in WO 98/37,080 (AstraZeneca AB), WO 00/17,200 (Byk Gulden Lomberg Chem.), and U.S. Pat. No. 4,450,164 (Schering Corporation) as a reversible proton pump inhibitor. Further, pyrimidine derivatives are also disclosed in European Patent No. 775,120 (Yuhan Corp.).

DISCLOSURE OF INVENTION

Technical Problem

The present invention provides novel pyrrolo[3,2-b]pyridine derivatives or pharmaceutically acceptable salts thereof, which have excellent proton pump inhibition effects and possess the ability to attain a reversible proton pump inhibitory effect.

Technical Solution

According to an aspect of the present invention, there is provided a pyrrolo[3,2-b]pyridine derivative or a pharmaceutically acceptable salt thereof.

Further, according to another aspect of the present invention, there is provided a process for the preparation of the pyrrolo[3,2-b]pyridine derivative or a pharmaceutically acceptable salt thereof.

Further, according to another aspect of the present invention, there is provided a pharmaceutical composition comprising the pyrrolo[3,2-b]pyridine derivative or a pharmaceutically acceptable salt thereof as an active ingredient and a pharmaceutically acceptable carrier.

BEST MODE

In accordance with an aspect of the present invention, there is provided a compound of the formula (I) or a pharmaceutically acceptable salt thereof:

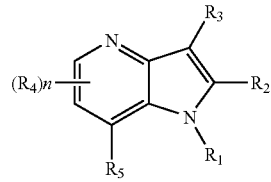

wherein:

$R_1$ is hydrogen; a straight or branched $C_1$-$C_6$ alkyl group, optionally substituted with one or more substituents selected from the group consisting of $C_1$-$C_5$ alkoxy, hydroxy, $C_3$-$C_7$ cycloalkyl, acetoxy, $C_2$-$C_6$ alkenyloxy, $C_1$-$C_3$ alkoxycarbonyl, amino optionally one or two substituted with $C_1$-$C_3$ alkyl, cyano, naphthyl, pyridyl, oxiranyl, oxazolidinonyl, isoxazolyl optionally one or more substituted with $C_1$-$C_3$ alkyl, 1,3-dioxolanyl, and 2,3-dihydrobenzo[1,4]dioxinyl; a straight or branched $C_2$-$C_6$ alkenyl group; a straight or branched $C_2$-$C_6$ alkynyl group; or a benzyl group, optionally substituted with one or more substituents selected from the group consisting of halogen, $C_1$-$C_3$ alkyl, $C_1$-$C_3$ alkoxy, cyano, $C_1$-$C_3$ alkoxycarbonyl, and trifluoro-$C_1$-$C_3$ alkyl, $R_2$ is a straight or branched $C_1$-$C_6$ alkyl group, $R_3$ is a straight or branched $C_1$-$C_6$ alkyl group optionally substituted with hydroxy, $R_4$ is hydrogen; a straight or branched $C_1$-$C_6$ alkyl group; halogen; cyano; hydroxycarbonyl; aminocarbonyl; or $C_3$-$C_7$ cycloalkyl-aminocarbonyl, $R_5$ is a 1,2,3,4-tetrahydroisoquinolinyl group optionally one or more substituted with halogen or $C_1$-$C_5$ alkyl; a benzyloxy group optionally substituted with one or more substituents selected from the group consisting of halogen, $C_1$-$C_5$ alkyl, $C_1$-$C_5$ alkoxy, and trifluoro-$C_1$-$C_3$ alkyl; an amino group optionally substituted with one or two substituents selected from the group consisting of $C_1$-$C_5$ alkoxy-carbonyl and benzyl optionally substituted with halogen; a phenyl group optionally one or more substituted with halogen; a phenoxy group optionally one or more substituted with halogen; a pyridyl-$C_1$-$C_3$ alkoxy group; or a piperonyloxy group, and n is 1 or 2.

Among the compounds of the formula (I) or its pharmaceutically acceptable salt of the present invention, preferred are those wherein:

$R_1$ is hydrogen; a straight or branched $C_1$-$C_6$ alkyl group; a $C_1$-$C_3$ alkyl group substituted with one or more substituents selected from the group consisting of methoxy, hydroxy, cyclopropyl, cyclobutyl, acetoxy, vinyloxy, methoxycarbonyl, dimethylamino, cyano, naphthyl, pyridyl, oxiranyl, oxazolidinonyl, dimethylisoxazolyl, 1,3-dioxolanyl, and 2,3-dihydrobenzo[1,4]dioxinyl; a straight or branched $C_2$-$C_6$ alkenyl group; a straight or branched $C_2$-$C_6$ alkynyl group; or a benzyl group, optionally substituted with one or more substituents selected from the group consisting of halogen, $C_1$-$C_3$ alkyl, $C_1$-$C_3$ alkoxy, cyano, methoxycarbonyl, and trifluoromethyl, $R_2$ is a methyl group, $R_3$ is a methyl group or a hydroxymethyl group, $R_4$ is hydrogen; a methyl group; halogen; cyano; hydroxycarbonyl; aminocarbonyl; or cyclopropylaminocarbonyl;

$R_5$ is 1,2,3,4-tetrahydroisoquinolinyl; 6-fluoro-1-methyl-1,2,3,4-tetrahydroisoquinolinyl; a benzyloxy group substituted with one or more substituents selected from the group consisting of halogen, $C_1$-$C_5$ alkyl, $C_1$-$C_5$ alkoxy, and trifluoromethyl; an amino group one or two substituted with tert-butoxycarbonyl or fluorobenzyl; a fluorophenyl group; a fluorophenoxy group; pyridyl-methoxy; or piperonyloxy, and n is 1 or 2.

The compounds of the present invention may be pharmaceutically acceptable non-toxic salt forms. The non-toxic salts may include conventional acid addition salts used in the field of anti-ulcer agents, e.g., salts originated from inorganic acid such as hydrochloric acid, hydrobromic acid, sulfuric acid, sulfamic acid, phosphoric acid, or nitric acid, and organic acid such as acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxybenzoic acid, fumaric acid, camphosulfonic acid, benzenesulfonic acid, p-toluenesulfonic acid, oxalic acid, or trifluoroacetic acid. Such acid addition salts may be prepared in accordance with any of the conventional methods.

The present invention includes, within its scope, a process for preparing a compound of formula (I) or a pharmaceutically acceptable salt thereof, in accordance with the following Scheme 1:

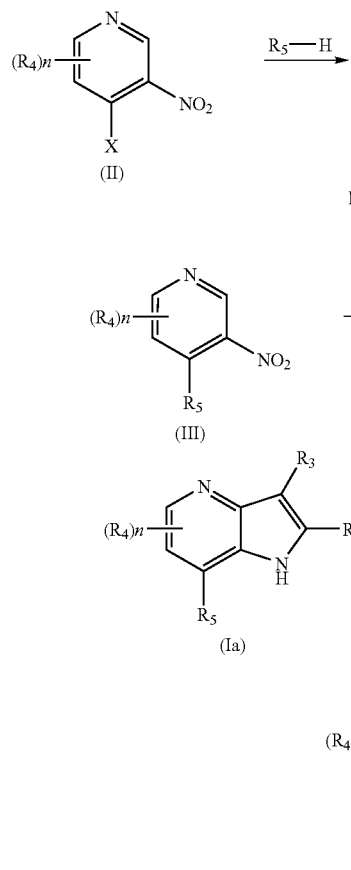

wherein, $R_1$, $R_2$, $R_3$, $R_4$, $R_5$, and n are the same as defined in the above and X is halogen.

Specifically, the compound of formula (I) or its pharmaceutically acceptable salt may be prepared using a process which comprises: reacting a compound of formula (II) with $R_5$—H to obtain a compound of formula (III), reacting the compound of formula (III) with a compound of formula (IV) to obtain a compound of formula (Ia), and reacting the compound of formula (Ia) with $R_1$—X to obtain a compound of formula (I).

In the processes of Scheme 1, the compounds of formula (II) and (IV) are commercially available. The reaction of the compound of formula (II) and $R_5$—H may be performed in the presence of a base, such as sodium hydride, potassium tert-butoxide, sodium carbonate, or potassium hydroxide. Further, the reaction may be carried out in an organic solvent, such as anhydrous tetrahydrofuran and N,N-dimethylformamide, and at room temperature or under heating, e.g., at a temperature of 40° C.~140° C.

The cyclization reaction of a compound of formula (III) and a compound of formula (IV) may be performed in an organic solvent, e.g., anhydrous tetrahydrofuran. Further, the reaction may be carried out at a temperature of −78° C.~20° C. or at room temperature.

The compound of formula (Ia) is reacted with $R_1$—X to obtain a compound of formula (I). The reaction of the compound of formula (Ia) and $R_1$—X may be performed in the presence of a base, such as sodium hydride or potassium tert-butoxide. Further, the reaction may be carried out in an organic solvent, such as tetrahydrofuran or N,N-dimethylformamide, and at room temperature or at a temperature of 40° C.~100° C. In order to increase a reaction rate and/or a yield of the reaction, a catalytic amount of 18-crown-6 may be used.

In accordance with another aspect of the present invention, the compound of formula (Ic) or its pharmaceutically acceptable salt may be prepared in accordance with the following Scheme 2:

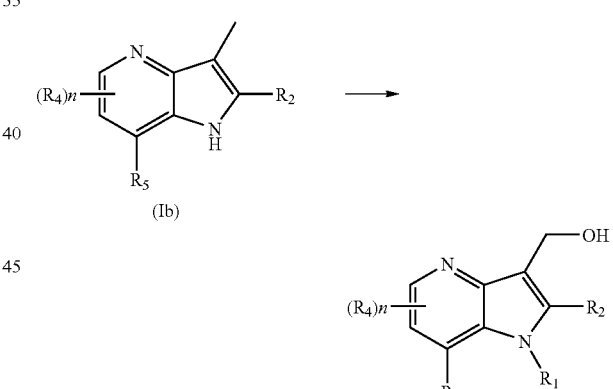

wherein, $R_1$, $R_2$, $R_4$, and $R_5$ are the same as defined in the above.

Specifically, the compound of formula (Ic) or its pharmaceutically acceptable salt may be prepared using a process which comprises: hydrolyzing a compound of formula (Ib) with a hydrolyzing agent, e.g., lithium hydroxide, in the presence of ammonium cerium (IV) nitrate and acetic acid.

In accordance with another aspect of the present invention, the compound of formula (Ig) or its pharmaceutically acceptable salt may be prepared using a process which comprises: reacting a compound of formula (Id) with copper cyanide (CuCN) to obtain a compound of formula (Ie); hydrolyzing the compound of formula (Ie) to obtain a compound of formula (If); and reacting a compound of formula (If) with a compound of formula (V) to obtain a compound of formula (Ig), as the following Scheme 3:

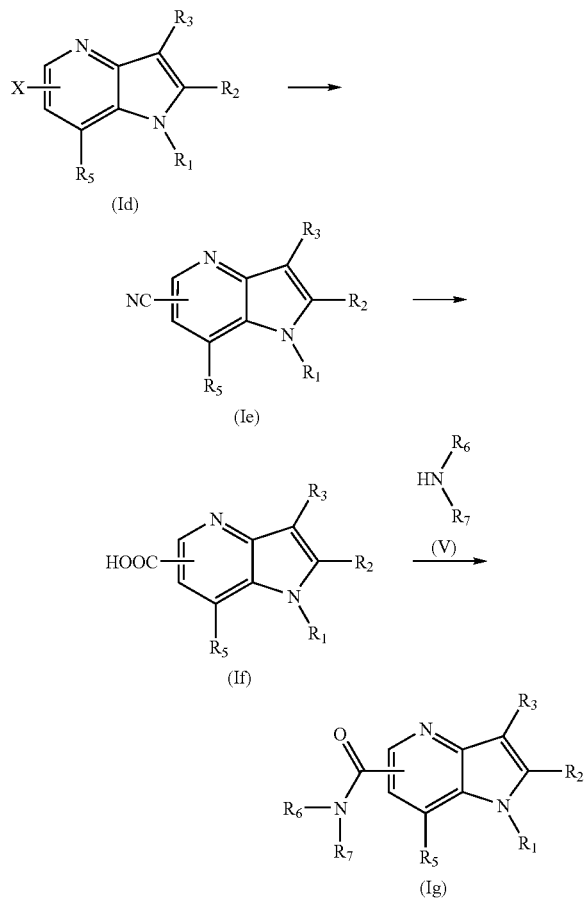

wherein, $R_1$, $R_2$, $R_3$, $R_5$ and X are the same as defined in the above and $R_6$ and $R_7$ are, independently of each other, hydrogen or a $C_3$-$C_7$ cycloalkyl group.

In the processes of Scheme 3, the compound of formula (Ie) may be obtained by refluxing a compound of formula (Id) and copper cyanide (CuCN) in an organic solvent, e.g., N,N-dimethylformamide.

The compound of formula (Ie) is hydrolyzed in the acidic or basic condition to produce a compound of formula (If). The hydrolysis reaction may be carried out with a potassium hydroxide solution at a temperature of 50° C.~100° C.

The reaction of the compound of formula (If) and a compound of formula (V) may be performed in the presence of a coupling agent, e.g., N-(3-dimethylaminopropyl)-N'-ethyl-carbodiimide (EDC) or 1-hydroxy-7-azabenzotriazole (HOBT). The coupling reaction may be carried out in an organic solvent, e.g., dichloromethane or N,N-dimethylformamide.

The present invention further includes, within its scope, a pharmaceutical composition comprising a therapeutically effective amount of any of the compound of formula (I), as defined above, or a pharmaceutically acceptable salt thereof and a pharmaceutically acceptable carrier. The compound of formula (I) or a pharmaceutically acceptable salt thereof may be used for prevention and treatment of gastrointestinal inflammatory diseases and gastric acid-related diseases in mammals including human, such as gastritis, gastric ulcer, duodenal ulcer, reflux esophagitis and Zollinger-Ellison syndrome. Furthermore, the compounds or their salts of the present invention may be used for treatment of other gastrointestinal disorders where gastric antisecretory effect is desirable, e.g. in patients with gastrinomas, and in patients with acute upper gastrointestinal bleeding. The compounds or their salts of the present invention may also be used in patients in intensive care situations, and pre- and postoperatively to prevent acid aspiration and stress ulceration.

The composition of the present invention may include additives such as lactose or corn starch, lubricants such as magnesium stearate, emulsifiers, suspending agents, stabilizers, and isotonic agents. If necessary, sweetening agents and/or flavoring agents may be added.

The composition of the present invention may be administered orally or parenterally, including intravenous, intraperitoneal, subcutaneous, rectal and topical routes of administration. Therefore, the composition of the present invention may be formulated into various forms such as tablets, capsules, aqueous solutions or suspensions. In the case of tablets for oral use, carriers such as lactose, corn starch, and lubricating agents, e.g. magnesium stearate, are commonly added. In the case of capsules for oral administration, lactose and/or dried corn starch can be used as a diluent. When an aqueous suspension is required for oral use, the active ingredient may be combined with emulsifying and/or suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic. The composition of the present invention may be in the form of an aqueous solution containing pharmaceutically acceptable carriers, e.g., saline, at a pH level of 7.4. The solutions may be introduced into a patient's intramuscular blood-stream by local bolus injection.

The compounds of the present invention may be administered in an effective amount ranging from about 0.1 mg/kg to about 500 mg/kg per day to a subject patient. Of course, the dosage may be changed according to the patient's age, weight, susceptibility, or symptom.

The following examples are provided for illustration purposes only, and are not intended to limit the scope of the invention.

Preparation 1. 2-(3-nitropyridin-4-yl)-1,2,3,4-tetrahydroisoquinoline

Step 1: 4-chloro-3-nitropyridine

4-Hydroxy-3-nitropyridine (10.0 g, 71.38 mmol) was added to 100 ml of phosphorus oxychloride, which was then refluxed under stirring for 1 hour. The reaction mixture was concentrated under reduced pressure. The resulting residue was added to 500 ml of ice water, which was then neutralized with 2N sodium hydroxide solution. The reaction mixture was extracted with methylene chloride (300 ml). The separated organic layer was dried on anhydrous magnesium sulfate and concentrated under reduced pressure to give the titled compound of a pale yellow solid (9.2 g, 92.0%).

TLC: n-hexane/ethyl acetate=2/1(v/v): Rf=0.5

$^1$H-NMR (CDCl$_3$) δ9.12 (s, 1H), 8.69 (d, 1H), 7.55 (d, 1H)

Step 2: 2-(3-nitropyridin-4-yl)-1,2,3,4-tetrahydroisoquinoline

Sodium hydride (60%, 386.4 mg, 9.66 mmol) was added at 0° C. to a solution of 1,2,3,4-tetrahydroisoquinoline (1.06 ml, 8.05 mmol) in N,N-dimethylformamide (30 ml) and stirred for 10 minutes at the same temperature. 4-Chloro-3-nitropyridine (1.124 g, 7.09 mmol) prepared in Step 1 was added to the reaction mixture, which was stirred for 2 hours at room temperature, diluted with a mixture of water (10 ml) and ethyl acetate (100 ml), and then washed with water (100 ml) twice. The separated organic layer was dried on anhydrous magnesium sulfate and concentrated under reduced pressure to give the titled compound as a yellow solid (1.13 g, 89.3%).

TLC: n-hexane/ethyl acetate=2/1(v/v): Rf=0.3

$^1$H-NMR (CDCl$_3$) δ8.86 (s, 1H), 8.36 (d, 2H), 7.22 (m, 3H), 7.12 (m, 1H), 6.96 (d, 1H), 4.35 (s, 2H), 3.53 (t, 2H), 3.03 (t, 2H)

Preparation 2. 4-(4-fluorobenzyloxy)-3-nitropyridine

4-Chloro-3-nitropyridine (2.0 g, 12.62 mmol) prepared in Step 1 of Preparation 1 was added to a suspension of 4-fluorobenzyl alcohol (2.04 ml, 18.92 mmol), potassium carbonate (1.74 g, 12.62 mmol), and potassium hydroxide (2.38 g, 50.48 mmol) in anhydrous toluene (100 ml). A catalytic amount of tris[2-(2-methoxyethoxy)ethyl]amine was added to the reaction mixture, which was then stirred for 1 hour at room temperature. The reaction mixture was filtered and then concentrated under reduced pressure. The resulting residue was purified with silica gel column chromatography (ethyl acetate/n-hexane=1/1, (v/v)) to give the titled compound as a white solid (2.5 g, 86.3%).

TLC: n-hexane/ethyl acetate (2/1): Rf=0.4

$^1$H-NMR (CDCl$_3$) δ8.57 (s, 1H), 7.28 (m, 3H), 7.16 (m, 2H), 6.70 (d, 1H), 5.05 (s, 2H)

Preparation 3. (2,3-dimethyl-1H-pyrrolo[3,2-b]pyridin-7-yl)-(4-fluorobenzyl)carbamic acid tert-butyl ester

Step 1: (4-fluorobenzyl)-(3-nitropyridin-4-yl)-amine

Sodium carbonate (3.20 g, 30.27 mmol) and 4-fluorobenzylamine (2.14 ml, 18.92 mmol) were added to a solution of 4-chloro-3-nitropyridine (3.0 g, 18.92 mmol) prepared in Step 1 of Preparation 1 in 30 ml of anhydrous N,N-dimethylformamide and then the reaction mixture was stirred for 1 hour at 80° C. The reaction mixture was diluted with a mixture of water (10 ml) and ethyl acetate (100 ml) and then washed with water (100 ml) twice. The separated organic layer was dried on anhydrous magnesium sulfate and then concentrated under reduced pressure to give the titled compound as a yellow solid (3.01 g, 83.5%).

$^1$H-NMR (CDCl$_3$) δ8.60 (s, 1H), 7.29 (m, 3H), 7.18 (m, 2H), 6.70 (d, 1H), 5.05 (s, 2H)

Step 2: (4-fluorobenzyl)-(3-nitropyridin-4-yl)-carbamic acid tert-butyl ester Di-tert-butyl dicarbonate (8.13 g, 37.25 mmol) and N,N-dimethylaminopyridine (2.27 g, 18.63 mmol) were added to a solution of (4-fluorobenzyl)-(3-nitropyridin-4-yl)-amine (3.07 g, 12.42 mmol) prepared in Step 1 in 100 ml of tetrahydrofuran and then the reaction mixture was stirred for 24 hours. The reaction mixture was concentrated under reduced pressure. The resulting residue was purified with silica gel column chromatography (ethyl acetate/n-hexane=1/1, (v/v)) to give the titled compound as yellow oil (2.9 g, 75.6%).

$^1$H-NMR (CDCl$_3$) δ8.60 (s, 1H), 7.29 (m, 3H), 7.18 (m, 2H), 6.70 (d, 1H), 5.10 (s, 2H), 1.3 (s, 9H)

Step 3: (2,3-dimethyl-1H-pyrrolo[3,2-b]pyridin-7-yl)-(4-fluorobenzyl)-carbamic acid tert-butyl ester (4-Fluorobenzyl)-(3-nitropyridin-4-yl)-carbamic acid tert-butyl ester (10.2 g) prepared in Step 2 was dissolved in anhydrous tetrahydrofuran (200 ml) under a nitrogen atmosphere. 1-Methyl-1-propenyl magnesium bromide (0.5M in tetrahydrofuran solution, 110 ml, 130.5 mmol) was added at −78° C. to the solution, which was stirred for 5 hours at −20° C. 20 ml of 20% ammonium chloride solution was added to the reaction mixture, which was then extracted with ethyl acetate (200 ml) twice. The separated organic layer was dried on anhydrous magnesium sulfate and then concentrated under reduced pressure. The resulting residue was purified with silica gel column chromatography (ethyl acetate/methanol=10/1, (v/v)) to give the titled compound as a pale yellow solid (3.8 g, 28.9%).

$^1$H-NMR (CDCl$_3$) δ8.31 (d, 1H), 8.12 (s, 1H), 7.40 (m, 1H), 7.18 (d, 2H), 7.09 (d, 2H), 3.16 (s, 3H), 2.53 (s, 3H), 2.48 (s, 3H), 1.41 (s, 9H)

Example 1

1-(4-chlorobenzyl)-7-(1,2,3,4-tetrahydroisoquinolin-2-yl)-2,3-dimethyl-1H-pyrrolo[3,2-b]pyridine hydrochloride

Step 1: 2-(2,3-dimethyl-1H-pyrrolo[3,2-b]pyridin-7-yl)-1,2,3,4-tetrahydroisoquinoline 2-(3-Nitropyridin-4-yl)-1,2,3,4-tetrahydroisoquinoline (5 g, 19.58 mmol) prepared in Preparation 1 was dissolved in anhydrous tetrahydrofuran (200 ml) under a nitrogen atmosphere. 1-Methyl-1-propenyl magnesium bromide (0.5M in tetrahydrofuran solution, 80 ml, 117.5 mmol) was added at −78° C. to the solution, which was then stirred for 5 hours at −20° C. 20 ml of 20% ammonium chloride solution was added to the reaction mixture, which was then extracted with ethyl acetate (200 ml) twice. The separated organic layer was dried on anhydrous magnesium sulfate and then concentrated under reduced pressure. The resulting residue was purified with silica gel column chromatography (ethyl acetate/methylene chloride/methanol=10/10/1, (v/v/v)) to give the titled compound as a pale yellow solid (2.1 g, 25.3%).

$^1$H-NMR (CDCl$_3$) δ8.26 (d, 1H), 7.77 (s, 1H), 7.19 (m, 4H), 6.59 (d, 1H), 4.46 (s, 2H), 3.64 (t, 2H), 3.04 (t, 2H), 2.41 (s, 3H), 2.30 (s, 3H)

Step 2: 1-(4-chlorobenzyl)-7-(1,2,3,4-tetrahydroisoquinolin-2-yl)-2,3-dimethyl-1H-pyrrolo[3,2-b]pyridine hydrochloride 2-(2,3-dimethyl-1H-pyrrolo[3,2-b]pyridin-7-yl)-1,2,3,4-tetrahydroisoquinoline (30 mg, 0.108 mmol) prepared in Step 1, potassium tert-butoxide (13.6 mg, 0.162 mmol), and a catalytic amount of 18-crown-6 were added to anhydrous tetrahydrofuran (2 ml). 4-Chlorobenzyl chloride (0.09 ml, 0.162 mmol) was added to the reaction mixture, which was then stirred for 12 hours at room temperature. The reaction mixture was concentrated under reduced pressure. The resulting residue was purified with silica gel column chromatography (ethyl acetate/methylene chloride/methanol=10/10/1, (v/v/v)), dissolved in ethyl acetate (1 ml), and then saturated with hydrochloric acid gas. The resulting precipitate was filtered to give the titled compound as a white solid (6.9 mg, 15.8%).

$^1$H-NMR (CDCl$_3$) δ8.34 (d, 1H), 7.17 (m, 5H), 6.98 (m, 1H), 6.89 (m, 1H), 6.54 (d, 2H), 5.51 (s, 2H), 4.39 (s, 2H), 3.57 (s, 2H), 2.93 (d, 2H), 2.59 (s, 3H), 2.25 (s, 3H)

Examples 2 to 29

The titled compounds of Examples 2 to 29 were prepared, in accordance with the same procedures as in Step 2 of Example 1, using 2-(2,3-dimethyl-1H-pyrrolo[3,2-b]pyridin-7-yl)-1,2,3,4-tetrahydroisoquinoline prepared in Step 1 of Example 1; and, 2-(bromomethyl)naphthalene, 2-bromomethyl-1,3-dioxolane, (bromomethyl)cyclopropane, 2-bromoethyl methyl ether, benzyl bromide, allyl bromide, 3-methoxybenzyl chloride, 2-fluorobenzyl chloride, 4-methoxybenzyl chloride, 1-iodopropane, 3-methylbenzyl chloride, iodoethane, 2-(2-bromoethyl)-1,3-dioxolane, 2-bromomethyl-1,4-benzodioxane, 4-bromo-2-methyl-2-butene, 4-bromomethyl-3,5-dimethylisoxazole, 2-chlorobenzyl chloride, 1-bromoethyl acetate, bromomethyl methyl ether, 4-tert-butylbenzyl chloride, (bromomethyl)cyclobutane, 3-cyanobenzyl bromide, bromomethyl acetate, 2,4-dimethylbenzyl bromide, 4-methoxycarbonylbenzyl bromide, 2-(bromoethyl)vinyl ether, 1-bromo-2-methyl-propane, or epibromohydrin.

Example 2

1-(2-naphthylmethyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.36 (d, 1H), 7.82 (m, 1H), 7.73 (m, 1H), 7.65 (m, 1H), 7.50 (m, 2H), 7.15 (m, 5H), 6.78 (m, 2H), 5.67 (s, 2H), 4.43 (s, 2H), 3.59 (m, 2H), 2.88 (m, 2H), 2.64 (s, 3H), 2.35 (s, 3H); (Yield: 78.9%)

Example 3

1-(1,3-dioxolan-2-ylmethyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.30 (d, 1H), 7.21 (m, 3H), 7.14 (m, 2H), 4.83 (t, 1H), 4.74 (m, 4H), 3.85 (m, 3H), 3.35 (m, 2H), 3.05 (m, 3H), 2.59 (s, 3H), 2.50 (s, 3H); (Yield: 86.3%)

Example 4

1-cyclopropylmethyl-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.31 (d, 1H), 7.22 (m, 3H), 7.11 (m, 2H), 4.54 (d, 2H), 4.14 (s, 2H), 3.70 (m, 2H), 3.08 (m, 2H), 2.54 (s, 2H), 2.41 (s, 3H), 2.35 (s, 3H), 0.83 (m, 1H), 0.32 (m, 2H), 0.08 (m, 2H); (Yield: 69.8%)

Example 5

1-(2-methoxyethyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.34 (d, 1H), 7.22 (m, 3H), 7.11 (m, 2H), 4.44 (m, 4H), 3.66 (m, 2H), 3.38 (m, 2H), 3.07 (s, 3H), 2.50 (s, 3H), 2.42 (s, 3H); (Yield: 78.6%)

Example 6

1-benzyl-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.34 (m, 1H), 7.18 (m, 4H), 7.02 (m, 5H), 6.93 (m, 1H), 5.56 (s, 2H), 4.37 (s, 2H), 3.56 (m, 2H), 2.98 (m, 2H), 2.59 (s, 3H), 2.25 (s, 3H); (Yield: 68.7%)

Example 7

1-allyl-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.26 (s, 1H), 7.20 (m, 3H), 6.88 (m, 1H), 6.67 (m, 1H), 5.88 d, 2H), 5.66 (m, 1H), 4.49 (s, 2H), 4.33 (d, 1H), 4.25 (d, 1H), 3.63 (s, 2H), 3.05 (s, 2H), 2.55 (s, 3H), 2.42 (s, 3H); (Yield: 73.5%)

Example 8

1-(3-methoxybenzyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.31 (m, 1H), 7.03 (m, 4H), 6.86 (m, 3H), 6.20 (m, 2H), 5.58 (s, 2H), 4.52 (s, 2H), 3.68 (s, 3H), 3.45 (m, 2H), 2.95 (m, 2H), 2.55 (s, 3H), 2.34 (s, 3H); (Yield: 77.0%)

Example 9

1-(2-fluorobenzyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.36 (d, 1H), 7.00 (m, 4H), 6.91 (m, 4H), 6.86 (m, 1H), 6.39 (s, 1H), 5.63 (s, 2H), 4.47 (m, 2H), 3.63 (m, 2H), 2.96 (m, 2H), 2.53 (s, 3H), 2.47 (s, 3H); (Yield: 74.5%)

Example 10

1-(4-methoxybenzyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.27 (d, 1H), 7.32 (m, 3H), 7.00 (m, 3H), 6.77 (m, 3H), 5.51 (s, 2H), 4.55 (m, 2H), 3.77 (s, 3H), 2.97 (m, 4H), 2.45 (s, 3H), 2.33 (s, 3H); (Yield: 86.9%)

Example 11

1-propyl-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.35 (d, 1H), 7.12 (m, 5H), 4.56 (s, 2H), 4.33 (t, 2H), 3.32 (m, 2H), 2.80 (m, 2H), 2.34 (s, 3H), 2.28 (s, 3H), 1.98 (m, 2H), 1.53 (d, 3H); (Yield: 78.0%)

Example 12

1-(3-methylbenzyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.42 (d, 1H), 6.92 (m, 4H), 6.87 (m, 1H), 6.48 (m, 4H), 5.66 (s, 2H), 4.59 (m, 2H), 3.72 (m, 2H), 3.08 (m, 2H), 2.64 (s, 3H), 2.48 (s, 3H), 2.10 (s, 3H); (Yield: 75.6%)

Example 13

1-ethyl-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.29 (d, 1H), 7.23 (m, 4H), 7.00 (d, 1H), 4.56 (d, 2H), 4.32 (m, 2H), 3.67 (m, 2H), 3.08 (m, 2H), 2.59 (s, 3H), 2.48 (s, 3H), 1.06 (t, 3H); (Yield: 77.0%)

Example 14

1-[2-(1,3-dioxolan-2-yl)ethyl]-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.34 (s, 1H), 7.17 (m, 4H), 7.10 (s, 1H), 4.83 (m, 2H), 4.39 (s, 2H), 4.01 (m, 1H), 3.57 (s, 2H), 3.12 (m, 4H), 2.93 (m, 2H), 2.56 (s, 3H), 2.47 (s, 3H), 1.89 (m, 2H); (Yield: 58.4%)

Example 15

1-(2,3-dihydrobenzo[1,4]dioxin-6-ylmethyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.34 (s, 1H), 7.16 (m, 4H), 7.10 (m, 4H), 5.41 (s, 2H), 4.21 (s, 2H), 4.01 (m, 4H), 3.69 (s, 2H), 2.93 (m, 2H), 2.57 (s, 3H), 2.48 (s, 3H); (Yield: 58.6%)

Example 16

1-(3-methylbuten-2-yl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.35 (s, 1H), 7.51 (m, 4H), 7.10 (s, 1H), 4.86 (d, 2H), 4.39 (s, 2H), 4.10 (m, 1H), 3.57 (m, 2H), 2.95 (m, 2H), 2.56 (s, 3H), 2.35 (s, 3H), 1.89 (s, 6H); (Yield: 78.5%)

Example 17

1-(3,5-dimethylisoxazol-4-ylmethyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.37 (d, 1H), 7.19 (m, 3H), 6.88 (m, 2H), 5.40 (s, 2H), 4.40 (s, 2H), 3.49 (m, 2H), 3.03 (m, 2H), 2.58 (s, 3H), 2.32 (s, 3H), 1.91 (s, 3H), 1.65 (s, 3H); (Yield: 57.8%)

Example 18

1-(2-chlorobenzyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.35 (d, 1H), 7.21 (m, 4H), 6.98 (m, 6H), 5.66 (s, 2H), 4.82 (s, 2H), 4.54 (m, 2H), 3.51 (m, 2H), 2.54 (s, 3H), 2.33 (s, 3H); (Yield: 75.4%)

Example 19

1-methoxycarbonylethyl-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.09 (m, 1H), 7.21 (m, 5H), 4.45 (m, 4H), 4.11 (m, 4H), 3.83 (m, 2H), 3.07 (s, 3H), 2.65 (s, 3H), 2.55 (s, 3H); (Yield: 83.0%)

Example 20

1-methoxymethyl-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.30 (m, 1H), 7.23 (m, 3H), 6.98 (m, 2H), 5.524 (s, 2H), 4.55 (s, 2H), 3.89 (m, 2H), 3.48 (m, 2H), 3.09 (s, 3H), 2.53 (s, 3H), 2.50 (s, 3H); (Yield: 69.3%)

Example 21

1-(4-tert-butylbenzyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.31 (s, 1H), 7.20 (m, 4H), 6.99 (m, 4H), 5.65 (s, 2H), 4.51 (s, 2H), 3.77 (m, 2H), 3.06 (m, 2H), 2.59 (s, 3H), 2.32 (s, 3H), 1.27 (s, 9H); (Yield: 72.0%)

Example 22

1-cyclobutylmethyl-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.27 (s, 1H), 7.17 (m, 3H), 7.00 (m, 2H), 4.45 (s, 2H), 4.27 (s, 2H), 3.70 (m, 2H), 3.09 (m, 2H), 2.57 (s, 3H), 2.465 (s, 3H), 2.84 (m, 1H), 1.66 (m, 4H), 1.43 (m, 2H); (Yield: 83.5%)

Example 23

1-(3-cyanobenzyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ7.79-7.50 (m, 5H), 7.48 (m, 2H), 7.21 (m, 3H), 5.61 (s, 2H), 4.40 (m, 2H), 3.51 (m, 2H), 2.96 (m, 2H), 2.43 (s, 3H), 2.36 (s, 3H); (Yield: 58.4%)

Example 24

1-methoxycarbonylmethyl-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.39 (m, 1H), 7.11-7.09 (m, 5H), 5.21 (s, 2H), 4.46 (s, 2H), 3.74 (s, 3H), 3.47 (m, 2H), 3.07 (m, 2H), 2.58 (s, 3H), 2.51 (s, 3H); (Yield: 66.8%)

Example 25

1-(2,4-dimethylbenzyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.38 (m, 1H), 7.09 (m, 6H), 6.40 (m, 1H), 6.02 (s, 1H), 5.46 (m, 2H), 4.20 (m, 2H), 3.53 (m, 2H), 2.97 (m, 2H), 2.65 (s, 3H), 2.28 (s, 3H), 1.77 (s, 6H); (Yield: 78.5%)

Example 26

1-(4-methoxycarbonylbenzyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.21 (d, 1H), 7.98 (d, 1H), 7.20 (m, 4H), 6.98 (m, 4H), 5.60 (s, 2H), 4.68 (s, 2H), 3.67 (s, 3H), 3.05 (m, 2H), 2.88 (m, 2H), 2.34 (s, 3H), 2.28 (s, 3H) (Yield: 65.0%)

Example 27

1-(2-vinyloxyethyl)-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.36 (s, 1H), 7.50 (m, 4H), 7.10 (s, 1H), 4.80 (d, 2H), 4.72 (s, 2H), 4.23 (m, 1H), 3.78 (m, 2H), 3.60 (m, 2H), 3.49 (m, 2H), 2.93 (m, 2H), 2.35 (s, 3H), 2.28 (s, 3H); (Yield: 48.7%)

Example 28

1-isobutyl-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.35 (s, 1H), 7.38 (m, 4H), 7.14 (s, 1H), 4.89 (s, 2H), 4.75 (d, 2H), 3.69 (m, 2H), 2.98 (m, 2H), 2.58 (s, 3H), 2.55 (s, 3H), 1.99 (m, 1H), 1.57 (d, 6H); (Yield: 75.1%)

Example 29

1-oxiranylmethyl-7-(1,2,3,4-tetrahydroisoquinolin-2-yl)-2,3-dimethyl-1H-pyrrolo[3,2-b]pyridine hydrochloride $^1$H-NMR (CDCl$_3$) δ8.36 (s, 1H), 7.48 (m, 4H), 7.12 (s, 1H), 5.11 (s, 2H), 4.89 (s, 2H), 3.68 (m, 2H), 3.60 (m, 2H), 3.55 (m, 1H), 2.89 (m, 2H), 2.58 (s, 3H), 2.55 (s, 3H); (Yield: 57.4%)

Example 30

1-benzyl-7-(1,2,3,4-tetrahydroisoquinolin-2-yl)-3-hydroxymethyl-2-methyl-1H-pyrrolo[3,2-b]pyridine hydrochloride The compound prepared in Example 6 (501.1 mg, 1.23 mmol) was treated with a saturated sodium bicarbonate solution to obtain 1-benzyl-7-(1,2,3,4-tetrahydroisoquinolin-2-yl)-2,3-dimethyl-1H-pyrrolo[3,2-b]pyridine (433.6 mg, 1.18 mmol). Ammonium cerium (IV) nitrate (1.94 g, 3.54 mmol) was added at room temperature to a solution of 1-benzyl-7-(1,2,3,4-tetrahydroisoquinolin-2-yl)-2,3-dimethyl-1H-pyrrolo[3,2-b]pyridine (433.6 mg, 1.18 mmol) in acetic acid (10 ml). The reaction mixture was stirred for 4 hours at 55° C., cooled to room temperature, poured in water, and then extracted with ethyl acetate. The resulting organic layer was washed with a saturated sodium chloride solution, dried on anhydrous magnesium sulfate, and then concentrated under reduced pressure. The resulting residue was dissolved in methanol (20 ml). 2N Lithium hydroxide (5.0 ml) was added to the solution, which was then stirred for 1 hour at room temperature. The reaction mixture was neutralized with 1N hydrochloric acid, concentrated under reduced pressure to discard methanol, and then extracted with ethyl acetate. The resulting organic layer was dried on anhydrous magnesium sulfate and then concentrated under reduced pressure. The resulting residue was purified with silica gel column chromatography to give 1-benzyl-7-(1,2,3,4-tetrahydroisoquinolin-2-yl)-3-hydroxymethyl-2-methyl-1H-pyrrolo[3,2-b]pyridine, which was then dissolved in ethyl acetate. The solution was saturated with hydrochloric acid gas and then filtered to give the titled compound as a white solid (69 mg, 13.9%).

$^1$H-NMR (CDCl$_3$) δ8.75 (d, 1H), 7.95 (d, 1H), 7.13 (m, 4H), 6.74 (m, 5H), 5.79 (s, 2H), 4.14 (m, 2H), 3.26 (m, 2H), 4.10 (s, 2H), 2.80 (m, 2H), 2.34 (s, 3H)

Example 31

2-(2,3-dimethyl-1H-pyrrolo[3,2-b]pyridin-7-yl)-6-fluoro-1-methyl-1,2,3,4-tetrahydroisoquinoline Step 1: 6-fluoro-1-methyl-2-(3-nitropyridin-4-yl)-1,2,3,4-tetrahydroisoquinoline In accordance with the same procedures as in Step 2 of Preparation 1, except for using 6-fluoro-1-methyl-1,2,3,4-tetrahydroisoquinoline prepared in accordance with a method disclosed in WO 94/14795, the titled compound was obtained as a pale yellow solid. (Yield: 85.3%) The product was used in the subsequent step without further purification.

Step 2: 2-(2,3-dimethyl-1H-pyrrolo[3,2-b]pyridin-7-yl)-6-fluoro-1-methyl-1,2,3,4-tetrahydroisoquinoline In accordance with the same procedures as in Step 1 of Example 1, except for using 6-fluoro-1-methyl-2-(3-nitropyridin-4-yl)-1,2,3,4-tetrahydroisoquinoline prepared in Step 1, the titled compound was obtained as a white solid. (Yield: 15.7%)

$^1$H-NMR (CDCl$_3$) δ10.23 (s, 1H), 8.51 (d, 1H), 7.87 (d, 1H), 7.21 (m, 2H), 7.06 (s, 1H), 4.36 (s, 2H), 3.37 (t, 1H), 3.14 (t, 2H), 2.37 (d, 3H), 2.53 (s, 3H), 2.23 (s, 3H)

Example 32

2-(1-benzyl-2,3-dimethyl-1H-pyrrolo[3,2-b]pyridin-7-yl)-6-fluoro-1-methyl-1,2,3,4-tetrahydroisoquinoline hydrochloride In accordance with the same procedures as in Step 2 of Example 1, except for using 2-(2,3-dimethyl-1H-pyrrolo[3,2-b]pyridine-7-yl)-6-fluoro-1-methyl-1,2,3,4-tetrahydroisoquinoline prepared in Step 2 of Example 31 and benzyl bromide, the titled compound was obtained as a white solid. (Yield: 65.8%)

$^1$H-NMR (CDCl$_3$) δ8.50 (d, 1H), 7.84 (d, 1H), 7.53 (m, 5H), 7.20 (m, 2H), 7.04 (s, 1H), 4.36 (s, 2H), 3.35 (t, 1H), 3.12 (t, 2H), 2.34 (d, 3H), 2.40 (s, 3H), 2.35 (s, 3H)

Example 33

1-(4-chlorobenzyl)-7-(4-fluorobenzyloxy)-2,3-dimethyl-1H-pyrrolo[3,2-b]pyridine hydrochloride Step 1: 7-(4-fluorobenzyloxy)-2,3-dimethyl-1H-pyrrolo[3,2-b]pyridine 4-(4-Fluorobenzyloxy)-3-nitropyridine (4.8 g, 19.34 mmol) prepared in Preparation 2 was dissolved in anhydrous tetrahydrofuran (200 ml) under a nitrogen atmosphere. 1-Methyl-1-propenyl magnesium bromide (0.5M in tetrahydrofuran solution, 116 ml, 58.02 mmol) was added at −78° C. to the solution, which was then stirred for 5 hours at −20° C. 20% Ammonium chloride solution (20 ml) was added to the reaction mixture, which was then extracted with ethyl acetate (200 ml) twice. The separated organic layer was dried on anhydrous magnesium sulfate and then concentrated under reduced pressure. The resulting residue was purified with silica gel column chromatography (ethyl acetate/methylene chloride/methanol=10/10/1, (v/v/v)) to give the titled compound as a pale yellow solid (2.45 g, 28.3%).

$^1$H-NMR (CDCl$_3$) δ8.29 (d, 1H), 7.97 (s, 1H), 7.43 (m, 2H), 7.10 (m, 2H), 6.60 (d, 1H), 5.18 (s, 2H), 2.39 (s, 3H), 2.30 (s, 3H)

Step 2: 1-(4-chlorobenzyl)-7-(4-fluorobenzyloxy)-2,3-dimethyl-1H-pyrrolo[3,2-b]pyridine hydrochloride 7-(4-fluorobenzyloxy)-2,3-dimethyl-1H-pyrrolo[3,2-b]pyridine (25 mg, 0.105 mmol) prepared in Step 1, potassium tert-butoxide (13.6 mg, 0.163 mmol), and a catalytic amount of 18-crown-6 were added to anhydrous tetrahydrofuran (2 ml). 4-Chlorobenzyl chloride (0.089 ml, 0.160 mmol) was added to the reaction mixture, which was then stirred for 12 hours at room temperature. The reaction mixture was concentrated under reduced pressure. The resulting residue was purified with silica gel column chromatography (ethyl acetate/methylene chloride/methanol=10/10/1, (v/v/v)), dissolved in ethyl acetate (1 ml), and then saturated with hydrochloric acid gas. The resulting precipitate was filtered to give the titled compound as a white solid (6.9 mg, 15.8%).

$^1$H-NMR (CDCl$_3$) δ8.38 (s, 1H), 7.24 (d, 2H), 7.03 (m, 4H), 6.87 (s, 1H), 6.52 (d, 2H), 5.50 (s, 2H), 5.22 (s, 2H), 2.60 (s, 3H), 2.37 (s, 3H)

Examples 34 to 62

The titled compounds of Examples 34 to 62 were prepared, in accordance with the same procedures as in Step 2 of Example 33, using 7-(4-fluorobenzyloxy)-2,3-dimethyl-1H-pyrrolo[3,2-b]pyridine prepared in Step 1 of Example 33; and, 4-methylbenzyl chloride, 4-bromomethylmethylbenzoate, 4-tert-butylbenzyl chloride, 2-(bromomethyl)naphthalene, 2-(bromoethyl)vinyl ether, 2-bromomethyl-1,3-dioxolane, 3-fluorobenzyl chloride, 2,5-dimethylbenzyl chloride, 4-bromomethyl-3,5-dimethylisoxazole, 3-chlorobenzyl chloride, 2-chloromethylpyridine, 6-chloromethyl-2,3-dihydrobenzo[1,4]dioxine, 3-cyanobenzyl chloride, epibromohydrin, 3-chloromethylpyridine, allyl bromide, 1-iodo-2-methylpropane, propargyl bromide, 3-methoxybenzyl bromide, 3-methylbenzyl bromide, benzyl bromide, (bromomethyl)cyclobutane, 4-bromo-2-methyl-2-butene, methyl-3-bromopropionate, 4-methoxybenzyl chloride, 2-fluorobenzyl chloride, (bromomethyl)cyclopropane, 2-bromoethyl methyl ether, or 1-iodopropane.

Example 34

7-(4-fluorobenzyloxy)-2,3-dimethyl-1-(4-methylbenzyl)-1H-pyrrolo[3,2-b]pyridine hydrochloride $^1$H-NMR (CDCl$_3$) δ8.32 (d, 1H), 7.01 (m, 6H), 6.59 (m, 3H), 5.68 (s, 2H), 5.35 (s, 2H), 2.64 (s, 3H), 2.33 (s, 3H), 1.90 (s, 3H); (Yield: 68.7%)

Example 35

4-[7-(4-fluorobenzyloxy)-2,3-dimethyl-pyrrolo[3,2-b]pyridin-1-ylmethyl]-benzoic acid methyl ester hydrochloride $^1$H-NMR (CDCl$_3$) δ8.38 (s, 1H), 8.06 (d, 1H), 7.94 (m, 2H), 7.60 (d, 1H), 7.08 (m, 4H), 6.71 (m, 2H), 5.59 (s, 2H), 5.23 (s, 2H), 3.93 (s, 3H), 2.62 (s, 3H), 2.38 (s, 3H); (Yield: 63.4%)

Example 36

1-(4-tert-butylbenzyl)-7-(4-fluorobenzyloxy)-2,3-dimethyl-1H-pyrrolo[3,2-b]pyridine hydrochloride $^1$H-NMR (CDCl$_3$) δ8.35 (s, 1H), 7.29 (d, 2H), 6.99 (m, 4H), 6.90 (s, 1H), 6.61 (s, 2H), 5.60 (s, 2H), 5.22 (s, 2H), 2.60 (s, 3H), 2.38 (s, 3H), 1.32 (s, 9H); (Yield: 58.4%)

Example 37

7-(4-fluorobenzyloxy)-2,3-dimethyl-1-(naphthalen-2-ylmethyl)-1H-pyrrolo[3,2-b]pyridine hydrochloride $^1$H-NMR (CDCl$_3$) δ8.36 (s, 1H), 7.50 (m, 4H), 7.20 (m, 4H), 7.01 (m, 4H), 5.42 (s, 2H), 5.33 (s, 2H), 2.48 (s, 3H), 2.33 (s, 3H); (Yield: 59.4%)

Example 38

7-(4-fluorobenzyloxy)-2,3-dimethyl-1-(2-vinyloxy-ethyl)-1H-pyrrolo[3,2-b]pyridine hydrochloride $^1$H-NMR (CDCl$_3$) δ8.12 (s, 1H), 7.52 (m, 2H), 7.16 (m, 2H), 6.95 (s, 1H), 5.41 (s, 2H), 5.40 (s, 2H), 4.43 (s, 2H), 3.90 (s, 2H), 2.48 (s, 3H), 2.37 (s, 3H); (Yield: 48.7%)

Example 39

1-(1,3-dioxolan-2-ylmethyl)-7-(4-fluorobenzyloxy)-2,3-dimethyl-1H-pyrrolo[3,2-b]pyridine hydrochloride $^1$H-NMR (CDCl$_3$) δ8.36 (s, 1H), 7.47 (m, 4H), 7.12 (s, 1H), 5.68 (s, 2H), 4.98 (d, 2H), 4.58 (m, 1H), 4.10 (m, 4H), 2.68 (s, 3H), 2.59 (s, 3H); (Yield: 53.2%)

Example 40

1-(3-fluorobenzyl)-7-(4-fluorobenzyloxy)-2,3-dimethyl-1H-pyrrolo[3,2-b]pyridine hydrochloride $^1$H-NMR (CDCl$_3$) δ8.37 (t, 1H), 7.24-6.91 (m, 7H), 6.39 (m, 2H), 5.52 (s, 2H), 5.24 (s, 2H), 2.59 (s, 3H), 2.38 (s, 3H); (Yield: 68.3%)

Example 41

1-(2,5-dimethylbenzyl)-7-(4-fluorobenzyloxy)-2,3-dimethyl-1H-pyrrolo[3,2-b]pyridine hydrochloride $^1$H-NMR (CDCl$_3$) δ8.32 (d, 1H), 7.05 (m, 7H), 5.76 (s, 1H), 5.41 (s, 2H), 5.15 (s, 2H), 2.70 (s, 3H), 2.54 (s, 3H), 2.13 (s, 3H), 1.99 (s, 3H); (Yield: 53.0%)

Example 42

1-(3,5-dimethylisoxazol-4-ylmethyl)-7-(4-fluorobenzyloxy)-2,3-dimethyl-1H-pyrrolo[3,2-b]pyridine hydrochloride $^1$H-NMR (CDCl$_3$) δ8.46 (s, 1H), 7.13 (m, 4H), 6.97 (s, 1H), 5.30 (s, 4H), 2.59 (s, 3H), 2.32 (s, 3H), 1.75 (s, 3H), 1.71 (s, 3H); (Yield: 78.4%)

Example 43

1-(3-chlorobenzyl)-7-(4-fluorobenzyloxy)-2,3-dimethyl-1H-pyrrolo[3,2-b]pyridine hydrochloride $^1$H-NMR (CDCl$_3$) δ8.39 (s, 1H), 7.39 (d, 1H), 7.24 (m, 1H), 7.12 (m, 1H), 6.95 (m, 5H), 6.02 (s, 1H), 5.58 (s, 2H), 5.18 (s, 2H), 2.63 (s, 3H), 2.36 (s, 3H); (Yield: 81.0%)

Example 44

1-(pyridin-2-ylmethyl)-7-(4-fluorobenzyloxy)-2,3-dimethyl-1H-pyrrolo[3,2-b]pyridine hydrochloride $^1$H-NMR (CDCl$_3$) δ8.35 (s, 1H), 7.29 (d, 2H), 6.99 (m, 4H), 6.90 (s, 1H), 6.61 (s, 2H), 5.60 (s, 2H), 5.22 (s, 2H), 2.60 (s, 3H), 2.38 (s, 3H); (Yield: 82.3%)

Example 45

1-(2,3-dihydrobenzo[1,4]dioxin-6-ylmethyl)-7-(4-fluorobenzyloxy)-2,3-dimethyl-1H-pyrrolo[3,2-b]pyridine hydrochloride $^1$H-NMR (CDCl$_3$) δ8.43 (s, 1H), 7.48 (m, 3H), 7.19 (m, 2H), 6.86 (m, 2H), 6.74 (s, 1H), 5.37 (s, 2H), 4.42 (s, 2H), 3.76 (d, 2H), 3.59 (d, 2H), 2.53 (s, 3H), 2.46 (s, 3H); (Yield: 67.0%)

Example 46

1-(3-cyanobenzyl)-7-(4-fluorobenzyloxy)-2,3-dimethyl-1H-pyrrolo[3,2-b]pyridine hydrochloride $^1$H-NMR (CDCl$_3$) δ8.42 (s, 1H), 7.59 (m, 2H), 7.38 (m, 2H), 7.14 (m, 4H), 7.00 (s, 1H), 5.53 (s, 2H), 5.22 (s, 2H), 2.74 (s, 3H), 2.40 (s, 3H); (Yield: 83.2%)

Example 47

1-oxiranylmethyl-7-(4-fluorobenzyloxy)-2,3-dimethyl-1H-pyrrolo[3,2-b]pyridine hydrochloride $^1$H-NMR (CDCl$_3$) δ8.34 (s, 1H), 7.48 (m, 4H), 7.13 (s, 1H), 5.68 (s, 2H), 4.89 (s, 2H), 3.98 (m, 1H), 3.33 (m, 2H), 2.59 (s, 3H), 2.50 (s, 3H); (Yield: 65.4%)

Example 48

1-(pyridin-3-ylmethyl)-7-(4-fluorobenzyloxy)-2,3-dimethyl-1H-pyrrolo[3,2-b]pyridine hydrochloride $^1$H-NMR (CDCl$_3$) δ8.36 (s, 1H), 7.85 (m, 4H), 7.47 (m, 4H), 7.12 (s, 1H), 5.68 (s, 2H), 5.12 (s, 2H), 2.68 (s, 3H), 2.59 (s, 3H); (Yield: 54.0%)

Example 49

1-allyl-7-(4-fluorobenzyloxy)-2,3-dimethyl-1H-pyrrolo[3,2-b]pyridine hydrochloride $^1$H-NMR (CDCl$_3$) δ8.43 (d, 1H), 7.47 (m, 3H), 7.00 (m, 2H), 5.84 (m, 1H), 5.48 (s, 2H), 5.22 (d, 1H), 5.14 (s, 2H), 4.55 (d, 1H), 2.58 (s, 3H), 2.40 (s, 3H); (Yield: 79.0%)

Example 50

7-(4-fluorobenzyloxy)-1-isobutyl-2,3-dimethyl-1H-pyrrolo[3,2-b]pyridine hydrochloride $^1$H-NMR (CDCl$_3$) δ8.34 (d, 1H), 7.25 (m, 5H), 5.68 (s, 2H), 4.85 (d, 2H), 2.56 (s, 3H), 2.33 (s, 3H), 1.78 (m, 1H), 1.58 (d, 6H); (Yield: 86.0%)

Example 51

7-(4-fluorobenzyloxy)-2,3-dimethyl-1-(prop-2-ynyl)-1H-pyrrolo[3,2-b]pyridine hydrochloride $^1$H-NMR (CDCl$_3$) δ8.37 (s, 3H), 7.53 (m, 2H), 7.16 (m, 2H), 6.94 (s, 1H), 5.41 (s, 2H), 5.12 (s, 2H), 2.56 (s, 3H), 2.50 (s, 3H), 2.38 (s, 1H); (Yield: 58.6%)

Example 52

7-(4-fluorobenzyloxy)-1-(3-methoxybenzyl)-2,3-dimethyl-1H-pyrrolo[3,2-b]pyridine hydrochloride $^1$H-NMR (CDCl$_3$) δ8.35 (s, 1H), 7.20 (m, 3H), 7.00 (m, 3H), 6.91 (s, 1H), 6.22 (s, 2H), 5.54 (s, 2H), 5.29 (s, 2H), 3.72 (s, 3H), 2.63 (s, 3H), 2.40 (s, 3H); (Yield: 71.5%)

Example 53

7-(4-fluorobenzyloxy)-1-(3-methylbenzyl)-2,3-dimethyl-1H-pyrrolo[3,2-b]pyridine hydrochloride $^1$H-NMR (CDCl$_3$) δ8.36 (s, 1H), 7.04 (m, 1H), 7.01 (m, 5H), 6.83 (s, 1H), 6.47 (s, 1H), 6.44 (m, 1H), 5.52 (s, 2H), 5.22 (s, 2H), 2.60 (s, 3H), 2.37 (s, 3H), 2.26 (s, 3H); (Yield: 88.5%)

Example 54

1-benzyl-7-(4-fluorobenzyloxy)-2,3-dimethyl-1H-pyrrolo[3,2-b]pyridine hydrochloride $^1$H-NMR (CDCl$_3$) δ8.37 (s, 1H), 7.29 (m, 3H), 7.01 (m, 4H), 6.84 (s, 1H), 6.66 (m, 2H), 5.56 (s, 2H), 5.22 (s, 2H), 2.61 (s, 3H), 2.38 (s, 3H); (Yield: 89.3%)

Example 55

1-cyclobutylmethyl-7-(4-fluorobenzyloxy)-2,3-dimethyl-1H-pyrrolo[3,2-b]pyridine hydrochloride $^1$H-NMR (CDCl$_3$) δ8.37 (s, 1H), 7.50 (m, 2H), 7.18 (m, 3H), 5.37 (s, 2H), 4.28 (s, 2H), 2.54 (m, 1H), 2.55 (s, 3H), 2.45 (s, 3H), 1.79 (m, 3H), 1.57 (m, 3H); (Yield; 78.6%)

Example 56

7-(4-fluorobenzyloxy)-2,3-dimethyl-1-(3-methyl-2-buten-2-yl)-1H-pyrrolo[3,2-b]pyridine hydrochloride $^1$H-NMR (CDCl$_3$) δ8.35 (s, 1H), 7.43 (m, 2H), 7.14 (m, 2H), 6.85 (s, 1H), 5.36 (s, 2H), 5.04 (m, 1H), 4.94 (s, 2H), 2.54 (s, 3H), 2.39 (s, 3H), 1.58 (s, 6H); (Yield: 59.8%)

Example 57

1-[2-(methoxycarbonyl)ethyl]-7-(4-fluorobenzyloxy)-2,3-dimethyl-1H-pyrrolo[3,2-b]pyridine hydrochloride $^1$H-NMR (CDCl$_3$) δ8.36 (s, 1H), 7.48 (m, 2H), 7.12 (m, 2H), 6.93 (s, 1H), 5.39 (s, 2H), 4.51 (s, 2H), 4.23 (s, 2H), 2.55 (s, 3H), 2.45 (s, 3H), 1.95 (s, 3H); (Yield: 67.9%)

Example 58

7-(4-fluorobenzyloxy)-1-(4-methoxybenzyl)-2,3-dimethyl-1H-pyrrolo[3,2-b]pyridine hydrochloride $^1$H-NMR (CDCl$_3$) δ8.36 (s, 1H), 7.11 (s, 2H), 7.01 (m, 2H), 6.80 (m, 3H), 6.61 (d, 2H), 5.49 (s, 2H), 5.25 (s, 2H), 3.79 (s, 3H), 2.59 (s, 3H), 2.38 (s, 3H); (Yield: 78.4%)

Example 59

1-(2-fluorobenzyl)-7-(4-fluorobenzyloxy)-2,3-dimethyl-1H-pyrrolo[3,2-b]pyridine hydrochloride $^1$H-NMR (CDCl$_3$) δ8.43 (s, 1H), 7.53 (m, 2H), 7.27 (m, 1H), 7.05 (m, 4H), 6.23 (m, 2H), 5.61 (s, 2H), 5.30 (s, 2H), 2.63 (s, 3H), 2.49 (s, 3H); (Yield: 86.3%)

Example 60

1-cyclopropylmethyl-7-(4-fluorobenzyloxy)-2,3-dimethyl-1H-pyrrolo[3,2-b]pyridine hydrochloride $^1$H-NMR (CDCl$_3$) δ8.36 (s, 1H), 7.50 (m, 2H), 7.24 (s, 1H), 7.10 (m, 2H), 5.84 (s, 2H), 5.10 (s, 2H), 2.54 (s, 3H), 2.35 (s, 3H), 0.78 (m, 1H), 0.62 (m, 2H), 0.17 (m, 2H); (Yield: 79.6%)

Example 61

7-(4-fluorobenzyloxy)-1-(2-methoxyethyl)-2,3-dimethyl-1H-pyrrolo[3,2-b]pyridine hydrochloride $^1$H-NMR (CDCl$_3$) δ8.38 (s, 1H), 7.46 (m, 2H), 7.18 (m, 2H), 6.91 (s, 1H), 5.36 (s, 2H), 4.44 (s, 2H), 3.51 (s, 2H), 3.19 (s, 3H), 2.54 (s, 3H), 2.43 (s, 3H); (Yield: 69.0%)

Example 62

7-(4-fluorobenzyloxy)-2,3-dimethyl-1-propyl-1H-pyrrolo[3,2-b]pyridine hydrochloride $^1$H-NMR (CDCl$_3$) δ8.36 (s, 1H), 7.48 (m, 2H), 7.17 (m, 2H), 6.89 (s, 1H), 5.34 (s, 2H), 4.17 (t, 2H), 2.54 (s, 3H), 2.40 (s, 3H), 1.66 (m, 2H), 0.72 (t, 3H); (Yield: 78.5%)

Example 63

1-benzyl-7-(4-fluorobenzyloxy)-2,3-dimethyl-1H-pyrrolo[3,2-b]pyridine methanesulfonate The compound prepared in Example 54 (219 mg, 0.58 mmol) was treated with a saturated sodium bicarbonate solution to obtain 1-benzyl-7-(4-fluorobenzyloxy)-2,3-dimethyl-1H-pyrrolo[3,2-b]pyridine (200 mg, 0.55 mmol). Methanesulfonic acid (0.034 ml, 0.55 mmol) was added at room temperature to a solution of 1-benzyl-7-(4-fluorobenzyloxy)-2,3-dimethyl-1H-pyrrolo[3,2-b]pyridine (200 mg, 0.55 mmol) in 10 ml of ethyl acetate. The reaction mixture was stirred for 24 hours at the same temperature. The resulting solid was filtered to give the titled compound as a white solid (Yield: 89.7%).

$^1$H-NMR (CDCl$_3$) δ8.37 (s, 1H), 7.29 (m, 3H), 7.01 (m, 4H), 6.84 (s, 1H), 6.66 (m, 2H), 5.56 (s, 2H), 5.22 (s, 2H), 2.61 (s, 3H), 2.38 (s, 3H)

Examples 64 to 71

The titled compounds of Examples 64 to 71 were prepared, in accordance with the same procedures as in Example 63, using 1-benzyl-7-(4-fluorobenzyloxy)-2,3-dimethyl-1H-pyrrolo[3,2-b]pyridine obtained by treating the compound prepared in Example 54 with a saturated sodium bicarbonate solution; and, benzenesulfonic acid, p-toluenesulfonic acid, nitric acid, sulfuric acid, maleic acid, phosphoric acid, malonic acid, or hydrobromic acid.

Example 64

1-benzyl-7-(4-fluorobenzyloxy)-2,3-dimethyl-1H-pyrrolo[3,2-b]pyridine benzenesulfonate $^1$H-NMR (CDCl$_3$) δ8.67 (s, 1H), 8.01 (s, 2H), 7.38 (s, 3H), 7.26 (m, 4H), 6.98 (m, 3H), 6.87 (d, 1H), 6.65 (s, 2H), 5.55 (s, 2H), 5.21 (s, 2H), 2.44 (s, 3H), 2.36 (s, 3H); (Yield: 95.8%)

Example 65

1-benzyl-7-(4-fluorobenzyloxy)-2,3-dimethyl-1H-pyrrolo[3,2-b]pyridine p-toluenesulfonate $^1$H-NMR (CDCl$_3$) δ8.68 (s, 1H), 7.91 (d, 2H), 7.27 (m, 4H), 7.18 (d, 2H), 6.99 (m, 3H), 6.87 (d, 1H), 6.66 (d, 2H), 5.55 (s, 2H), 5.21 (s, 2H), 2.44 (s, 3H), 2.36 (s, 6H); (Yield: 88.4%)

Example 66

1-benzyl-7-(4-fluorobenzyloxy)-2,3-dimethyl-1H-pyrrolo[3,2-b]pyridine nitrate $^1$H-NMR (CDCl$_3$) δ8.53 (s, 1H), 7.29 (m, 4H), 7.00 (m, 4H), 6.88 (d, 1H), 6.68 (s, 2H), 5.58 (s, 2H), 5.25 (s, 2H), 2.42 (s, 3H), 2.38 (s, 3H); (Yield: 79.8%)

Example 67

1-benzyl-7-(4-fluorobenzyloxy)-2,3-dimethyl-1H-pyrrolo[3,2-b]pyridine sulfate $^1$H-NMR (DMSO-d$_6$) δ8.45 (s, 1H), 7.25 (s, 6H), 7.11 (t, 2H), 6.78 (s, 2H), 5.61 (s, 2H), 5.44 (s, 2H), 2.36 (s, 3H), 2.28 (s, 3H); (Yield: 86.9%)

Example 68

1-benzyl-7-(4-fluorobenzyloxy)-2,3-dimethyl-1H-pyrrolo[3,2-b]pyridine maleate $^1$H-NMR (CDCl$_3$) δ8.62 (d, 1H), 7.28 (m, 4H), 6.99 (m, 3H), 6.84 (d, 1H), 6.67 (s, 2H), 6.38 (s, 2H), 5.57 (s, 2H), 5.22 (s, 2H), 2.44 (s, 3H), 2.38 (s, 3H); (Yield: 95.4%)

Example 69

1-benzyl-7-(4-fluorobenzyloxy)-2,3-dimethyl-1H-pyrrolo[3,2-b]pyridine phosphate $^1$H-NMR (DMSO-d$_6$) δ8.02 (s, 1H), 7.09 (m, 5H), 6.95 (m, 2H), 6.70 (s, 1H), 6.64 (s, 2H), 5.43 (s, 2H), 5.09 (s, 2H), 2.14 (s, 3H), 2.08 (s, 3H); (Yield: 85.8%)

Example 70

1-benzyl-7-(4-fluorobenzyloxy)-2,3-dimethyl-1H-pyrrolo[3,2-b]pyridine malonate $^1$H-NMR (DMSO-d$_6$) δ8.58 (d, 1H), 7.28 (m, 4H), 7.00 (m, 3H), 6.82 (d, 1H), 6.68 (s, 2H), 5.58 (s, 2H), 5.22 (s, 2H), 3.32 (s, 2H), 2.44 (s, 3H), 2.38 (s, 3H); (Yield: 91.2%)

Example 71

1-benzyl-7-(4-fluorobenzyloxy)-2,3-dimethyl-1H-pyrrolo[3,2-b]pyridine hydrobromide $^1$H-NMR (CDCl$_3$) δ8.38 (s, 1H), 7.29 (m, 4H), 7.00 (m, 3H), 6.92 (d, 1H), 6.66 (s, 2H), 5.56 (s, 2H), 5.25 (s, 2H), 2.60 (s, 3H), 2.38 (s, 3H); (Yield: 79.8%)

Example 72

1-allyl-7-(4-chlorobenzyloxy)-2,3-dimethyl-1H-pyrrolo[3,2-b]pyridine hydrochloride Step 1: 4-(4-chlorobenzyloxy)-3-nitropyridine In accordance with the same procedures as in Preparation 2, except for using 4-chloro-3-nitropyridine prepared in Step 1 of Preparation 1 and 4-chlorobenzyl alcohol, the titled compound was obtained as a white solid. (Yield: 78.0%)

$^1$H-NMR (CDCl$_3$) δ9.04 (s, 1H), 8.62 (d, 1H), 7.40 (m, 4H), 7.04 (d, 1H), 5.28 (d, 1H)

Step 2: 7-(4-chlorobenzyloxy)-2,3-dimethyl-1H-pyrrolo[3,2-b]pyridine

In accordance with the same procedures as in Step 1 of Example 33, except for using 4-(4-chlorobenzyloxy)-3-nitropyridine prepared in Step 1, the titled compound was obtained as a white solid. (Yield: 23.8%)

$^1$H-NMR (CDCl$_3$) δ8.28 (d, 1H), 8.02 (s, 1H), 7.38 (m, 4H), 6.58 (d, 1H), 5.19 (s, 2H), 2.40 (s, 3H), 2.30 (s, 3H)

Step 3: 1-allyl-7-(4-chlorobenzyloxy)-2,3-dimethyl-1H-pyrrolo[3,2-b]pyridine hydrochloride In accordance with the same procedures as in Step 2 of Example 33, except for using 7-(4-chlorobenzyloxy)-2,3-dimethyl-1H-pyrrolo[3,2-b]pyridine prepared in Step 2 and allyl bromide, the titled compound was obtained as a white solid. (Yield: 75.3%

$^1$H-NMR (CDCl$_3$) δ8.35 (d, 1H), 7.44 (d, 2H), 7.38 (d, 2H), 6.85 (d, 1H), 5.87 (m, 1H), 5.33 (s, 2H), 5.14 (d, 1H), 4.93 (s, 2H), 4.53 (d, 1H), 2.56 (s, 3H), 2.38 (s, 3H)

Examples 73 to 97

The titled compounds of Examples 73 to 97 were prepared, in accordance with the same procedures as in Step 2 of Example 33, using 7-(4-chlorobenzyloxy)-2,3-dimethyl-1H-pyrrolo[3,2-b]pyridine prepared in Step 2 of Example 72; and, benzyl bromide, bromomethyl methyl ether, 2-cyanobenzyl bromide, 2-chlorobenzyl chloride, bromoacetonitrile, 4-trifluoromethylbenzyl bromide, 4-tert-butylbenzyl chloride, 4-chloromethylpyridine, 5-chloromethyl-2-oxazolidinone, 2,5-dimethylbenzyl chloride, methyl bromoacetate, 4-bromo-2-methyl-2-butene, 2-bromoethyl acetate, 2-bromoethyl methyl ether, 2-bromomethyl-1,3-dioxolane, 4-chlorobenzyl bromide, 2-fluorobenzyl bromide, iodoethane, 4-fluorobenzyl chloride, 3-methoxybenzyl chloride, 4-fluorobenzyl chloride, methyl-4-(bromomethyl)benzoate, 3-methylbenzyl chloride, 4-methylbenzyl chloride, or (bromomethyl)cyclopropane.

Example 73

1-benzyl-7-(4-chlorobenzyloxy)-2,3-dimethyl-1H-pyrrolo[3,2-b]pyridine hydrochloride $^1$H-NMR (CDCl$_3$) δ8.36 (d, 1H), 7.30 (m, 5H), 6.98 (d, 2H), 6.84 (d, 1H), 6.68 (d, 2H), 5.57 (s, 2H), 5.23 (s, 2H), 2.60 (s, 3H), 2.38 (s, 3H); (Yield: 69.5%)

Example 74

7-(4-chlorobenzyloxy)-1-methoxymethyl-2,3-dimethyl-1H-pyrrolo[3,2-b]pyridine hydrochloride $^1$H-NMR (CDCl$_3$) δ8.36 (d, 1H), 7.45 (m, 4H), 6.97 (d, 1H), 5.61 (s, 2H), 5.40 (s, 2H), 3.17 (s, 3H), 2.55 (s, 3H), 2.49 (s, 3H); (Yield: 67.3%)

Example 75

1-(2-cyanobenzyl)-7-(4-chlorobenzyloxy)-2,3-dimethyl-1H-pyrrolo[3,2-b]pyridine hydrochloride $^1$H-NMR (CDCl$_3$) δ8.40 (d, 1H), 7.64 (d, 1H), 7.42 (m, 3H), 6.96 (m, 3H), 6.32 (s, 1H), 5.75 (s, 2H), 5.23 (s, 2H), 2.62 (s, 3H), 2.39 (s, 3H); (Yield: 75.4%)

Example 76

1-(2-chlorobenzyl)-7-(4-chlorobenzyloxy)-2,3-dimethyl-1H-pyrrolo[3,2-b]pyridine hydrochloride $^1$H-NMR (CDCl$_3$) δ8.37 (s, 1H), 7.41 (d, 2H), 7.25 (m, 3H), 7.14 (m, 1H), 6.90 (m, 3H), 5.59 (s, 2H), 5.18 (s, 2H), 2.63 (s, 3H), 2.36 (s, 3H); (Yield: 68.4%)

Example 77

1-cyanomethyl-7-(4-chlorobenzyloxy)-2,3-dimethyl-1H-pyrrolo[3,2-b]pyridine hydrochloride $^1$H-NMR (CDCl$_3$) δ8.36 (s, 1H), 7.48 (m, 4H), 7.03 (s, 1H), 5.44 (s, 2H), 5.26 (s, 2H), 2.53 (s, 6H); (Yield: 54.1%)

Example 78

7-(4-chlorobenzyloxy)-2,3-dimethyl-1-(4-trifluoromethylbenzyl)-1H-pyrrolo[3,2-b]pyridine hydrochloride $^1$H-NMR (CDCl$_3$) δ8.38 (s, 1H), 7.53 (d, 2H), 7.29 (d, 2H), 6.99 (d, 2H), 6.88 (s, 1H), 6.76 (d, 2H), 5.59 (s, 2H), 5.20 (s, 2H), 2.61 (s, 3H), 2.38 (s, 3H); (Yield: 68.7%)

Example 79

1-(4-tert-butylbenzyl)-7-(4-chlorobenzyloxy)-2,3-dimethyl-1H-pyrrolo[3,2-b]pyridine hydrochloride $^1$H-NMR (CDCl$_3$) δ8.34 (s, 1H), 7.28 (m, 4H), 6.98 (d, 2H), 6.81 (s, 1H), 6.62 (d, 2H), 5.53 (s, 2H), 5.23 (s, 2H), 2.59 (s, 3H), 2.38 (s, 3H), 1.30 (s, 9H); (Yield: 58.9%)

Example 80

7-(4-chlorobenzyloxy)-2,3-dimethyl-1-(pyridin-4-ylmethyl)-1H-pyrrolo[3,2-b]pyridine hydrochloride $^1$H-NMR (CDCl$_3$) δ8.51 (d, 1H), 8.41 (s, 1H), 7.34 (d, 2H), 7.01 (d, 2H), 6.86 (s, 1H), 6.58 (s, 2H), 5.53 (s, 2H), 5.16 (s, 2H), 2.62 (s, 3H), 2.38 (s, 3H); (Yield: 68.0%)

Example 81

5-[7-(4-chlorobenzyloxy)-2,3-dimethyl-pyrrolo[3,2-b]pyridin-1-ylmethyl]-oxazolidin-2-one hydrochloride $^1$H-NMR (CDCl$_3$) δ9.27 (s, 1H), 8.32 (s, 1H), 7.52 (m, 3H), 6.87 (s, 1H), 5.45 (s, 2H), 5.02 (s, 1H), 4.86 (s, 1H), 3.77 (m, 2H), 3.63 (m, 1H), 2.50 (s, 6H); (Yield: 61.1%)

Example 82

7-(4-chlorobenzyloxy)-1-(2,5-dimethylbenzyl)-2,3-dimethyl-1H-pyrrolo[3,2-b]pyridine hydrochloride $^1$H-NMR (CDCl$_3$) δ8.36 (s, 1H), 7.21 (m, 3H), 7.08 (m, 2H), 6.84 (d, 2H), 5.67 (s, 1H), 5.41 (s, 2H), 5.14 (s, 2H), 2.63 (s, 3H), 2.35 (s, 3H), 2.17 (s, 3H), 2.01 (s, 3H); (Yield: 59.8%)

Example 83

[7-(4-chlorobenzyloxy)-2,3-dimethyl-pyrrolo[3,2-b]pyridin-1-yl]acetic acid methyl ester hydrochloride $^1$H-NMR (CDCl$_3$) δ8.36 (s, 1H), 7.45 (d, 2H), 7.36 (d, 2H), 6.88 (s, 1H), 5.32 (s, 2H), 5.03 (s, 2H), 3.65 (s, 3H), 2.56 (s, 3H), 2.36 (s, 3H); (Yield: 63.3%)

Example 84

7-(4-chlorobenzyloxy)-2,3-dimethyl-1-(3-methylbut-2-enyl)-1H-pyrrolo[3,2-b]pyridine hydrochloride $^1$H-NMR (CDCl$_3$) δ8.33 (d, 1H), 7.41 (m, 4H), 6.85 (d, 1H), 5.39 (s, 2H), 5.05 (m, 1H), 4.95 (d, 2H), 2.54 (s, 3H), 2.32 (s, 3H), 1.41 (s, 6H); (Yield: 58.6%)

Example 85

1-(2-acetoxyethyl)-7-(4-chlorobenzyloxy)-2,3-dimethyl-1H-pyrrolo[3,2-b]pyridine hydrochloride $^1$H-NMR (CDCl$_3$) δ8.33 (d, 1H), 7.45 (m, 4H), 6.92 (d, 1H), 5.38 (s, 2H), 4.59 (d, 2H), 4.25 (d, 2H), 2.62 (s, 3H), 2.45 (s, 3H), 2.06 (s, 3H); (Yield: 77.6%)

Example 86

7-(4-chlorobenzyloxy)-1-(2-methoxyethyl)-2,3-dimethyl-1H-pyrrolo[3,2-b]pyridine hydrochloride $^1$H-NMR (CDCl$_3$) δ8.38 (d, 1H), 7.59 (m, 4H), 6.93 (d, 1H), 5.34 (s, 2H), 4.40 (s, 2H), 3.47 (s, 2H), 3.21 (s, 3H), 2.55 (s, 3H), 2.46 (s, 3H); (Yield: 77.0%)

Example 87

7-(4-chlorobenzyloxy)-1-(1,3-dioxolan-2-ylmethyl)-2,3-dimethyl-1H-pyrrolo[3,2-b]pyridine hydrochloride $^1$H-NMR (CDCl$_3$) δ 8.28 (d, 1H), 7.44 (m, 4H), 6.86 (d, 1H), 5.38 (s, 2H), 5.09 (m, 1H), 4.53 (s, 2H), 3.76 (s, 2H), 3.60 (s, 2H), 2.58 (s, 3H), 2.46 (s, 3H); (Yield: 58.4%)

Example 88

7-(4-chlorobenzyloxy)-1-(4-chlorobenzyl)-2,3-dimethyl-1H-pyrrolo[3,2-b]pyridine hydrochloride $^1$H-NMR (CDCl$_3$) δ 8.36 (s, 1H), 7.30 (m, 4H), 7.04 (d, 2H), 6.88 (s, 1H), 6.60 (d, 2H), 5.51 (s, 2H), 5.23 (s, 2H), 2.59 (s, 3H), 2.37 (s, 3H); (Yield: 85.3%)

Example 89

7-(4-chlorobenzyloxy)-1-(2-fluorobenzyl)-2,3-dimethyl-1H-pyrrolo[3,2-b]pyridine hydrochloride $^1$H-NMR (CDCl$_3$) δ 8.38 (s, 1H), 7.28 (m, 3H), 6.99 (m, 4H), 6.73 (s, 1H), 6.13 (s, 1H), 5.62 (s, 2H), 5.30 (s, 2H), 2.61 (s, 3H), 2.38 (s, 3H); (Yield: 86.0%)

Example 90

7-(4-chlorobenzyloxy)-1-ethyl-2,3-dimethyl-1H-pyrrolo[3,2-b]pyridine hydrochloride $^1$H-NMR (CDCl$_3$) δ 8.33 (s, 1H), 7.44 (m, 4H), 6.89 (s, 1H), 5.38 (s, 2H), 4.35 (m, 2H), 2.53 (s, 3H), 2.42 (s, 3H), 1.29 (t, 3H); (Yield: 88.3%)

Example 91

7-(4-chlorobenzyloxy)-1-(4-fluorobenzyl)-2,3-dimethyl-1H-pyrrolo[3,2-b]pyridine hydrochloride $^1$H-NMR (CDCl$_3$) δ 8.36 (s, 1H), 7.37 (d, 2H), 7.06 (d, 2H), 6.99 (d, 2H), 6.87 (s, 1H), 6.64 (s, 2H), 5.52 (s, 2H), 5.24 (s, 2H), 2.59 (s, 3H), 2.38 (s, 3H); (Yield: 81.1%)

Example 92

7-(4-chlorobenzyloxy)-1-(3-methoxybenzyl)-2,3-dimethyl-1H-pyrrolo[3,2-b]pyridine hydrochloride $^1$H-NMR (CDCl$_3$) δ 8.35 (s, 1H), 7.39 (m, 1H), 7.27 (s, 1H), 7.18 (t, 1H), 7.00 (d, 2H), 6.82 (d, 2H), 6.22 (d, 2H), 5.52 (s, 2H), 5.22 (s, 2H), 3.77 (s, 3H), 2.59 (s, 3H), 2.37 (s, 3H); (Yield: 79.8%)

Example 93

7-(4-chlorobenzyloxy)-1-(3-fluorobenzyl)-2,3-dimethyl-1H-pyrrolo[3,2-b]pyridine hydrochloride $^1$H-NMR (CDCl$_3$) δ 8.37 (s, 1H), 7.29 (m, 3H), 7.02 (m, 3H), 6.87 (s, 1H), 6.40 (t, 2H), 5.53 (s, 2H), 5.22 (s, 2H), 2.60 (s, 3H), 2.38 (s, 3H); (Yield: 80.1%)

Example 94

7-(4-chlorobenzyloxy)-1-(4-methoxycarbonylbenzyl)-2,3-dimethyl-1H-pyrrolo[3,2-b]pyridine hydrochloride $^1$H-NMR (CDCl$_3$) δ 8.38 (s, 1H), 7.94 (d, 2H), 7.28 (d, 2H), 7.00 (d, 2H), 6.85 (s, 1H), 6.70 (d, 2H), 5.59 (s, 2H), 5.19 (s, 2H), 3.93 (s, 3H), 2.61 (s, 3H), 2.37 (s, 3H); (Yield: 78.9%)

Example 95

7-(4-chlorobenzyloxy)-1-(3-methylbenzyl)-2,3-dimethyl-1H-pyrrolo[3,2-b]pyridine hydrochloride $^1$H-NMR (CDCl$_3$) δ 8.35 (s, 1H), 7.27 (d, 2H), 7.18 (t, 1H), 7.10 (d, 1H), 6.97 (d, 2H), 6.82 (s, 1H), 6.48 (m, 2H), 5.53 (s, 2H), 5.22 (s, 2H), 2.60 (s, 3H), 2.37 (s, 3H), 2.22 (s, 3H); (Yield: 75.3%)

Example 96

7-(4-chlorobenzyloxy)-1-(4-methylbenzyl)-2,3-dimethyl-1H-pyrrolo[3,2-b]pyridine hydrochloride $^1$H-NMR (CDCl$_3$) δ 8.35 (s, 1H), 7.27 (d, 2H), 7.08 (d, 2H), 7.01 (d, 2H), 6.81 (s, 1H), 6.56 (d, 2H), 5.52 (s, 2H), 5.23 (s, 2H), 2.59 (s, 3H), 2.37 (s, 3H), 2.34 (s, 3H); (Yield: 78.8%)

Example 97

7-(4-chlorobenzyloxy)-1-cyclopropylmethyl-2,3-dimethyl-1H-pyrrolo[3,2-b]pyridine hydrochloride $^1$H-NMR (CDCl$_3$) δ 8.34 (d, 1H), 7.44 (m, 4H), 6.89 (d, 1H), 5.36 (s, 2H), 4.22 (d, 2H), 2.55 (s, 3H), 2.44 (s, 3H), 1.10 (m, 1H), 0.48 (d, 2H), 0.20 (d, 2H); (Yield: 88.1%)

Example 98

1-allyl-7-(benzo[1,3]dioxol-5-ylmethoxy)-2,3-dimethyl-1H-pyrrolo[3,2-b]pyridine hydrochloride Step 1:
4-(benzo[1,3]dioxol-5-ylmethoxy)-3-nitropyridine In accordance with the same procedures as in Preparation 2, except for using 4-chloro-3-nitropyridine (3.0 g, 18.92 mmol) prepared in Step 1 of Preparation 1 and piperonyl alcohol (3.45 ml, 18.92 mmol), the titled compound was obtained as a yellow solid. (3.08 g, 88.6%)

$^1$H-NMR (CDCl$_3$) δ 9.02 (s, 1H), 8.60 (d, 1H), 7.06 (d, 1H), 6.91 (t, 2H), 6.84 (d, 1H), 5.99 (s, 2H), 5.21 (s, 2H)

Step 2: 7-(benzo[1,3]dioxol-5-ylmethoxy)-2,3-dimethyl-1H-pyrrolo[3,2-b]pyridine

In accordance with the same procedures as in Step 1 of Example 33, except for using 4-(benzo[1,3]dioxol-5-ylmethoxy)-3-nitropyridine prepared in Step 1, the titled compound was obtained as a white solid. (Yield: 28.9%)

$^1$H-NMR (CDCl$_3$) δ 8.28 (d, 1H), 7.94 (s, 1H), 6.94 (m, 2H), 6.82 (d, 1H), 6.60 (d, 1H), 5.99 (s, 2H), 5.11 (s, 2H), 2.39 (s, 3H), 2.21 (s, 3H)

Step 3: 1-allyl-7-(benzo[1,3]dioxol-5-ylmethoxy)-2, 3-dimethyl-1H-pyrrolo[3,2-b]pyridine hydrochloride In accordance with the same procedures as in Step 2 of Example 33, except for using 7-(benzo[1,3]dioxol-5-ylmethoxy)-2,3-dimethyl-1H-pyrrolo[3,2-b]pyridine prepared in Step 2 and allyl bromide, the titled compound was obtained as a white solid. (Yield: 53.8%)

$^1$H-NMR (CDCl$_3$) δ8.33 (s, 1H), 6.86 (m, 4H), 6.03 (s, 2H), 5.90 (m, 1H), 5.27 (s, 2H), 5.15 (d, 1H), 4.96 (s, 2H), 4.56 (d, 1H), 2.56 (s, 3H), 2.39 (s, 3H)

Examples 99 to 121

The titled compounds of Examples 99 to 121 were prepared, in accordance with the same procedures as in Step 2 of Example 33, using 7-(benzo[1,3]dioxol-5-ylmethoxy)-2,3-dimethyl-1H-pyrrolo[3,2-b]pyridine prepared in Step 2 of Example 98; and, 2-bromoethyl methyl ether, 2-bromomethyl-1,3-dioxolane, 2-fluorobenzyl chloride, 4-tert-butylbenzyl chloride, methyl bromoacetate, 4-chloromethyl-3,5-dimethylisoxazole, 5-chloromethyl-2-oxazolidinone, 2-chlorobenzyl chloride, 4-trifluoromethylbenzyl chloride, 2-bromoethanol, bromomethyl methyl ether, 2,5-dimethylbenzyl chloride, 4-methoxycarbonylbenzyl chloride, 4-bromo-2-methyl-2-butene, 3-methylbenzyl chloride, 4-methylbenzyl chloride, benzyl bromide, 3-fluorobenzyl bromide, iodoethane, 4-fluorobenzyl bromide, 3-methoxybenzyl bromide, 1-bromo-2-methylpropane, or (bromomethyl)cyclopropane.

Example 99

7-(benzo[1,3]dioxol-5-ylmethoxy)-1-(2-methoxyethyl)-2,3-dimethyl-1H-pyrrolo[3,2-b]pyridine hydrochloride $^1$H-NMR (CDCl$_3$) δ8.32 (s, 1H), 6.87 (m, 4H), 6.03 (s, 2H), 5.28 (s, 2H), 4.46 (s, 2H), 3.55 (s, 2H), 3.21 (s, 3H), 2.53 (s, 3H), 2.40 (s, 3H); (Yield: 59.6%)

Example 100

7-(benzo[1,3]dioxol-5-ylmethoxy)-1-([1,3]-dioxolan-2-ylmethyl)-2,3-dimethyl-1H-pyrrolo[3,2-b] pyridine hydrochloride $^1$H-NMR (CDCl$_3$) δ8.34 (s, 1H), 6.93 (m, 4H), 6.01 (s, 2H), 5.29 (d, 2H), 5.13 (m, 1H), 4.55 (s, 2H), 3.78 (d, 2H), 3.60 (d, 2H), 2.53 (s, 3H), 2.32 (s, 3H); (Yield: 61.4%)

Example 101

7-(benzo[1,3]dioxol-5-ylmethoxy)-1-(2-fluorobenzyl)-2,3-dimethyl-1H-pyrrolo[3,2-b]pyridine hydrochloride $^1$H-NMR (CDCl$_3$) δ8.34 (m, 1H), 7.07 (m, 3H), 6.82 (m, 1H), 6.73 (d, 1H), 6.61 (d, 1H), 6.39 (s, 1H), 6.221 (m, 1H), 5.99 (s, 2H), 5.61 (s, 1H), 5.15 (s, 2H), 2.60 (s, 3H), 2.29 (s, 3H); (Yield: 58.8%)

Example 102

7-(benzo[1,3]dioxol-5-ylmethoxy)-1-(4-tert-butylbenzyl)-2,3-dimethyl-1H-pyrrolo[3,2-b]pyridine hydrochloride $^1$H-NMR (CDCl$_3$) δ8.32 (s, 1H), 7.30 (m, 2H), 6.79 (m, 2H), 6.64 (m, 3H), 6.43 (s, 1H), 5.99 (s, 2H), 5.53 (s, 2H), 5.15 (s, 2H), 2.58 (s, 3H), 2.38 (s, 3H), 1.29 (s, 9H); (Yield: 83.0%)

Example 103

7-(benzo[1,3]dioxol-5-ylmethoxy)-1-methoxycarbonylmethyl-2,3-dimethyl-1H-pyrrolo[3,2-b]pyridine hydrochloride $^1$H-NMR (CDCl$_3$) δ8.34 (s, 1H), 6.95 (m, 4H), 6.03 (s, 2H), 5.25 (s, 2H), 5.05 (s, 2H), 3.69 (s, 3H), 2.55 (s, 3H), 2.44 (s, 3H); (Yield: 68.1%)

Example 104

7-(benzo[1,3]dioxol-5-ylmethoxy)-1-(3,5-dimethyl-isoxazol-4-ylmethyl)-2,3-dimethyl-1H-pyrrolo[3,2-b]pyridine hydrochloride $^1$H-NMR (CDCl$_3$) δ8.38 (s, 1H), 6.95 (m, 3H), 6.71 (s, 1H), 6.00 (s, 2H), 5.34 (s, 2H), 5.24 (s, 2H), 2.56 (s, 3H), 2.35 (s, 3H), 1.81 (s, 3H), 1.64 (s, 3H); (Yield: 74.0%)

Example 105

7-(benzo[1,3]dioxol-5-ylmethoxy)-1-(2-oxazolidinon-5-ylmethyl)-2,3-dimethyl-1H-pyrrolo[3,2-b] pyridine hydrochloride $^1$H-NMR (CDCl$_3$) δ8.35 (s, 1H), 6.93 (m, 4H), 6.01 (s, 2H), 5.28 (s, 2H), 4.89 (s, 2H), 3.84 (m, 2H), 3.57 (m, 1H), 2.51 (s, 3H), 2.48 (s, 3H); (Yield: 65.4%)

Example 106

7-(benzo[1,3]dioxol-5-ylmethoxy)-1-(2-chlorobenzyl)-2,3-dimethyl-1H-pyrrolo[3,2-b]pyridine hydrochloride $^1$H-NMR (CDCl$_3$) δ8.36 (d, 1H), 7.40 (d, 1H), 6.93 (m, 1H), 6.85 (m, 3H), 6.71 (d, 1H), 6.54 (m, 1H), 6.24 (s, 1H), 5.99 (s, 2H), 5.58 (s, 2H), 5.08 (s, 2H), 2.62 (s, 3H), 2.36 (s, 3H); (Yield: 73.2%)

Example 107

7-(benzo[1,3]dioxol-5-ylmethoxy)-2,3-dimethyl-1-(4-trifluoromethylbenzyl)-1H-pyrrolo[3,2-b]pyridine hydrochloride $^1$H-NMR (CDCl$_3$) δ8.37 (d, 1H), 7.52 (d, 2H), 6.77 (m, 4H), 6.57 (d, 1H), 6.44 (s, 1H), 6.00 (s, 2H), 5.60 (s, 2H), 5.12 (s, 2H), 2.61 (s, 3H), 2.39 (s, 3H); (Yield: 83.5%)

Example 108

7-(benzo[1,3]dioxol-5-ylmethoxy)-1-(2-hydroxyethyl)-2,3-dimethyl-1H-pyrrolo[3,2-b]pyridine hydrochloride $^1$H-NMR (CDCl$_3$) δ8.33 (d, 1H), 7.03 (m, 2H), 6.89 (m, 2H), 6.03 (s, 2H), 5.33 (t, 2H), 4.44 (t, 2H), 3.87 (m, 2H), 2.53 (s, 3H), 2.49 (s, 3H); (Yield: 46.5%)

Example 109

7-(benzo[1,3]dioxol-5-ylmethoxy)-1-methoxymethyl-2,3-dimethyl-1H-pyrrolo[3,2-b]pyridine hydrochloride $^1$H-NMR (CDCl$_3$) δ8.35 (d, 1H), 6.95 (m, 2H), 6.88 (m, 2H), 6.04 (s, 2H), 5.62 (s, 2H), 5.36 (s, 2H), 3.19 (s, 3H), 2.55 (s, 3H), 2.48 (s, 3H); (Yield: 79.5%)

Example 110

7-(benzo[1,3]dioxol-5-ylmethoxy)-1-(2,5-dimethylbenzyl)-2,3-dimethyl-1H-pyrrolo[3,2-b]pyridine hydrochloride $^1$H-NMR (CDCl$_3$) δ8.35 (s, 1H), 6.94 (m, 2H), 6.69 (m, 1H), 6.52 (s, 1H), 6.21 (s, 1H), 6.01 (s, 1H), 5.99 (s, 2H), 5.65 (s, 1H), 5.30 (s, 2H), 5.21 (s, 2H), 5.06 (s, 2H), 2.63 (s, 3H), 2.31 (s, 3H), 2.11 (s, 3H), 2.05 (s, 3H); (Yield: 63.5%)

Example 111

7-(benzo[1,3]dioxol-5-ylmethoxy)-1-(4-methoxycarbonylbenzyl)-2,3-dimethyl-1H-pyrrolo[3,2-b]pyridine hydrochloride $^1$H-NMR (CDCl$_3$) δ8.33 (s, 1H), 7.93 (s, 1H), 6.95 (m, 3H), 6.65 (m, 3H), 6.38 (s, 1H), 5.99 (s, 2H), 5.61 (s, 2H), 5.13 (s, 2H), 3.91 (s, 3H), 2.51 (s, 3H), 2.39 (s, 3H); (Yield: 65.0%)

Example 112

7-(benzo[1,3]dioxol-5-ylmethoxy)-1-(3-methylbut-2-enyl)-2,3-dimethyl-1H-pyrrolo[3,2-b]pyridine hydrochloride $^1$H-NMR (CDCl$_3$) δ8.29 (s, 1H), 6.88 (m, 5H), 6.01 (s, 2H), 5.29 (s, 2H), 5.04 (t, 1H), 4.96 (d, 2H), 2.53 (s, 3H), 2.39 (s, 3H), 1.70 (s, 3H), 1.62 (s, 3H); (Yield: 74.1%)

Example 113

7-(benzo[1,3]dioxol-5-ylmethoxy)-2,3-dimethyl-1-(3-methylbenzyl)-1H-pyrrolo[3,2-b]pyridine hydrochloride $^1$H-NMR (CDCl$_3$) δ8.33 (d, 1H), 7.16 (t, 1H), 7.09 (d, 1H), 6.78 (m, 2H), 6.64 (d, 1H), 6.44 (m, 3H), 5.99 (s, 2H), 5.54 (s, 2H), 5.16 (s, 2H), 2.60 (s, 3H), 2.38 (s, 3H), 2.27 (s, 3H); (Yield: 66.8%)

Example 114

7-(benzo[1,3]dioxol-5-ylmethoxy)-1-(4-methylbenzyl)-2,3-dimethyl-1H-pyrrolo[3,2-b]pyridine hydrochloride $^1$H-NMR (CDCl$_3$) δ8.33 (d, 1H), 7.08 (d, 2H), 6.88 (m, 2H), 6.63 (m, 3H), 6.42 (s, 1H), 5.99 (s, 2H), 5.52 (s, 2H), 5.16 (s, 2H), 2.58 (s, 3H), 2.47 (s, 3H), 2.32 (s, 3H); (Yield: 66.0%)

Example 115

7-(benzo[1,3]dioxol-5-ylmethoxy)-1-benzyl-2,3-dimethyl-1H-pyrrolo[3,2-b]pyridine hydrochloride $^1$H-NMR (CDCl$_3$) δ8.33 (s, 1H), 7.28 (m, 3H), 6.81 (s, 1H), 6.72 (m, 3H), 6.60 (d, 1H), 6.43 (s, 1H), 5.99 (s, 2H), 5.57 (s, 2H), 5.15 (s, 2H), 2.59 (s, 3H), 2.38 (s, 3H); (Yield: 70.5%)

Example 116

7-(benzo[1,3]dioxol-5-ylmethoxy)-1-(3-fluorobenzyl)-2,3-dimethyl-1H-pyrrolo[3,2-b]pyridine hydrochloride $^1$H-NMR (CDCl$_3$) δ8.37 (s, 1H), 6.99 (t, 2H), 6.88 (m, 2H), 6.65 (s, 1H), 6.41 (m, 3H), 6.01 (s, 2H), 5.53 (s, 2H), 5.14 (s, 2H), 2.60 (s, 3H), 2.31 (s, 3H); (Yield: 69.8%)

Example 117

7-(benzo[1,3]dioxol-5-ylmethoxy)-1-ethyl-2,3-dimethyl-1H-pyrrolo[3,2-b]pyridine hydrochloride $^1$H-NMR (CDCl$_3$) δ8.32 (d, 1H), 6.87 (m, 5H), 6.03 (s, 2H), 5.29 (s, 2H), 4.35 (m, 2H), 2.53 (s, 3H), 2.42 (s, 3H), 1.30 (t, 3H); (Yield: 73.3%)

Example 118

7-(benzo[1,3]dioxol-5-ylmethoxy)-1-(4-fluorobenzyl)-2,3-dimethyl-1H-pyrrolo[3,2-b]pyridine hydrochloride $^1$H-NMR (CDCl$_3$) δ8.34 (d, 1H), 7.04 (m, 3H), 6.87 (m, 1H), 6.76 (m, 3H), 6.55 (s, 1H), 6.00 (s, 2H), 5.52 (s, 2H), 5.16 (s, 2H), 2.59 (s, 3H), 2.38 (s, 3H); (Yield: 72.1%)

Example 119

7-(benzo[1,3]dioxol-5-ylmethoxy)-1-(3-methoxybenzyl)-2,3-dimethyl-1H-pyrrolo[3,2-b]pyridine hydrochloride $^1$H-NMR (CDCl$_3$) δ8.33 (d, 1H), 6.91 (m, 3H), 6.65 (m, 2H), 6.45 (s, 1H), 6.24 (m, 2H), 6.02 (s, 2H), 5.40 (s, 2H), 5.13 (s, 2H), 3.72 (s, 3H), 2.62 (s, 3H), 2.36 (s, 3H); (Yield: 73.2%)

Example 120

7-(benzo[1,3]dioxol-5-ylmethoxy)-1-isobutyl-2,3-dimethyl-1H-pyrrolo[3,2-b]pyridine hydrochloride $^1$H-NMR (CDCl$_3$) δ8.41 (d, 1H), 6.93 (m, 4H), 6.03 (s, 2H), 5.25 (s, 2H), 4.03 (s, 2H), 2.63 (s, 3H), 2.40 (s, 3H), 1.99 (m, 1H), 0.67 (s, 6H); (Yield: 80.3%)

Example 121

7-(benzo[1,3]dioxol-5-ylmethoxy)-1-cyclopropylmethyl-2,3-dimethyl-1H-pyrrolo[3,2-b]pyridine hydrochloride $^1$H-NMR (CDCl$_3$) δ8.34 (s, 1H), 6.93 (s, 2H), 6.87 (d, 2H), 6.04 (s, 2H), 5.28 (s, 2H), 4.23 (d, 2H), 2.55 (s, 3H), 2.44 (s, 3H), 1.11 (m, 1H), 0.49 (d, 2H), 0.22 (d, 2H); (Yield: 72.5%)

Example 122

7-(4-fluorobenzyloxy)-1-(2-methoxyethyl)-2,3-dimethyl-1H-pyrrolo[3,2-b]pyridine

The compound prepared in Example 61 (2.1 g, 6.05 mmol) was treated with a saturated sodium bicarbonate solution to obtain the titled compound as a white solid. (Yield: 99.4%)

$^1$H-NMR (CDCl$_3$) δ8.34 (d, 1H), 7.47 (s, 2H), 7.16 (t, 2H), 6.91 (d, 1H), 5.39 (s, 2H), 4.44 (s, 2H), 3.51 (s, 2H), 3.19 (s, 3H), 2.52 (s, 3H), 2.43 (s, 3H)

Example 123

7-(4-fluorobenzyloxy)-1-(2-methoxyethyl)-2,3-dimethyl-1H-pyrrolo[3,2-b]pyridine methanesulfonate 0.039 ml of Methanesulfonic acid was added at room temperature to a solution of 7-(4-fluorobenzyloxy)-1-(2-methoxyethyl)-2,3-dimethyl-1H-pyrrolo[3,2-b]pyridine (200 mg, 0.609 mmol) prepared in Example 122 in 10 ml of ethyl acetate and then stirred for 24 hours at the same temperature. The resulting solid was filtered to give the titled compound as a white solid. (Yield: 85.1%)

$^1$H-NMR (DMSO-d$_6$) δ8.48 (s, 1H), 7.64 (s, 2H), 7.33 (m, 3H), 5.55 (s, 2H), 4.47 (s, 2H), 3.52 (s, 2H), 3.11 (s, 3H), 2.43 (s, 3H), 2.32 (s, 3H), 2.26 (s, 3H)

Examples 124 to 133

The titled compounds of Examples 124 to 133 were prepared, in accordance with the same procedures as in Example 123, using 7-(4-fluorobenzyloxy)-1-(2-methoxyethyl)-2,3-dimethyl-1H-pyrrolo[3,2-b]pyridine prepared in Example 122; and, benzenesulfonic acid, p-toluenesulfonic acid, nitric acid, sulfuric acid, maleic acid, phosphoric acid, malonic acid, camphosulfonic acid, oxalic acid, or hydrobromic acid.

Example 124

7-(4-fluorobenzyloxy)-1-(2-methoxyethyl)-2,3-dimethyl-1H-pyrrolo[3,2-b]pyridine benzenesulfonate $^1$H-NMR (DMSO-d$_6$) δ8.50 (s, 1H), 7.63 (m, 4H), 7.31 (s, 6H), 5.55 (s, 2H), 4.47 (s, 2H), 3.52 (s, 2H), 3.11 (s, 3H), 2.43 (s, 3H), 2.26 (s, 3H); (Yield: 92.3%)

Example 125

7-(4-fluorobenzyloxy)-1-(2-methoxyethyl)-2,3-dimethyl-1H-pyrrolo[3,2-b]pyridine p-toluenesulfonate $^1$H-NMR (DMSO-d$_6$) δ8.50 (s, 1H), 7.63 (s, 2H), (s, 3H), 7.46 (d, 2H), 7.32 (m, 3H), 7.12 (d, 2H), 5.55 (s, 2H), 4.47 (s, 2H), 3.52 (s, 2H), 3.11 (s, 3H), 2.43 (s, 3H), 2.28 (s, 3H), 2.26 (s, 3H); (Yield: 95.4%)

Example 126

7-(4-fluorobenzyloxy)-1-(2-methoxyethyl)-2,3-dimethyl-1H-pyrrolo[3,2-b]pyridine nitrate $^1$H-NMR (DMSO-d$_6$) δ8.48 (s, 1H), 7.64 (s, 2H), 7.32 (m, 3H), 5.55 (s, 2H), 4.47 (s, 2H), 3.52 (s, 2H), 3.11 (s, 3H), 2.43 (s, 3H), 2.26 (s, 3H); (Yield: 88.4%)

Example 127

7-(4-fluorobenzyloxy)-1-(2-methoxyethyl)-2,3-dimethyl-1H-pyrrolo[3,2-b]pyridine sulfate $^1$H-NMR (DMSO-d$_6$) δ8.24 (s, 1H), 7.41 (s, 2H), 7.08 (m, 3H), 5.31 (s, 2H), 4.24 (s, 2H), 3.33 (s, 2H), 2.88 (s, 3H), 2.20 (s, 3H), 2.03 (s, 3H); (Yield: 89.4%)

Example 128

7-(4-fluorobenzyloxy)-1-(2-methoxyethyl)-2,3-dimethyl-1H-pyrrolo[3,2-b]pyridine maleate $^1$H-NMR (DMSO-d$_6$) δ8.44 (s, 1H), 7.63 (s, 2H), 7.30 (m, 3H), 6.05 (s, 2H), 5.52 (s, 2H), 4.46 (s, 2H), 3.51 (s, 2H), 3.11 (s, 3H), 2.42 (s, 3H), 2.25 (s, 3H); (Yield: 96.5%)

Example 129

7-(4-fluorobenzyloxy)-1-(2-methoxyethyl)-2,3-dimethyl-1H-pyrrolo[3,2-b]pyridine phosphate $^1$H-NMR (DMSO-d$_6$) δ8.14 (s, 1H), 7.58 (s, 2H), 7.28 (t, 2H), 6.86 (s, 1H), 5.31 (s, 2H), 4.39 (s, 2H), 3.55 (s, 2H), 3.11 (s, 3H), 2.34 (s, 3H), 2.18 (s, 3H); (Yield: 88.2%)

Example 130

7-(4-fluorobenzyloxy)-1-(2-methoxyethyl)-2,3-dimethyl-1H-pyrrolo[3,2-b]pyridine malonate $^1$H-NMR (DMSO-d$_6$) δ8.23 (s, 1H), 7.60 (s, 2H), 7.29 (t, 2H), 6.98 (s, 1H), 5.37 (s, 2H), 4.40 (s, 2H), 3.56 (s, 2H), 3.11 (s, 3H), 3.04 (s, 2H), 2.36 (s, 3H), 2.20 (s, 3H); (Yield; 79.9%)

Example 131

7-(4-fluorobenzyloxy)-1-(2-methoxyethyl)-2,3-dimethyl-1H-pyrrolo[3,2-b]pyridine camphosulfonate $^1$H-NMR (DMSO-d$_6$) δ8.48 (d, 1H), 7.64 (s, 2H), 7.32 (m, 3H), 5.55 (s, 2H), 4.47 (s, 2H), 3.52 (s, 2H), 3.11 (s, 3H), 2.89 (d, 1H), 2.68 (m, 1H), 2.43 (s, 3H), 2.36 (d, 1H), 2.26 (s, 3H), 2.20 (s, 1H), 1.92 (s, 1H), 1.84 (m, 2H), 1.28 (m, 2H), 1.04 (s, 3H), 0.73 (s, 3H); (Yield: 86.9%)

Example 132

7-(4-fluorobenzyloxy)-1-(2-methoxyethyl)-2,3-dimethyl-1H-pyrrolo[3,2-b]pyridine oxalate $^1$H-NMR (DMSO-d$_6$) δ8.33 (s, 1H), 7.61 (s, 2H), 7.28 (t, 2H), 7.12 (s, 1H), 5.44 (s, 2H), 4.43 (s, 2H), 3.51 (s, 2H), 3.11 (s, 3H), 2.34 (s, 3H), 2.16 (s, 3H); (Yield: 95.2%)

Example 133

7-(4-fluorobenzyloxy)-1-(2-methoxyethyl)-2,3-dimethyl-1H-pyrrolo[3,2-b]pyridine hydrobromide $^1$H-NMR (DMSO-d$_6$) δ8.37 (s, 1H), 7.53 (s, 2H), 7.21 (m, 3H), 5.45 (s, 2H), 4.36 (s, 2H), 3.41 (d, 2H), 3.00 (s, 3H), 2.33 (s, 3H), 2.16 (s, 3H); (Yield: 75.8%)

Example 134

7-(2,4-dichlorobenzyloxy)-1-methoxymethyl-2,3-dimethyl-1H-pyrrolo[3,2-b]pyridine hydrochloride Step 1: 4-(2,4-dichlorobenzyloxy)-3-nitropyridine In accordance with the same procedures as in Preparation 2, except for using 4-chloro-3-nitropyridine prepared in Step 1 of Preparation 1 and 2,4-dichlorobenzyl alcohol, the titled compound was obtained as a white solid. (Yield: 89.3%)
$^1$H-NMR (CDCl$_3$) δ9.05 (s, 1H), 8.60 (d, 1H), 7.13 (d, 1H), 5.29 (d, 1H)

Step 2: 7-(2,4-dichlorobenzyloxy)-2,3-dimethyl-1H-pyrrolo[3,2-b]pyridine

In accordance with the same procedures as in Step 1 of Example 33, except for using 4-(2,4-dichlorobenzyloxy)-3-nitropyridine prepared in Step 1, the titled compound was obtained as a white solid. (Yield: 28.6%)
$^1$H-NMR (CDCl$_3$) δ8.29 (d, 1H), 8.01 (s, 1H), 7.52 (m, 3H), 6.53 (d, 1H), 5.18 (s, 2H), 2.41 (s, 3H), 2.31 (s, 3H)

Step 3: 7-(2,4-dichlorobenzyloxy)-1-methoxymethyl-2,3-dimethyl-1H-pyrrolo[3,2-b]pyridine hydrochloride In accordance with the same procedures as in Step 2 of Example 33, except for using 7-(2,4-dichlorobenzyloxy)-2,3-dimethyl-1H-pyrrolo[3,2-b]pyridine prepared in Step 2 and bromomethyl methyl ether, the titled compound was obtained as a white solid. (Yield: 58.9%)
$^1$H-NMR (CDCl$_3$) δ8.38 (d, 1H), 7.54 (m, 2H), 7.51 (m, 2H), 5.61 (s, 2H), 5.50 (s, 2H), 3.17 (s, 3H), 2.56 (s, 3H), 2.49 (s, 3H)

Examples 135 to 143

The titled compounds of Examples 135 to 143 were prepared, in accordance with the same procedures as in Step 2 of Example 33, using 7-(2,4-dichlorobenzyloxy)-2,3-dimethyl-1H-pyrrolo[3,2-b]pyridine prepared in Step 2 of Example 134; and, 4-bromo-2-methyl-2-butene, benzyl bromide, iodoethane, bromomethyl acetate, (bromomethyl)cyclopropane, 4-fluorobenzyl bromide, 3-methoxybenzyl bromide, 2-chlorobenzyl bromide, or 4-tert-butylbenzyl chloride.

Example 135

7-(2,4-dichlorobenzyloxy)-2,3-dimethyl-1-(3-methylbut-2-enyl)-1H-pyrrolo[3,2-b]pyridine hydrochloride $^1$H-NMR (CDCl$_3$) δ8.36 (s, 1H), 7.52 (s, 1H), 7.43 (m, 3H), 5.60 (s, 2H), 5.14 (t, 1H), 4.80 (s, 2H), 2.55 (s, 3H), 2.41 (s, 3H), 1.59 (s, 6H); (Yield: 75.9%)

Example 136

1-benzyl-7-(2,4-dichlorobenzyloxy)-2,3-dimethyl-1H-pyrrolo[3,2-b]pyridine hydrochloride $^1$H-NMR (CDCl$_3$) δ8.33 (d, 1H), 7.43 (s, 3H), 7.11 (m, 2H), 6.89 (m, 1H), 6.67 (m, 2H), 5.58 (s, 2H), 5.32 (s, 2H), 2.64 (s, 3H), 2.41 (s, 3H); (Yield: 86.4%)

Example 137

7-(2,4-dichlorobenzyloxy)-1-ethyl-2,3-dimethyl-1H-pyrrolo[3,2-b]pyridine hydrochloride $^1$H-NMR (CDCl$_3$) δ8.37 (d, 1H), 7.55 (s, 1H), 7.52 (d, 1H), 7.43 (d, 1H), 6.93 (d, 1H), 5.45 (s, 2H), 4.34 (m, 2H), 2.58 (s, 3H), 2.42 (s, 3H), 1.11 (t, 3H); (Yield: 75.9%)

Example 138

7-(2,4-dichlorobenzyloxy)-1-methoxycarbonylmethyl-2,3-dimethyl-1H-pyrrolo[3,2-b]pyridine hydrochloride $^1$H-NMR (CDCl$_3$) δ8.37 (d, 1H), 7.54 (s, 1H), 7.39 (m, 2H), 6.89 (s, 1H), 5.40 (s, 2H), 5.04 (s, 2H), 3.61 (s, 3H), 2.57 (s, 3H), 2.36 (s, 3H); (Yield: 69.7%)

Example 139

1-cyclopropylmethyl-7-(2,4-dichlorobenzyloxy)-2,3-dimethyl-1H-pyrrolo[3,2-b]pyridine hydrochloride $^1$H-NMR (CDCl$_3$) δ8.41 (d, 1H), 7.60 (m, 2H), 7.52 (m, 1H), 7.38 (m, 1H), 5.45 (s, 2H), 4.33 (d, 2H), 2.56 (s, 3H), 2.47 (s, 3H), 1.11 (m, 1H), 0.48 (m, 2H), 0.19 (m, 2H); (Yield: 78.3%)

Example 140

7-(2,4-dichlorobenzyloxy)-1-(4-fluorobenzyl)-2,3-dimethyl-1H-pyrrolo[3,2-b]pyridine hydrochloride $^1$H-NMR (CDCl$_3$) δ8.40 (d, 1H), 7.44 (s, 1H), 7.19 (m, 2H), 6.90 (m, 3H), 6.38 (m, 2H), 5.52 (s, 2H), 5.32 (s, 2H), 2.61 (s, 3H), 2.39 (s, 3H); (Yield: 75.5%)

Example 141

7-(2,4-dichlorobenzyloxy)-1-(3-methoxybenzyl)-2,3-dimethyl-1H-pyrrolo[3,2-b]pyridine hydrochloride $^1$H-NMR (CDCl$_3$) δ8.33 (d, 1H), 7.42 (s, 1H), 7.13 (m, 3H), 6.86 (m, 3H), 6.20 (s, 1H), 5.52 (s, 2H), 5.31 (s, 2H), 3.70 (s, 3H), 2.55 (s, 3H), 2.38 (s, 3H); (Yield: 78.6%)

Example 142

1-(2-chlorobenzyl)-7-(2,4-dichlorobenzyloxy)-2,3-dimethyl-1H-pyrrolo[3,2-b]pyridine hydrochloride $^1$H-NMR (CDCl$_3$) δ8.39 (d, 1H), 7.38 (s, 1H), 7.31 (m, 2H), 7.14 (m, 2H), 6.84 (d, 2H), 6.01 (d, 1H), 5.57 (d, 2H), 5.26 (s, 2H), 2.63 (s, 3H), 2.36 (s, 3H); (Yield: 58.5%)

Example 143

1-(4-tert-butylbenzyl)-7-(2,4-dichlorobenzyloxy)-2,
3-dimethyl-1H-pyrrolo[3,2-b]pyridine hydrochloride $^1$H-NMR (CDCl$_3$) δ8.37 (d, 1H), 7.43 (s, 1H), 7.23 (m, 2H), 7.10 (s, 1H), 6.92 (m, 2H), 6.60 (d, 2H), 5.29 (s, 2H), 5.33 (s, 2H), 2.61 (s, 3H), 2.44 (s, 3H), 1.28 (s, 9H); (Yield: 68.8%)

Example 144

1-benzyl-2,3-dimethyl-7-(3-methylbenzyloxy)-1H-pyrrolo[3,2-b]pyridine hydrochloride Step 1: 4-(3-methylbenzyloxy)-3-nitropyridine In accordance with the same procedures as in Preparation 2, except for using 4-chloro-3-nitropyridine prepared in Step 1 of Preparation 1 and 3-methylbenzyl alcohol, the titled compound was obtained as a yellow solid. (Yield: 89.8%)

$^1$H-NMR (CDCl$_3$) δ9.03 (s, 1H), 8.62 (d, 1H), 7.45 (m, 4H), 7.09 (d, 1H), 5.35 (d, 1H), 1.53 (s, 3H)

Step 2: 7-(3-methylbenzyloxy)-2,3-dimethyl-1H-pyrrolo[3,2-b]pyridine

In accordance with the same procedures as in Step 1 of Example 33, except for using 4-(3-methylbenzyloxy)-3-nitropyridine prepared in Step 1, the titled compound was obtained as a pale yellow solid. (Yield: 28.3%)

$^1$H-NMR (CDCl$_3$) δ8.29 (d, 1H), 8.01 (s, 1H), 7.40 (m, 4H), 6.58 (d, 1H), 5.23 (s, 2H), 2.40 (s, 3H), 2.30 (s, 3H), 1.55 (s, 1H)

Step 3: 1-benzyl-2,3-dimethyl-7-(3-methylbenzyloxy)-1H-pyrrolo[3,2-b]pyridine hydrochloride In accordance with the same procedures as in Step 2 of Example 33, except for using 7-(3-methylbenzyloxy)-2,3-dimethyl-1H-pyrrolo[3,2-b]pyridine prepared in Step 2 and benzyl bromide, the titled compound was obtained as a white solid. (Yield: 89.3%)

$^1$H-NMR (CDCl$_3$) δ8.33 (d, 1H), 7.20 (m, 3H), 6.89 (d, 2H), 6.81 (d, 1H), 6.72 (d, 2H), 5.59 (s, 2H), 5.23 (s, 2H), 2.60 (s, 3H), 2.32 (s, 3H), 2.24 (s, 3H)

Examples 145 to 159

The titled compounds of Examples 145 to 159 were prepared, in accordance with the same procedures as in Step 2 of Example 33, using 7-(3-methylbenzyloxy)-2,3-dimethyl-1H-pyrrolo[3,2-b]pyridine prepared in Step 2 of Example 144; and, iodoethane, 3-fluorobenzyl chloride, 4-chlorobenzyl chloride, 3-methylbenzyl chloride, 2-chloromethylpyridine, 2,5-dimethylbenzyl chloride, 4-tert-butylbenzyl chloride, 4-bromo-2-methyl-2-butene, 1-iodopropane, (bromomethyl)cyclopropane, allyl bromide, 4-methylbenzyl chloride, 2-bromoethyl methyl ether, 4-fluorobenzyl chloride, or 3-methoxybenzyl chloride.

Example 145

1-ethyl-2,3-dimethyl-7-(3-methylbenzyloxy)-1H-pyrrolo[3,2-b]pyridine hydrochloride $^1$H-NMR (CDCl$_3$) δ8.31 (s, 1H), 7.34 (m, 4H), 6.86 (d, 1H), 5.37 (s, 2H), 4.38 (m, 2H), 2.53 (s, 3H), 2.42 (s, 3H), 2.40 (s, 3H), 1.29 (t, 3H); (Yield: 69.0%)

Example 146

1-(3-fluorobenzyl)-2,3-dimethyl-7-(3-methylbenzyloxy)-1H-pyrrolo[3,2-b]pyridine hydrochloride $^1$H-NMR (CDCl$_3$) δ8.36 (d, 1H), 7.18 (m, 3H), 6.97 (m, 3H), 6.83 (d, 1H), 6.64 (m, 2H), 5.54 (s, 2H), 5.23 (s, 2H), 2.60 (s, 3H), 2.37 (s, 3H), 2.30 (s, 3H); (Yield: 58.9%)

Example 147

1-(4-chlorobenzyl)-2,3-dimethyl-7-(3-methylbenzyloxy)-1H-pyrrolo[3,2-b]pyridine hydrochloride $^1$H-NMR (CDCl$_3$) δ8.34 (t, 1H), 7.19 (m, 4H), 6.90 (m, 3H), 6.61 (d, 2H), 5.57 (s, 2H), 5.22 (s, 2H), 2.59 (s, 3H), 2.37 (s, 3H), 2.30 (s, 3H); (Yield: 51.4%)

Example 148

2,3-dimethyl-1-(3-methylbenzyl)-7-(3-methylbenzyloxy)-1H-pyrrolo[3,2-b]pyridine hydrochloride $^1$H-NMR (CDCl$_3$) δ8.33 (d, 1H), 7.34 (m, 1H), 7.14 (m, 2H), 7.09 (d, 1H), 6.91 (m, 3H), 6.50 (m, 2H), 5.56 (s, 2H), 5.25 (s, 2H), 2.59 (s, 3H), 2.40 (s, 3H), 2.37 (s, 3H), 2.27 (s, 3H); (Yield: 63.3%)

Example 149

2,3-dimethyl-7-(3-methylbenzyloxy)-1-(pyridin-2-ylmethyl)-1H-pyrrolo[3,2-b]pyridine hydrochloride $^1$H-NMR (CDCl$_3$) δ8.36 (d, 1H), 7.18 (m, 3H), 6.97 (m, 3H), 6.83 (d, 1H), 6.64 (m, 2H), 5.54 (s, 2H), 5.23 (s, 2H), 2.60 (s, 3H), 2.37 (s, 3H), 2.30 (s, 3H); (Yield: 85.4%)

Example 150

1-(2,5-dimethylbenzyl)-2,3-dimethyl-7-(3-methylbenzyloxy)-1H-pyrrolo[3,2-b]pyridine hydrochloride $^1$H-NMR (CDCl$_3$) δ8.34 (d, 1H), 7.33 (m, 1H), 7.16 (m, 2H), 6.99 (m, 2H), 6.79 (m, 3H), 5.44 (s, 2H), 5.15 (s, 2H), 2.63 (s, 3H), 2.40 (s, 3H), 2.27 (s, 6H), 2.00 (s, 3H); (Yield: 72.0%)

Example 151

1-(4-tert-butylbenzyl)-2,3-dimethyl-7-(3-methylbenzyloxy)-1H-pyrrolo[3,2-b]pyridine hydrochloride $^1$H-NMR (CDCl$_3$) δ8.34 (d, 1H), 7.34 (m, 4H), 7.19 (d, 1H), 6.97 (s, 1H), 6.87 (m, 1H), 6.65 (d, 1H), 5.56 (s, 2H), 5.25 (s, 2H), 2.59 (s, 3H), 2.54 (s, 3H), 2.37 (s, 3H), 1.29 (s, 9H); (Yield: 80.1%)

Example 152

2,3-dimethyl-7-(3-methylbenzyloxy)-1-(3-methyl-but-2-enyl)-1H-pyrrolo[3,2-b]pyridine hydrochloride $^1$H-NMR (CDCl$_3$) δ8.40 (d, 1H), 7.31 (m, 4H), 5.40 (s, 2H), 5.21 (m, 1H), 4.99 (s, 2H), 2.57 (s, 3H), 2.38 (s, 6H), 1.81 (s, 6H); (Yield: 74.6%)

Example 153

2,3-dimethyl-7-(3-methylbenzyloxy)-1-propyl-1H-pyrrolo[3,2-b]pyridine hydrochloride $^1$H-NMR (CDCl$_3$) δ8.34 (s, 1H), 7.34 (m, 4H), 6.88 (s, 1H), 5.33 (s, 2H), 4.20 (t, 2H), 2.40 (s, 3H), 2.30 (s, 3H), 2.17 (s, 3H), 1.69 (m, 2H), 0.75 (t, 3H); (Yield: 78.2%)

Example 154

1-cyclopropylmethyl-2,3-dimethyl-7-(3-methylbenzyloxy)-1H-pyrrolo[3,2-b]pyridine hydrochloride $^1$H-NMR (CDCl$_3$) δ8.35 (d, 1H), 7.34 (m, 4H), 6.89 (d, 1H), 5.35 (s, 2H), 4.13 (d, 2H), 2.56 (s, 3H), 2.45 (s, 3H), 2.41 (s, 3H), 1.13 (m, 1H), 0.48 (m, 2H), 0.22 (m, 2H); (Yield: 66.9%)

Example 155

1-allyl-2,3-dimethyl-7-(3-methylbenzyloxy)-1H-pyrrolo[3,2-b]pyridine hydrochloride $^1$H-NMR (CDCl$_3$) δ8.33 (d, 1H), 7.31 (m, 3H), 6.85 (d, 1H), 5.90 (m, 1H), 5.35 (s, 2H), 5.15 (d, 1H), 4.97 (s, 2H), 4.57 (d, 1H), 2.57 (s, 3H), 2.39 (s, 6H); (Yield: 72.3%)

Example 156

2,3-dimethyl-1-(4-methylbenzyl)-7-(3-methylbenzyloxy)-1H-pyrrolo[3,2-b]pyridine hydrochloride $^1$H-NMR (CDCl$_3$) δ8.32 (d, 1H), 7.19 (m, 2H), 7.09 (d, 2H), 6.92 (m, 3H), 6.62 (d, 2H), 5.55 (s, 2H), 5.25 (s, 2H), 2.58 (s, 3H), 2.37 (s, 3H), 2.27 (s, 3H), 2.27 (s, 3H); (Yield: 93.5%)

Example 157

1-(2-methoxyethyl)-2,3-dimethyl-7-(3-methylbenzyloxy)-1H-pyrrolo[3,2-b]pyridine hydrochloride $^1$H-NMR (CDCl$_3$) δ8.33 (d, 1H), 7.34 (m, 4H), 6.87 (d, 1H), 5.36 (s, 2H), 4.47 (m, 2H), 3.50 (m, 2H), 3.20 (s, 3H), 2.54 (s, 3H), 2.44 (s, 3H), 2.40 (s, 3H); (Yield: 86.3%)

Example 158

1-(4-fluorobenzyl)-2,3-dimethyl-7-(3-methylbenzyloxy)-1H-pyrrolo[3,2-b]pyridine hydrochloride $^1$H-NMR (CDCl$_3$) δ8.35 (t, 1H), 7.20 (m, 3H), 7.00 (m, 3H), 6.85 (d, 1H), 6.42 (m, 2H), 5.55 (s, 2H), 5.23 (s, 2H), 2.60 (s, 3H), 2.37 (s, 3H), 2.29 (s, 3H); (Yield: 91.0%)

Example 159

1-(3-methoxybenzyl)-2,3-dimethyl-7-(3-methylbenzyloxy)-1H-pyrrolo[3,2-b]pyridine hydrochloride $^1$H-NMR (CDCl$_3$) δ8.33 (d, 1H), 7.33 (m, 1H), 7.17 (m, 2H), 6.91 (s, 2H), 6.81 (d, 2H), 6.27 (s, 1H), 5.56 (s, 2H), 5.24 (s, 2H), 3.70 (s, 3H), 2.52 (s, 3H), 2.49 (s, 3H), 2.17 (s, 3H); (Yield: 88.5%)

Example 160

1-(3-chlorobenzyl)-7-(2-ethoxybenzyloxy)-2,3-dimethyl-1H-pyrrolo[3,2-b]pyridine hydrochloride Step 1: 4-(2-ethoxybenzyloxy)-3-nitropyridine In accordance with the same procedures as in Preparation 2, except for using 4-chloro-3-nitropyridine prepared in Step 1 of Preparation 1 and 2-ethoxybenzyl alcohol, the titled compound was obtained as a yellow solid. (Yield: 65.9%)

$^1$H-NMR (CDCl$_3$) δ9.04 (s, 1H), 8.62 (d, 1H), 7.32 (m, 4H), 7.04 (d, 1H), 5.33 (d, 1H), 2.87 (m, 2H), 1.2 (t, 3H)

Step 2: 7-(2-ethoxybenzyloxy)-2,3-dimethyl-1H-pyrrolo[3,2-b]pyridine

In accordance with the same procedures as in Step 1 of Example 33, except for using 4-(2-ethoxybenzyloxy)-3-nitropyridine prepared in Step 1, the titled compound was obtained as a white solid. (Yield: 25.5%)

$^1$H-NMR (CDCl$_3$) δ8.30 (d, 1H), 8.01 (s, 1H), 7.25 (m, 4H), 6.58 (d, 1H), 5.30 (s, 2H), 3.12 (m, 2H), 2.41 (s, 3H), 2.26 (s, 3H), 1.21 (t, 3H)

Step 3: 1-(3-chlorobenzyl)-7-(2-ethoxybenzyloxy)-2,3-dimethyl-1H-pyrrolo[3,2-b]pyridine hydrochloride In accordance with the same procedures as in Step 2 of Example 33, except for using 7-(2-ethoxybenzyloxy)-2,3-dimethyl-1H-pyrrolo[3,2-b]pyridine prepared in Step 2 and 3-chlorobenzyl bromide, the titled compound was obtained as a white solid. (Yield: 79.8%)

$^1$H-NMR (CDCl$_3$) δ8.26 (d, 1H), 7.88 (d, 1H), 7.23 (m, 3H), 7.04 (t, 3H), 6.97 (d, 4H), 6.63 (m, 2H), 5.28 (m, 2H), 3.01 (s, 3H), 2.36 (s, 3H), 2.33 (s, 3H),

Examples 161 to 178

The titled compounds of Examples 161 to 178 were prepared, in accordance with the same procedures as in Step 2 of Example 33, using 7-(2-ethoxybenzyloxy)-2,3-dimethyl-1H-pyrrolo[3,2-b]pyridine prepared in Step 2 of Example 160; and, (bromomethyl)cyclopropane, 2-bromoethyl methyl ether, (bromomethyl)cyclobutane, allyl bromide, iodoethane, 3,4-dichlorobenzyl chloride, 2-methoxybenzyl chloride, 2-chlorobenzyl chloride, 2-fluorobenzyl chloride, 1-iodopropane, 4-methoxybenzyl chloride, 4-chlorobenzyl chloride, 3-methylbenzyl chloride, 4-methylbenzyl chloride, 4-fluorobenzyl chloride, 2-bromomethyl-1,3-dioxolane, 3-methoxybenzyl bromide, or 3-fluorobenzyl bromide.

Example 161

1-cyclopropylmethyl-7-(2-ethoxybenzyloxy)-2,3-dimethyl-1H-pyrrolo[3,2-b]pyridine hydrochloride $^1$H-NMR (CDCl$_3$) δ8.33 (t, 1H), 7.39 (m, 2H), 6.96 (m, 3H), 5.44 (s, 2H), 4.23 (d, 2H), 4.12 (m, 2H), 2.55 (s, 3H), 2.43 (s, 3H), 1.41 (t, 3H), 1.12 (m, 1H), 0.43 (m, 2H), 0.20 (m, 2H); (Yield: 82.5%)

Example 162

7-(2-ethoxybenzyloxy)-1-(2-methoxyethyl)-2,3-dimethyl-1H-pyrrolo[3,2-b]pyridine hydrochloride $^1$H-NMR (CDCl$_3$) δ8.31 (t, 1H), 7.36 (m, 2H), 6.96 (m, 3H), 5.45 (s, 2H), 4.45 (t, 2H), 4.11 (m, 2H), 3.54 (t, 2H), 3.17 (s, 3H), 2.52 (s, 3H), 2.42 (s, 3H), 1.40 (t, 3H); (Yield: 78.4%)

Example 163

1-cyclobutylmethyl-7-(2-ethoxybenzyloxy)-2,3-dimethyl-1H-pyrrolo[3,2-b]pyridine hydrochloride $^1$H-NMR (CDCl$_3$) δ8.32 (s, 1H), 7.39 (m, 2H), 6.97 (m, 3H), 5.45 (s, 2H), 4.30 (s, 2H), 4.12 (d, 2H), 2.63 (m, 1H), 2.54 (s, 3H), 2.41 (s, 3H), 1.77~1.55 (m, 6H), 1.25 (t, 3H); (Yield: 69.7%)

Example 164

1-allyl-7-(2-ethoxybenzyloxy)-2,3-dimethyl-1H-pyrrolo[3,2-b]pyridine hydrochloride $^1$H-NMR (CDCl$_3$) δ8.31 (d, 1H), 7.36 (m, 2H), 6.97 (m, 3H), 5.58 (m, 1H), 5.49 (s, 2H), 5.11 (d, 1H), 4.97 (s, 2H), 4.61 (d, 1H), 4.12 (m, 2H), 2.55 (s, 3H), 2.38 (s, 3H), 1.42 (t, 3H); (Yield: 51.0%)

Example 165

7-(2-ethoxybenzyloxy)-1-ethyl-2,3-dimethyl-1H-pyrrolo[3,2-b]pyridine hydrochloride $^1$H-NMR (CDCl$_3$) δ8.30 (t, 1H), 7.37 (d, 1H), 6.98 (m, 3H), 5.46 (s, 2H), 4.36 (m, 2H), 4.12 (m, 2H), 2.53 (s, 3H), 2.40 (s, 3H), 1.40 (t, 3H), 1.28 (t, 3H); (Yield: 65.8%)

Example 166

1-(3,4-dichlorobenzyl)-7-(2-ethoxybenzyloxy)-2,3-dimethyl-1H-pyrrolo[3,2-b]pyridine hydrochloride $^1$H-NMR (CDCl$_3$) δ8.36 (d, 1H), 7.38 (m, 2H), 6.99 (t, 2H), 6.89 (t, 2H), 6.78 (s, 1H), 6.42 (d, 1H), 5.48 (s, 2H), 5.32 (s, 2H), 3.99 (m, 2H), 2.53 (s, 3H), 2.35 (s, 3H), 1.29 (t, 3H); (Yield: 74.0%)

Example 167

7-(2-ethoxybenzyloxy)-1-(2-methoxybenzyl)-2,3-dimethyl-1H-pyrrolo[3,2-b]pyridine hydrochloride $^1$H-NMR (CDCl$_3$) δ8.32 (t, 1H), 7.21 (m, 3H), 6.82 (m, 5H), 6.02 (d, 1H), 5.58 (s, 2H), 5.30 (s, 2H), 3.98 (m, 2H), 3.76 (s, 3H), 2.58 (s, 3H), 2.31 (s, 3H), 1.32 (t, 3H); (Yield: 63.5%)

Example 168

1-(2-chlorobenzyl)-7-(2-ethoxybenzyloxy)-2,3-dimethyl-1H-pyrrolo[3,2-b]pyridine hydrochloride $^1$H-NMR (CDCl$_3$) δ8.33 (t, 1H), 7.36 (d, 1H), 7.21 (m, 2H), 7.10 (t, 1H), 6.92 (d, 1H), 6.82 (d, 1H), 6.75 (s, 2H), 6.02 (d, 2H), 5.64 (s, 2H), 5.30 (s, 2H), 3.96 (m, 2H), 2.60 (s, 3H), 2.33 (s, 3H), 1.31 (t, 3H); (Yield: 74.2%)

Example 169

7-(2-ethoxybenzyloxy)-1-(2-fluorobenzyl)-2,3-dimethyl-1H-pyrrolo[3,2-b]pyridine hydrochloride $^1$H-NMR (CDCl$_3$) δ8.32 (t, 1H), 7.30 (m, 1H), 6.96 (m, 4H), 6.85 (m, 3H), 6.24 (t, 1H), 5.65 (s, 2H), 5.35 (s, 2H), 4.01 (m, 2H), 2.58 (s, 3H), 2.35 (s, 3H), 1.34 (t, 3H); (Yield: 63.0%)

Example 170

7-(2-ethoxybenzyloxy)-1-propyl-2,3-dimethyl-1H-pyrrolo[3,2-b]pyridine hydrochloride $^1$H-NMR (CDCl$_3$) δ8.33 (d, 1H), 7.39 (m, 2H), 7.00 (m, 3H), 5.43 (d, 2H), 4.21 (m, 2H), 4.11 (m, 2H), 2.54 (s, 3H), 2.40 (s, 3H), 1.58 (m, 2H), 1.39 (m, 3H), 0.74 (m, 3H); (Yield: 68.8%)

Example 171

7-(2-ethoxybenzyloxy)-1-(4-methoxybenzyl)-2,3-dimethyl-1H-pyrrolo[3,2-b]pyridine hydrochloride $^1$H-NMR (CDCl$_3$) δ8.31 (t, 1H), 7.32 (t, 1H), 6.96 (m, 4H), 6.77 (d, 2H), 6.64 (d, 2H), 5.52 (s, 2H), 5.36 (s, 2H), 4.04 (m, 2H), 3.81 (s, 3H), 2.56 (s, 3H), 2.36 (s, 3H), 1.34 (t, 3H); (Yield: 84.0%)

Example 172

1-(4-chlorobenzyl)-7-(2-ethoxybenzyloxy)-2,3-dimethyl-1H-pyrrolo[3,2-b]pyridine hydrochloride $^1$H-NMR (CDCl$_3$) δ8.34 (t, 1H), 7.35 (t, 1H), 7.19 (d, 2H), 6.94 (d, 1H), 6.87 (d, 1H), 6.60 (d, 1H), 5.52 (s, 2H), 5.33 (s, 2H), 3.98 (m, 2H), 2.59 (s, 3H), 2.36 (s, 3H), 1.31 (t, 3H); (Yield: 75.0%)

Example 173

7-(2-ethoxybenzyloxy)-1-(3-methylbenzyl)-2,3-dimethyl-1H-pyrrolo[3,2-b]pyridine hydrochloride $^1$H-NMR (CDCl$_3$) δ8.31 (t, 1H), 7.30 (m, 1H), 7.15 (m, 2H), 7.11 (m, 1H), 6.92 (m, 2H), 6.87 (m, 1H), 6.49 (m, 2H), 5.50 (s, 2H), 5.35 (s, 2H), 4.01 (m, 2H), 2.58 (s, 3H), 2.47 (s, 3H), 2.29 (s, 3H), 1.34 (t, 3H); (Yield: 83.0%)

Example 174

7-(2-ethoxybenzyloxy)-1-(4-methylbenzyl)-2,3-dimethyl-1H-pyrrolo[3,2-b]pyridine hydrochloride $^1$H-NMR (CDCl$_3$) δ8.30 (d, 1H), 7.52 (m, 1H), 7.05 (d, 2H), 6.88 (m, 4H), 6.62 (d, 2H), 5.55 (s, 2H), 5.35 (s, 2H), 4.02 (m, 2H), 2.58 (s, 3H), 2.35 (s, 3H), 2.31 (s, 3H), 1.34 (t, 3H); (Yield: 75.0%)

Example 175

1-(4-fluorobenzyl)-7-(2-ethoxybenzyloxy)-2,3-dimethyl-1H-pyrrolo[3,2-b]pyridine hydrochloride $^1$H-NMR (CDCl$_3$) δ8.34 (d, 1H), 7.34 (t, 1H), 6.93 (m, 6H), 6.67 (t, 2H), 5.53 (s, 2H), 5.34 (s, 2H), 4.01 (m, 2H), 2.57 (s, 3H), 2.36 (s, 3H), 1.32 (t, 3H); (Yield: 64.0%)

Example 176

1-(1,3-dioxolan-2-ylmethyl)-7-(2-ethoxybenzyloxy)-2,3-dimethyl-1H-pyrrolo[3,2-b]pyridine hydrochloride $^1$H-NMR (CDCl$_3$) δ8.86 (s, 1H), 8.33 (m, 1H), 7.42 (m, 2H), 6.95 (m, 2H), 5.48 (d, 2H), 5.10 (m, 1H), 4.53 (d, 2H), 4.11 (m, 2H), 3.71 (m, 4H), 2.52 (s, 3H), 2.45 (s, 3H), 1.40 (m, 3H); (Yield: 75.4%)

Example 177

7-(2-ethoxybenzyloxy)-1-(3-methoxybenzyl)-2,3-dimethyl-1H-pyrrolo[3,2-b]pyridine hydrochloride $^1$H-NMR (CDCl$_3$) δ8.32 (t, 1H), 7.31 (m, 1H), 7.16 (t, 1H), 6.92 (d, 2H), 6.84 (m, 3H), 6.26 (s, 2H), 5.57 (s, 2H), 5.35 (s, 2H), 4.01 (m, 2H), 3.68 (s, 3H), 2.57 (s, 3H), 2.35 (s, 3H), 1.34 (t, 3H); (Yield: 79.5%)

Example 178

1-(3-fluorobenzyl)-7-(2-ethoxybenzyloxy)-2,3-dimethyl-1H-pyrrolo[3,2-b]pyridine hydrochloride $^1$H-NMR (CDCl$_3$) δ8.33 (d, 1H), 7.33 (t, 1H), 7.19 (m, 1H), 6.94 (t, 3H), 6.85 (m, 2H), 6.43 (m, 2H), 5.55 (s, 2H), 5.34 (s, 2H), 3.99 (m, 2H), 2.59 (s, 3H), 2.36 (s, 3H), 1.34 (t, 3H); (Yield: 86.7%)

Example 179

1-cyclobutylmethyl-7-(3,5-difluorobenzyloxy)-2,3-dimethyl-1H-pyrrolo[3,2-b]pyridine hydrochloride Step 1: 4-(3,5-difluorobenzyloxy)-3-nitropyridine In accordance with the same procedures as in Preparation 2, except for using 4-chloro-3-nitropyridine prepared in Step 1 of Preparation 1 and 3,5-difluorobenzyl alcohol, the titled compound was obtained as a yellow solid. (Yield: 78.0%)

$^1$H-NMR (CDCl$_3$) δ9.06 (s, 1H), 8.73 (s, 1H), 8.65 (d, 1H), 7.40 (s, 1H), 7.35 (s, 1H), 7.04 (d, 1H), 5.28 (d, 1H)

Step 2: 7-(3,5-difluorobenzyloxy)-2,3-dimethyl-1H-pyrrolo[3,2-b]pyridine

In accordance with the same procedures as in Step 1 of Example 33, except for using 4-(3,5-difluorobenzyloxy)-3-nitropyridine prepared in Step 1, the titled compound was obtained as a white solid. (Yield: 20.4%)

$^1$H-NMR (CDCl$_3$) δ8.75 (s, 1H), 8.66 (d, 1H), 8.01 (s, 1H), 7.40 (s, 1H), 7.35 (s, 1H), 7.04 (d, 1H), 5.28 (d, 1H), 2.11 (s, 3H), 2.35 (s, 3H)

Step 3: 1-cyclobutylmethyl-7-(3,5-difluorobenzyloxy)-2,3-dimethyl-1H-pyrrolo[3,2-b]pyridine hydrochloride In accordance with the same procedures as in Step 2 of Example 33, except for using 7-(3,5-difluorobenzyloxy)-2,3-dimethyl-1H-pyrrolo[3,2-b]pyridine prepared in Step 2 and (bromomethyl)cyclobutane, the titled compound was obtained as a white solid. (Yield: 70.5%)

$^1$H-NMR (CDCl$_3$) δ8.36 (s, 1H), 7.02 (m, 2H), 6.91 (m, 1H), 6.82 (m, 1H), 5.36 (s, 2H), 4.35 (d, 2H), 2.67 (m, 1H), 2.55 (s, 3H), 2.44 (s, 3H), 1.73 (m, 2H), 1.67 (m, 2H)

Examples 180 to 199

The titled compounds of Examples 180 to 199 were prepared, in accordance with the same procedures as in Step 2 of Example 33, using 7-(3,5-difluorobenzyloxy)-2,3-dimethyl-1H-pyrrolo[3,2-b]pyridine prepared in Step 2 of Example 179; and, (bromomethyl)cyclopropane, 2-bromoethyl methyl ether, 1-iodopropane, 4-chlorobenzyl chloride, 4-fluorobenzyl bromide, iodoethane, 3,4-dichlorobenzyl chloride, iodomethane, 2-chlorobenzyl chloride, 3,4-dimethoxybenzyl chloride, 2-methoxybenzyl chloride, 2-fluorobenzyl chloride, 3-chlorobenzyl chloride, 4-methoxybenzyl chloride, 3-methoxybenzyl chloride, benzyl bromide, 4-methylbenzyl bromide, 2-chloromethylpyridine, 3-chloromethylpyridine, or 2-chloro-N,N-dimethylethylamine hydrochloride.

Example 180

1-cyclopropylmethyl-7-(3,5-difluorobenzyloxy)-2,3-dimethyl-1H-pyrrolo[3,2-b]pyridine hydrochloride $^1$H-NMR (CDCl$_3$) δ8.37 (d, 1H), 7.04 (m, 2H), 6.89 (m, 2H), 5.39 (s, 2H), 4.34 (d, 2H), 2.57 (s, 3H), 2.47 (s, 3H), 1.15 (m, 1H), 0.56 (m, 2H), 0.27 (m, 2H); (Yield: 86.0%)

Example 181

7-(3,5-difluorobenzyloxy)-1-(2-methoxyethyl)-2,3-dimethyl-1H-pyrrolo[3,2-b]pyridine hydrochloride $^1$H-NMR (CDCl$_3$) δ8.33 (d, 1H), 7.02 (d, 2H), 6.89 (m, 2H), 5.33 (s, 2H), 4.53 (t, 2H), 3.59 (t, 2H), 3.27 (s, 3H), 2.55 (s, 3H), 2.43 (s, 3H); (Yield: 75.6%)

Example 182

7-(3,5-difluorobenzyloxy)-2,3-dimethyl-1-propyl-1H-pyrrolo[3,2-b]pyridine hydrochloride $^1$H-NMR (CDCl$_3$) δ8.35 (d, 1H), 7.01 (d, 2H), 6.91 (m, 1H), 6.83 (m, 1H), 5.35 (s, 2H), 4.24 (t, 2H), 2.55 (s, 3H), 2.43 (s, 3H), 1.73 (m, 2H), 0.83 (t, 3H); (Yield: 58.7%)

Example 183

1-(4-chlorobenzyl)-7-(3,5-difluorobenzyloxy)-2,3-dimethyl-1H-pyrrolo[3,2-b]pyridine hydrochloride $^1$H-NMR (CDCl$_3$) δ8.37 (s, 1H), 7.37 (m, 1H), 7.03 (d, 1H), 6.85 (t, 2H), 6.59 (m, 4H), 5.56 (s, 2H), 5.23 (s, 2H), 2.53 (s, 3H), 2.39 (s, 3H); (Yield: 63.3%)

Example 184

7-(3,5-difluorobenzyloxy)-1-(4-fluorobenzyl)-2,3-dimethyl-1H-pyrrolo[3,2-b]pyridine hydrochloride $^1$H-NMR (CDCl$_3$) δ8.38 (d, 1H), 7.06 (m, 2H), 6.84 (m, 2H), 6.59 (s, 2H), 6.42 (m, 2H), 5.85 (s, 2H), 5.24 (s, 2H), 2.54 (s, 3H), 2.40 (s, 3H); (Yield: 71.2%)

Example 185

7-(3,5-difluorobenzyloxy)-1-ethyl-2,3-dimethyl-1H-pyrrolo[3,2-b]pyridine hydrochloride $^1$H-NMR (CDCl$_3$) δ8.34 (s, 1H), 6.99 (s, 2H), 6.89 (m, 1H), 6.82 (m, 1H), 5.38 (s, 2H), 4.40 (m, 2H), 2.55 (s, 3H), 2.44 (s, 3H), 1.27 (t, 3H); (Yield: 83.6%)

Example 186

7-(3,5-difluorobenzyloxy)-1-(3,4-dichlorobenzyl)-2,3-dimethyl-1H-pyrrolo[3,2-b]pyridine hydrochloride $^1$H-NMR (CDCl$_3$) δ8.40 (s, 1H), 7.49 (m, 1H), 6.82 (m, 2H), 6.65 (d, 2H), 6.50 (m, 2H), 5.49 (s, 2H), 5.24 (s, 2H), 2.54 (s, 3H), 2.39 (s, 3H); (Yield: 65.1%)

Example 187

7-(3,5-difluorobenzyloxy)-1,2,3-trimethyl-1H-pyrrolo[3,2-b]pyridine hydrochloride $^1$H-NMR (CDCl$_3$) δ8.33 (t, 1H), 7.00 (d, 2H), 6.91 (t, 1H), 6.81 (s, 1H), 5.37 (s, 2H), 4.00 (s, 3H), 2.55 (s, 3H), 2.43 (s, 3H); (Yield: 75.6%)

Example 188

1-(2-chlorobenzyl)-7-(3,5-difluorobenzyloxy)-2,3-dimethyl-1H-pyrrolo[3,2-b]pyridine hydrochloride $^1$H-NMR (CDCl$_3$) δ8.40 (t, 1H), 7.43 (m, 2H), 7.16 (m, 1H), 6.81 (m, 2H), 6.46 (s, 2H), 6.03 (m, 1H), 5.61 (s, 2H), 5.16 (s, 2H), 2.60 (s, 3H), 2.39 (s, 3H); (Yield: 63.8%)

Example 189

7-(3,5-difluorobenzyloxy)-1-(3,4-dimethoxybenzyl)-2,3-dimethyl-1H-pyrrolo[3,2-b]pyridine hydrochloride $^1$H-NMR (CDCl$_3$) δ7.98 (d, 1H), 7.61 (d, 1H), 7.01 (d, 2H), 6.91 (m, 4H), 6.82 (s, 2H), 5.71 (s, 2H), 5.64 (s, 2H), 3.81 (s, 3H), 2.34 (s, 3H), 2.27 (s, 3H); (Yield: 72.5%)

Example 190

7-(3,5-difluorobenzyloxy)-1-(2-methoxybenzyl)-2,3-dimethyl-1H-pyrrolo[3,2-b]pyridine hydrochloride $^1$H-NMR (CDCl$_3$) δ7.92 (d, 1H), 7.56 (d, 1H), 7.38 (t, 1H), 7.21 (t, 1H), 6.97 (m, 2H), 6.75 (t, 1H), 6.58 (d, 1H), 6.22 (d, 1H), 5.78 (s, 2H), 5.67 (s, 2H), 3.89 (s, 3H), 2.25 (s, 3H), 2.17 (s, 3H); (Yield: 64.2%)

Example 191

7-(3,5-difluorobenzyloxy)-1-(2-fluorobenzyl)-2,3-dimethyl-1H-pyrrolo[3,2-b]pyridine hydrochloride $^1$H-NMR (CDCl$_3$) δ8.37 (s, 1H), 7.36 (m, 1H), 7.05 (m, 3H), 6.81 (m, 2H), 6.56 (d, 2H), 5.63 (s, 2H), 5.30 (s, 2H), 2.56 (s, 3H), 2.39 (s, 3H); (Yield: 58.4%)

Example 192

1-(3-chlorobenzyl)-7-(3,5-difluorobenzyloxy)-2,3-dimethyl-1H-pyrrolo[3,2-b]pyridine hydrochloride $^1$H-NMR (CDCl$_3$) δ8.39 (d, 1H), 7.23 (m, 1H), 6.847 (m, 3H), 6.72 (s, 1H), 6.61 (m, 2H), 6.52 (m, 1H), 5.56 (s, 2H), 5.19 (s, 2H), 2.63 (s, 3H), 2.40 (s, 3H); (Yield: 85.4%)

Example 193

7-(3,5-difluorobenzyloxy)-1-(4-methoxybenzyl)-2,3-dimethyl-1H-pyrrolo[3,2-b]pyridine hydrochloride $^1$H-NMR (CDCl$_3$) δ8.34 (d, 1H), 6.91 (m, 4H), 6.64 (m, 4H), 5.54 (s, 2H), 5.24 (s, 2H), 3.73 (s, 3H), 2.61 (s, 3H), 2.39 (s, 3H); (Yield: 65.3%)

Example 194

7-(3,5-difluorobenzyloxy)-1-(3-methoxybenzyl)-2,3-dimethyl-1H-pyrrolo[3,2-b]pyridine hydrochloride $^1$H-NMR (CDCl$_3$) δ7.97 (d, 1H), 7.64 (d, 1H), 7.19 (t, 1H), 6.89 (d, 1H), 6.78 (d, 1H), 6.56 (m, 2H), 6.46 (s, 2H), 5.76 (s, 2H), 5.68 (s, 2H), 3.76 (s, 3H), 2.35 (s, 3H), 2.31 (s, 3H); (Yield: 69.4%)

Example 195

1-benzyl-7-(3,5-difluorobenzyloxy)-2,3-dimethyl-1H-pyrrolo[3,2-b]pyridine hydrochloride H-NMR (CDCl$_3$) δ8.35 (d, 1H), 7.42 (m, 4H), 6.80 (m, 4H), 6.55 (d, 1H), 5.60 (s, 2H), 5.25 (s, 2H), 2.62 (s, 3H), 2.45 (s, 3H); (Yield: 80.9%)

Example 196

7-(3,5-difluorobenzyloxy)-1-(4-methylbenzyl)-2,3-dimethyl-1H-pyrrolo[3,2-b]pyridine hydrochloride $^1$H-NMR (CDCl$_3$) δ8.34 (brs, 1H), 7.10 (m, 3H), 6.79 (m, 2H), 6.59 (m, 3H), 5.56 (s, 2H), 5.22 (s, 2H), 2.59 (s, 3H), 2.40 (s, 3H), 2.32 (s, 3H); (Yield: 91.5%)

Example 197

1-(pyridin-2-ylmethyl)-7-(3,5-difluorobenzyloxy)-2,3-dimethyl-1H-pyrrolo[3,2-b]pyridine hydrochloride $^1$H-NMR (CDCl$_3$) δ8.33 (brs, 1H), 7.14 (m, 3H), 6.87 (m, 2H), 6.54 (m, 3H), 5.53 (s, 2H), 5.24 (s, 2H), 2.40 (s, 3H), 2.32 (s, 3H); (Yield: 85.4%)

Example 198

1-(pyridin-3-ylmethyl)-7-(3,5-difluorobenzyloxy)-2,3-dimethyl-1H-pyrrolo[3,2-b]pyridine hydrochloride $^1$H-NMR (CDCl$_3$) δ8.37 (brs, 1H), 8.01 (s, 1H), 7.14 (m, 2H), 6.94 (m, 2H), 6.32 (m, 3H), 5.54 (s, 2H), 5.35 (s, 2H), 2.39 (s, 3H), 2.28 (s, 3H); (Yield: 75.6%)

Example 199

1-(2,2-dimethylaminoethyl)-7-(3,5-difluorobenzyloxy)-2,3-dimethyl-1H-pyrrolo[3,2-b]pyridine hydrochloride $^1$H-NMR (CDCl$_3$) δ8.45 (brs, 1H), 8.01 (s, 1H), 7.87 (m, 2H), 6.94 (d, 1H), 5.35 (s, 2H), 4.35 (d, 2H), 4.01 (d, 2H), 2.88 (s, 6H), 2.84 (m, 2H), 2.39 (s, 3H), 2.28 (s, 3H); (Yield: 66.3%)

Example 200

2,3-dimethyl-1-(4-methylbenzyl)-7-(4-trifluoromethylbenzyloxy)-1H-pyrrolo[3,2-b]pyridine hydrochloride Step 1: 4-(4-trifluoromethylbenzyloxy)-3-nitropyridine In accordance with the same procedures as in Preparation 2, except for using 4-chloro-3-nitropyridine prepared in Step 1 of Preparation 1 and 4-trifluoromethylbenzyl alcohol, the titled compound was obtained as a yellow solid. (Yield: 89.5%)

$^1$H-NMR (CDCl$_3$) δ9.03 (s, 1H), 8.66 (d, 1H), 7.38 (m, 4H), 7.02 (d, 1H), 5.29 (d, 1H)

Step 2: 7-(4-trifluoromethylbenzyloxy)-2,3-dimethyl-1H-pyrrolo[3,2-b]pyridine

In accordance with the same procedures as in Step 1 of Example 33, except for using 4-(4-trifluoromethylbenzyloxy)-3-nitropyridine prepared in Step 1, the titled compound was obtained as a white solid. (Yield: 29.5%)

$^1$H-NMR (CDCl$_3$) δ8.28 (d, 1H), 8.01 (s, 1H), 7.36 (m, 4H), 6.57 (d, 1H), 5.20 (s, 2H), 2.41 (s, 3H), 2.31 (s, 3H)

Step 3: 2,3-dimethyl-1-(4-methylbenzyl)-7-(4-trifluoromethylbenzyloxy)-1H-pyrrolo[3,2-b]pyridine hydrochloride In accordance with the same procedures as in Step 2 of Example 33, except for using 7-(4-trifluoromethylbenzyloxy)-2,3-dimethyl-1H-pyrrolo[3,2-b]pyridine prepared in Step 2 and 4-methylbenzyl bromide, the titled compound was obtained as a white solid. (Yield: 88.6%)

$^1$H-NMR (CDCl$_3$) δ8.37 (d, 1H), 7.55 (d, 2H), 7.16 (m, 2H), 7.13 (d, 2H), 6.81 (m, 1H), 6.58 (d, 2H), 5.55 (s, 2H), 5.32 (s, 2H), 2.61 (s, 3H), 2.38 (s, 3H), 2.35 (s, 3H)

Examples 201 to 208

The titled compounds of Examples 201 to 208 were prepared, in accordance with the same procedures as in Step 2 of Example 33, using 7-(4-trifluoromethylbenzyloxy)-2,3-dimethyl-1H-pyrrolo[3,2-b]pyridine prepared in Step 2 of Example 200; and, 3-methoxybenzyl bromide, 2-chlorobenzyl chloride, iodoethane, 4-chlorobenzyl chloride, (bromomethyl)cyclopropane, 4-methoxybenzyl chloride, 3-fluorobenzyl chloride, or 3,4-dichlorobenzyl chloride.

Example 201

1-(3-methoxybenzyl)-2,3-dimethyl-7-(4-trifluoromethylbenzyloxy)-1H-pyrrolo[3,2-b]pyridine hydrochloride $^1$H-NMR (CDCl$_3$) δ8.36 (t, 1H), 7.55 (d, 2H), 7.18 (m, 3H), 6.83 (d, 2H), 6.22 (s, 2H), 5.54 (s, 2H), 5.30 (s, 2H), 3.70 (s, 3H), 2.60 (s, 3H), 2.38 (s, 3H); (Yield: 89.0%)

Example 202

1-(2-chlorobenzyl)-2,3-dimethyl-7-(4-trifluoromethylbenzyloxy)-1H-pyrrolo[3,2-b]pyridine hydrochloride $^1$H-NMR (CDCl$_3$) δ8.39 (d, 1H), 7.54 (d, 2H), 7.37 (d, 1H), 7.11 (m, 3H), 6.83 (m, 2H), 6.03 (d, 1H), 5.61 (s, 2H), 5.26 (s, 2H), 2.62 (s, 3H), 2.37 (s, 3H); (Yield: 75.4%)

Example 203

1-ethyl-2,3-dimethyl-7-(4-trifluoromethylbenzyloxy)-1H-pyrrolo[3,2-b]pyridine hydrochloride $^1$H-NMR (CDCl$_3$) δ8.34 (d, 1H), 7.75 (d, 2H), 7.62 (d, 2H), 6.89 (s, 1H), 5.48 (s, 2H), 4.38 (m, 2H), 2.54 (s, 3H), 2.43 (s, 3H), 1.33 (t, 3H); (Yield: 63.8%)

Example 204

1-(4-chlorobenzyl)-2,3-dimethyl-7-(4-trifluoromethylbenzyloxy)-1H-pyrrolo[3,2-b]pyridine hydrochloride $^1$H-NMR (CDCl$_3$) δ8.37 (d, 1H), 7.60 (d, 2H), 7.38 (m, 2H), 7.24 (m, 2H), 6.86 (m, 1H), 6.60 (d, 2H), 5.50 (s, 2H), 5.31 (s, 2H), 2.60 (s, 3H), 2.37 (s, 3H); (Yield: 85.2%)

Example 205

1-cyclopropylmethyl-2,3-dimethyl-7-(4-trifluoromethylbenzyloxy)-1H-pyrrolo[3,2-b]pyridine hydrochloride $^1$H-NMR (CDCl$_3$) δ8.08 (d, 2H), 7.99 (d, 1H), 7.37 (m, 2H), 6.45 (s, 1H), 5.25 (s, 1H), 4.59 (m, 1H), 4.41 (m, 1H), 4.15 (d, 1H), 2.53 (s, 3H), 2.47 (s, 3H), 1.34 (m, 1H), 0.72 (d, 1H), 0.61 (d, 1H), 0.35 (m, 2H); (Yield: 77.4%)

Example 206

1-(4-methoxybenzyl)-2,3-dimethyl-7-(4-trifluoromethylbenzyloxy)-1H-pyrrolo[3,2-b]pyridine hydrochloride $^1$H-NMR (CDCl$_3$) δ8.36 (d, 1H), 7.58 (d, 2H), 6.94 (m, 3H), 6.84 (m, 2H), 6.79 (m, 2H), 6.60 (d, 2H), 5.52 (s, 2H), 5.29 (s, 2H), 3.78 (s, 3H), 2.60 (s, 3H), 2.38 (s, 3H); (Yield: 65.4%)

Example 207

1-(3-fluorobenzyl)-2,3-dimethyl-7-(4-trifluoromethylbenzyloxy)-1H-pyrrolo[3,2-b]pyridine hydrochloride $^1$H-NMR (CDCl$_3$) δ8.38 (d, 1H), 7.56 (d, 2H), 7.15 (d, 2H), 7.032 (m, 3H), 6.83 (m, 1H), 6.22 (m, 1H), 5.62 (s, 2H), 5.24 (s, 2H), 2.62 (s, 3H), 2.39 (s, 3H); (Yield: 68.7)

Example 208

1-(3,4-dichlorobenzyl)-2,3-dimethyl-7-(4-trifluoromethylbenzyloxy)-1H-pyrrolo[3,2-b]pyridine hydrochloride $^1$H-NMR (CDCl$_3$) δ8.40 (s, 1H), 7.64 (d, 2H), 7.32 (m, 4H), 6.88 (s, 1H), 6.79 (s, 1H), 6.43 (d, 1H), 5.48 (s, 2H), 5.22 (s, 2H), 2.61 (s, 3H), 2.39 (s, 3H); (Yield: 74.2%)

Example 209

1-benzyl-2,3-dimethyl-7-(pyridin-3-ylmethoxy)-1H-pyrrolo[3,2-b]pyridine hydrochloride

Step 1: 4-(pyridin-3-ylmethoxy)-3-nitropyridine

In accordance with the same procedures as in Preparation 2, except for using 4-chloro-3-nitropyridine prepared in Step 1 of Preparation 1 and 3-pyridyl carbinol, the titled compound was obtained as a yellow solid. (Yield: 78.5%)

$^1$H-NMR (CDCl$_3$) δ9.06 (s, 1H), 8.70 (s, 1H), 8.65 (m, 2H), 7.87 (m, 1H), 7.39 (m, 1H), 7.10 (d, 2H), 5.32 (s, 2H)

Step 2: 2,3-dimethyl-7-(pyridin-3-ylmethoxy)-1H-pyrrolo[3,2-b]pyridine

In accordance with the same procedures as in Step 1 of Example 33, except for using 4-(pyridin-3-ylmethoxy)-3-nitropyridine prepared in Step 1, the titled compound was obtained as a white solid. (Yield: 18.4%)

$^1$H-NMR (CDCl$_3$) δ8.74 (s, 1H), 8.64 (s, 1H), 8.30 (s, 1H), 8.04 (brs, 1H), 7.79 (d, 1H), 7.35 (d, 1H), 6.63 (s, 1H), 5.30 (s, 2H), 2.40 (s, 3H), 2.31 (s, 3H)

Step 3: 1-benzyl-2,3-dimethyl-7-(pyridin-3-ylmethoxy)-1H-pyrrolo[3,2-b]pyridine hydrochloride In accordance with the same procedures as in Step 2 of Example 33, except for using 2,3-dimethyl-7-(pyridin-3-ylmethoxy)-1H-pyrrolo[3,2-b]pyridine prepared in Step 2 and benzyl bromide, the titled compound was obtained as a white solid. (Yield: 78.4%)

$^1$H-NMR (DMSO-d$_6$) δ8.59 (s, 2H), 8.37 (s, 1H), 7.78 (s, 1H), 7.53 (s, 1H), 7.21 (s, 1H), 7.10 (s, 3H), 6.64 (s, 2H), 5.57 (s, 2H), 5.47 (s, 2H), 2.25 (s, 3H), 2.14 (s, 3H)

Examples 210 to 214

The titled compounds of Examples 210 to 214 were prepared, in accordance with the same procedures as in Step 2 of Example 33, using 2,3-dimethyl-7-(pyridin-3-ylmethoxy)-1H-pyrrolo[3,2-b]pyridine prepared in Step 2 of Example 209; and, 1-iodopropane, 1-iodo-2-methylpropane, allyl bromide, 2-bromoethyl methyl ether, or (bromomethyl)cyclobutane.

Example 210

2,3-dimethyl-1-propyl-7-(pyridin-3-ylmethoxy)-1H-pyrrolo[3,2-b]pyridine hydrochloride $^1$H-NMR (DMSO-d$_6$) δ8.72 (s, 1H), 8.55 (s, 1H), 8.27 (d, 1H), 8.08 (d, 1H), 7.53 (s, 1H), 7.15 (d, 1H), 5.43 (s, 2H), 3.97 (t, 2H), 2.20 (s, 3H), 2.06 (s, 3H), 1.35 (m, 2H), 0.39 (t, 3H); (Yield: 78.5%)

Example 211

1-isobutyl-2,3-dimethyl-7-(pyridin-3-ylmethoxy)-1H-pyrrolo[3,2-b]pyridine hydrochloride $^1$H-NMR (DMSO-d$_6$) δ8.75 (s, 1H), 8.58 (s, 1H), 8.31 (d, 1H), 8.10 (d, 1H), 7.56 (s, 1H), 7.18 (d, 1H), 5.44 (s, 2H), 3.86 (d, 2H), 2.22 (s, 3H), 2.10 (s, 3H), 1.74 (m, 1H), 0.39 (d, 6H); (Yield: 69.8%)

Example 212

1-allyl-2,3-dimethyl-7-(pyridin-3-ylmethoxy)-1H-pyrrolo[3,2-b]pyridine hydrochloride $^1$H-NMR (DMSO-d$_6$) δ8.92 (s, 1H), 8.79 (s, 1H), 8.51 (d, 1H), 8.31 (s, 1H), 7.80 (s, 1H), 7.37 (s, 1H), 5.97 (m, 1H), 5.370 (s, 2H), 5.08 (d, 1H), 5.01 (s, 2H), 4.56 (s, 1H), 2.50 (s, 3H), 2.32 (s, 3H); (Yield: 57.9%)

Example 213

1-(2-methoxyethyl)-2,3-dimethyl-7-(pyridin-3-ylmethoxy)-1H-pyrrolo[3,2-b]pyridine hydrochloride $^1$H-NMR (DMSO-d$_6$) δ9.00 (s, 1H), 8.84 (s, 1H), 8.49 (d, 1H), 8.43 (d, 1H), 7.88 (s, 1H), 7.37 (d, 1H), 5.71 (s, 2H), 4.49 (s, 2H), 3.50 (d, 2H), 3.12 (s, 3H), 2.44 (s, 3H), 2.31 (s, 3H); (Yield: 78.4%)

Example 214

1-cyclobutylmethyl-2,3-dimethyl-7-(pyridin-3-ylmethoxy)-1H-pyrrolo[3,2-b]pyridine hydrochloride $^1$H-NMR (DMSO-d$_6$) δ8.99 (s, 1H), 8.81 (s, 1H), 8.50 (d, 1H), 8.37 (s, 1H), 7.82 (s, 1H), 7.39 (d, 1H), 5.69 (s, 2H), 4.33 (d, 2H), 2.61 (m, 1H), 2.44 (s, 3H), 2.30 (s, 3H), 1.66 (m, 6H); (Yield: 83.4%)

Example 215

1-benzyl-2,3-dimethyl-7-(pyridin-2-ylmethoxy)-1H-pyrrolo[3,2-b]pyridine hydrochloride

Step 1: 4-(pyridin-2-ylmethoxy)-3-nitropyridine

In accordance with the same procedures as in Preparation 2, except for using 4-chloro-3-nitropyridine prepared in Step 1 of Preparation 1 and 2-pyridyl carbinol, the titled compound was obtained as a yellow solid. (Yield: 68.3%)

$^1$H-NMR (CDCl$_3$) δ9.06 (s, 1H), 8.61 (m, 2H), 7.78 (m, 1H), 7.64 (d, 1H), 7.31 (m, 1H), 7.15 (d, 1H), 5.41 (s, 2H)

Step 2: 2,3-dimethyl-7-(pyridin-2-ylmethoxy)-1H-pyrrolo[3,2-b]pyridine

In accordance with the same procedures as in Step 1 of Example 33, except for using 4-(pyridin-2-ylmethoxy)-3-nitropyridine prepared in Step 1, the titled compound was obtained as a white solid. (Yield: 21.5%)

$^1$H-NMR (CDCl$_3$) δ8.64 (s, 1+1H), 8.26 (d, 1H), 7.73 (t, 1H), 7.48 (d, 1H), 7.29 (s, 1H), 6.63 (d, 1H), 5.40 (s, 2H), 2.43 (s, 3H), 2.33 (s, 3H)

Step 3: 1-benzyl-2,3-dimethyl-7-(pyridin-2-ylmethoxy)-1H-pyrrolo[3,2-b]pyridine hydrochloride In accordance with the same procedures as in Step 2 of Example 33, except for using 2,3-dimethyl-7-(pyridin-2-ylmethoxy)-1H-pyrrolo[3,2-b]pyridine prepared in Step 2 and benzyl bromide, the titled compound was obtained as a white solid. (Yield: 78.4%)

$^1$H-NMR (DMSO-d$_6$) δ8.59 (s, 1H), 8.47 (d, 1H), 7.78 (t, 1H), 7.42 (t, 1H), 7.31 (d, 1H), 7.24 (s, 3H), 7.19 (d, 1H), 6.89 (s, 2H), 5.72 (s, 2H), 5.62 (s, 2H), 2.40 (s, 3H), 2.33 (s, 3H)

Examples 216 AND 217

The titled compounds of Examples 216 and 217 were prepared, in accordance with the same procedures as in Step 2 of Example 33, using 2,3-dimethyl-7-(pyridin-2-ylmethoxy)-1H-pyrrolo[3,2-b]pyridine prepared in Step 2 of Example 215; and, 1-iodopropane or 2-bromoethyl methyl ether.

Example 216

2,3-dimethyl-1-propyl-7-(pyridin-2-ylmethoxy)-1H-pyrrolo[3,2-b]pyridine hydrochloride $^1$H-NMR (DMSO-d$_6$) δ8.59 (s, 1H), 8.38 (d, 1H), 7.90 (t, 1H), 7.62 (d, 1H), 7.41 (s, 1H), 7.27 (d, 1H), 5.59 (s, 2H), 4.21 (t, 2H), 2.37 (s, 3H), 2.22 (s, 3H), 1.57 (m, 2H), 0.61 (t, 3H); (Yield: 63.8%)

Example 217

1-(2-methoxyethyl)-2,3-dimethyl-7-(pyridin-2-ylmethoxy)-1H-pyrrolo[3,2-b]pyridine hydrochloride $^1$H-NMR (DMSO-d$_6$) δ8.65 (s, 1H), 8.44 (d, 1H), 7.96 (t, 1H), 7.67 (d, 1H), 7.47 (s, 1H), 7.32 (d, 1H), 5.69 (s, 2H), 4.55 (s, 2H), 3.60 (s, 2H), 3.19 (s, 3H), 2.45 (s, 3H), 2.29 (s, 3H); (Yield: 79.8%)

Example 218

7-(4-bromobenzyloxy)-2,3-dimethyl-1H-pyrrolo[3,2-b]pyridine

Step 1: 4-bromobenzyloxy-3-nitropyridine

In accordance with the same procedures as in Preparation 2, except for using 4-chloro-3-nitropyridine prepared in Step 1 of Preparation 1 and 4-bromobenzyl alcohol, the titled compound was obtained as a yellow solid. (Yield: 78.9%)

$^1$H-NMR (CDCl$_3$) δ9.04 (s, 1H), 8.62 (d, 1H), 7.56 (d, 2H), 7.34 (d, 2H), 7.04 (d, 1H), 5.26 (s, 2H)

Step 2: 7-(4-bromobenzyloxy)-2,3-dimethyl-1H-pyrrolo[3,2-b]pyridine

In accordance with the same procedures as in Step 1 of Example 33, except for using 4-bromobenzyloxy-3-nitropyridine prepared in Step 1, the titled compound was obtained as a white solid. (Yield: 15.8%)

$^1$H-NMR (CDCl$_3$) δ8.28 (d, 1H), 8.21 (brs, 1H), 7.52 (d, 2H), 7.31 (d, 2H), 6.56 (d, 1H), 5.16 (s, 2H), 2.39 (s, 3H), 2.30 (s, 3H)

Examples 219 to 230

The titled compounds of Examples 219 to 230 were prepared, in accordance with the same procedures as in Step 2 of Example 33, using 7-(4-bromobenzyloxy)-2,3-dimethyl-1H-pyrrolo[3,2-b]pyridine prepared in Step 2 of Example 218; and, benzyl bromide, allyl bromide, 4-fluorobenzyl chloride, 3-fluorobenzyl chloride, 3-methylbenzyl bromide, 4-methylbenzyl bromide, 2-fluorobenzyl bromide, 3-chlorobenzyl bromide, (bromomethyl)cyclobutane, 1-iodo-2-methylpropane, 1-iodopropane, or 2-methoxybenzyl chloride.

Example 219

1-benzyl-7-(4-bromobenzyloxy)-2,3-dimethyl-1H-pyrrolo[3,2-b]pyridine hydrochloride $^1$H-NMR (CDCl$_3$) δ8.35 (t, 1H), 7.43 (d, 1H), 7.29 (m, 3H), 6.91 (d, 2H), 6.81 (d, 1H), 6.67 (d, 2H), 5.57 (s, 2H), 5.20 (s, 2H), 2.60 (s, 3H), 2.32 (s, 3H); (Yield: 48.9%)

Example 220

1-allyl-7-(4-bromobenzyloxy)-2,3-dimethyl-1H-pyrrolo[3,2-b]pyridine hydrochloride $^1$H-NMR (CDCl$_3$) δ8.33 (t, 1H), 7.60 (d, 2H), 7.33 (d, 2H), 6.88 (d, 1H), 5.88 (m, 1H), 5.33 (s, 2H), 5.14 (d, 1H), 4.94 (d, 2H), 4.54 (d, 2H), 2.56 (s, 3H), 2.32 (s, 3H); (Yield: 58.8%)

Example 221

7-(4-bromobenzyloxy)-1-(4-fluorobenzyl)-2,3-dimethyl-1H-pyrrolo[3,2-b]pyridine hydrochloride $^1$H-NMR (CDCl$_3$) δ8.34 (t, 1H), 7.47 (d, 2H), 6.96 (m, 4H), 6.87 (d, 1H), 6.63 (m, 2H), 5.21 (s, 2H), 5.23 (s, 2H), 2.59 (s, 3H), 2.37 (s, 3H); (Yield: 65.3%)

Example 222

7-(4-bromobenzyloxy)-1-(3-fluorobenzyl)-2,3-dimethyl-1H-pyrrolo[3,2-b]pyridine hydrochloride $^1$H-NMR (CDCl$_3$) δ8.36 (t, 1H), 7.47 (d, 2H), 7.22 (m, 1H), 7.01 (m, 3H), 6.90 (d, 1H), 6.41 (t, 2H), 5.53 (s, 2H), 5.22 (s, 2H), 2.60 (s, 3H), 2.38 (s, 3H); (Yield: 78.0%)

Example 223

7-(4-bromobenzyloxy)-2,3-dimethyl-1-(3-methylbenzyl)-1H-pyrrolo[3,2-b]pyridine hydrochloride $^1$H-NMR (DMSO-d$_6$) δ8.29 (d, 1H), 7.31 (d, 2H), 7.06 (d, 1H), 6.92 (m, 3H), 6.85 (m, 1H), 6.48 (s, 1H), 6.32 (d, 1H), 5.40 (s, 2H), 5.27 (s, 2H), 2.19 (s, 3H), 2.12 (s, 3H), 1.99 (s, 3H); (Yield: 63.3%)

Example 224

7-(4-bromobenzyloxy)-2,3-dimethyl-1-(4-methyl-benzyl)-1H-pyrrolo[3,2-b]pyridine hydrochloride $^1$H-NMR (CDCl$_3$) δ8.34 (t, 1H), 7.43 (d, 2H), 7.07 (d, 2H), 6.93 (d, 2H), 6.82 (d, 1H), 6.58 (d, 2H), 5.53 (s, 2H), 5.22 (s, 2H), 2.59 (s, 3H), 2.37 (s, 3H), 2.32 (s, 3H); (Yield: 78.9%)

Example 225

7-(4-bromobenzyloxy)-1-(2-fluorobenzyl)-2,3-dimethyl-1H-pyrrolo[3,2-b]pyridine hydrochloride $^1$H-NMR (CDCl$_3$) δ8.36 (t, 1H), 7.43 (d, 2H), 7.30 (d, 1H), 7.03 (m, 2H), 6.92 (d, 2H), 6.83 (d, 1H), 6.23 (t, 1H), 5.61 (s, 2H), 521 (s, 2H), 2.60 (s, 3H), 2.38 (s, 3H); (Yield: 68.0%)

Example 226

7-(4-bromobenzyloxy)-1-(3-chlorobenzyl)-2,3-dimethyl-1H-pyrrolo[3,2-b]pyridine hydrochloride $^1$H-NMR (CDCl$_3$) δ8.36 (t, 1H), 7.49 (d, 1H), 7.27 (s, 1H), 7.20 (t, 1H), 6.98 (d, 2H), 6.88 (d, 1H), 6.71 (s, 1H), 6.46 (d, 1H), 5.54 (s, 2H), 5.24 (s, 2H), 2.60 (s, 3H), 2.33 (s, 3H); (Yield: 68.8%)

Example 227

7-(4-bromobenzyloxy)-1-cyclobutylmethyl-2,3-dimethyl-1H-pyrrolo[3,2-b]pyridine hydrochloride $^1$H-NMR (CDCl$_3$) δ8.34 (brs, 1H), 7.63 (d, 2H), 7.38 (d, 2H), 6.88 (d, 1H), 5.34 (s, 2H), 4.30 (d, 2H), 2.54 (s, 3H), 2.38 (s, 3H), 1.77 (m, 3H), 1.66 (m, 4H); (Yield: 55.4%)

Example 228

7-(4-bromobenzyloxy)-1-isobutyl-2,3-dimethyl-1H-pyrrolo[3,2-b]pyridine hydrochloride $^1$H-NMR (CDCl$_3$) δ8.39 (t, 1H), 7.63 (d, 2H), 7.38 (d, 2H), 6.96 (d, 1H), 5.37 (s, 2H), 4.04 (d, 2H), 2.55 (s, 3H), 2.42 (s, 3H), 1.81 (m, 1H), 0.71 (d, 6H); (Yield: 70.0%)

Example 229

7-(4-bromobenzyloxy)-2,3-dimethyl-1-propyl-1H-pyrrolo[3,2-b]pyridine hydrochloride $^1$H-NMR (CDCl$_3$) δ8.33 (t, 1H), 7.61 (d, 2H), 7.38 (d, 2H), 7.01 (d, 1H), 5.38 (s, 2H), 4.31 (t, 2H), 2.52 (s, 3H), 2.41 (s, 3H), 1.67 (m, 2H), 0.75 (t, 3H); (Yield: 65.5%)

Example 230

7-(4-bromobenzyloxy)-1-(2-methoxybenzyl)-2,3-dimethyl-1H-pyrrolo[3,2-b]pyridine hydrochloride $^1$H-NMR (CDCl$_3$) δ8.35 (t, 1H), 7.41 (d, 2H), 6.84 (m, 6H), 5.97 (d, 1H), 5.68 (s, 2H), 5.14 (s, 2H), 3.75 (s, 3H), 2.60 (s, 3H), 2.25 (s, 3H); (Yield: 78.0%)

Example 231

1-benzyl-7-(4-isopropylbenzyloxy)-2,3-dimethyl-1H-pyrrolo[3,2-b]pyridine hydrochloride Step 1: 4-isopropylbenzyloxy-3-nitropyridine In accordance with the same procedures as in Preparation 2, except for using 4-chloro-3-nitropyridine prepared in Step 1 of Preparation 1 and 4-isopropylbenzyl alcohol, the titled compound was obtained as a white solid. (Yield: 67.8%)
$^1$H-NMR (CDCl$_3$) δ9.02 (s, 1H), 8.59 (d, 1H), 7.37 (d, 2H), 7.28 (d, 2H), 7.07 (d, 1H), 5.28 (s, 2H), 2.90 (m, 1H), 1.26 (d, 6H)

Step 2: 7-(4-isopropylbenzyloxy)-2,3-dimethyl-1H-pyrrolo[3,2-b]pyridine

In accordance with the same procedures as in Step 1 of Example 33, except for using 4-isopropylbenzyloxy-3-nitropyridine prepared in Step 1, the titled compound was obtained as a white solid. (Yield: 25.8%)
$^1$H-NMR (CDCl$_3$) δ8.31 (d, 1H), 7.20 (d, 2H), 7.05 (d, 2H), 6.82 (d, 1H), 5.23 (s, 2H), 2.90 (m, 1H), 2.54 (s, 3H), 2.35 (s, 3H), 1.24 (d, 6H)

Step 3: 1-benzyl-7-(4-isopropylbenzyloxy)-2,3-dimethyl-1H-pyrrolo[3,2-b]pyridine hydrochloride In accordance with the same procedures as in Step 2 of Example 33, except for using 7-(4-isopropylbenzyloxy)-2,3-dimethyl-1H-pyrrolo[3,2-b]pyridine prepared in Step 2 and benzyl bromide, the titled compound was obtained as a white solid. (Yield: 78.5%)
$^1$H-NMR (CDCl$_3$) δ8.32 (t, 1H), 7.27 (m, 3H), 7.16 (d, 2H), 7.00 (d, 2H), 6.83 (d, 1H), 6.67 (m, 2H), 5.57 (s, 2H), 5.22 (s, 2H), 2.91 (m, 1H), 2.59 (s, 3H), 2.37 (s, 3H), 1.26 (d, 6H)

Examples 232 to 240

The titled compounds of Examples 232 to 240 were prepared, in accordance with the same procedures as in Step 2 of Example 33, using 7-(4-isopropylbenzyloxy)-2,3-dimethyl-1H-pyrrolo[3,2-b]pyridine prepared in Step 2 of Example 231; and, 4-fluorobenzyl chloride, 3-methylbenzyl chloride, 3-fluorobenzyl chloride, 4-methylbenzyl chloride, 2-methoxybenzyl bromide, 3-chlorobenzyl bromide, 2-fluorobenzyl bromide, (bromomethyl)cyclobutane, or 1-iodopropane.

Example 232

1-(4-fluorobenzyl)-7-(4-isopropylbenzyloxy)-2,3-dimethyl-1H-pyrrolo[3,2-b]pyridine hydrochloride $^1$H-NMR (CDCl$_3$) δ8.34 (t, 1H), 7.20 (d, 2H), 7.05 (d, 2H), 6.93 (t, 2H), 6.86 (d, 1H), 6.62 (m, 2H), 5.52 (s, 2H), 5.23 (s, 2H), 2.93 (m, 1H), 2.58 (s, 3H), 2.37 (s, 3H), 1.27 (d, 6H); (Yield: 85.4%)

Example 233

7-(4-isopropylbenzyloxy)-2,3-dimethyl-1-(3-methyl-benzyl)-1H-pyrrolo[3,2-b]pyridine hydrochloride $^1$H-NMR (CDCl$_3$) δ8.32 (t, 1H), 7.17 (m, 3H), 7.10 (d, 1H), 7.02 (d, 2H), 6.83 (d, 1H), 6.50 (s, 1H), 6.47 (d, 1H), 5.55

(s, 2H), 5.24 (s, 2H), 2.92 (m, 1H), 2.59 (s, 3H), 2.37 (s, 3H), 2.26 (s, 3H), 1.26 (d, 6H); (Yield: 65.7%)

Example 234

1-(3-fluorobenzyl)-7-(4-isopropylbenzyloxy)-2,3-dimethyl-1H-pyrrolo[3,2-b]pyridine hydrochloride $^1$H-NMR (CDCl$_3$) δ8.35 (t, 1H), 7.19 (m, 3H), 7.01 (m, 3H), 6.86 (d, 1H), 6.39 (m, 2H), 5.53 (s, 2H), 5.21 (s, 2H), 2.92 (m, 1H), 2.59 (s, 3H), 2.37 (s, 3H), 1.25 (d, 6H); (Yield: 78.4%)

Example 235

7-(4-isopropylbenzyloxy)-2,3-dimethyl-1-(4-methylbenzyl)-1H-pyrrolo[3,2-b]pyridine hydrochloride $^1$H-NMR (CDCl$_3$) δ8.32 (t, 1H), 7.17 (d, 2H), 7.07 (d, 2H), 7.01 (d, 2H), 6.83 (d, 1H), 6.59 (d, 2H), 5.54 (s, 2H), 5.24 (s, 2H), 2.92 (m, 1H), 2.58 (s, 3H), 2.37 (s, 3H), 2.33 (s, 3H), 1.28 (d, 6H); (Yield: 84.2%)

Example 236

7-(4-isopropylbenzyloxy)-1-(2-methoxybenzyl)-2,3-dimethyl-1H-pyrrolo[3,2-b]pyridine hydrochloride $^1$H-NMR (CDCl$_3$) δ8.32 (t, 1H), 7.29 (m, 1H), 7.12 (d, 2H), 6.89 (m, 3H), 6.79 (m, 2H), 6.01 (d, 1H), 5.55 (s, 2H), 5.18 (s, 2H), 3.73 (s, 3H), 2.89 (m, 1H), 2.59 (s, 3H), 2.33 (s, 3H), 1.24 (d, 6H); (Yield: 65.7%)

Example 237

1-(3-chlorobenzyl)-7-(4-isopropylbenzyloxy)-2,3-dimethyl-1H-pyrrolo[3,2-b]pyridine hydrochloride $^1$H-NMR (CDCl$_3$) δ8.36 (t, 1H), 7.20 (d, 2H), 7.05 (d, 2H), 6.93 (t, 2H), 6.86 (d, 1H), 6.62 (m, 2H), 5.52 (s, 2H), 5.23 (s, 2H), 2.91 (m, 1H), 2.58 (s, 3H), 2.37 (s, 3H), 1.27 (d, 6H); (Yield: 74.5%)

Example 238

1-(2-fluorobenzyl)-7-(4-isopropylbenzyloxy)-2,3-dimethyl-1H-pyrrolo[3,2-b]pyridine hydrochloride $^1$H-NMR (CDCl$_3$) δ8.34 (t, 1H), 7.35-6.96 (m, 7H), 6.84 (d, 1H), 6.23 (t, 1H), 5.63 (s, 2H), 5.23 (s, 2H), 2.88 (m, 1H), 2.59 (s, 3H), 2.36 (s, 3H), 1.25 (d, 6H); (Yield: 63.8%)

Example 239

1-cyclobutylmethyl-7-(4-isopropylbenzyloxy)-2,3-dimethyl-1H-pyrrolo[3,2-b]pyridine hydrochloride $^1$H-NMR (CDCl$_3$) δ8.32 (t, 1H), 7.40 (d, 2H), 7.33 (d, 2H), 6.88 (d, 1H), 5.34 (s, 2H), 4.29 (d, 1H), 2.98 (m, 1H), 2.63 (m, 1H), 2.53 (s, 3H), 2.40 (s, 3H), 1.77-1.56 (m, 7H), 1.28 (d, 6H); (Yield: 81.0%)

Example 240

7-(4-isopropylbenzyloxy)-1-propyl-2,3-dimethyl-1H-pyrrolo[3,2-b]pyridine hydrochloride $^1$H-NMR (CDCl$_3$) δ8.32 (t, 1H), 7.38 (d, 2H), 7.30 (d, 2H), 6.88 (d, 1H), 5.33 (s, 2H), 4.20 (t, 2H), 2.97 (m, 1H), 2.53 (s, 3H), 2.39 (s, 3H), 1.68 (m, 2H), 1.28 (d, 6H), 0.71 (t, 3H); (Yield: 78.5%)

Example 241

1-benzyl-7-(4-fluorophenoxy)-2,3-dimethyl-1H-pyrrolo[3,2-b]pyridine hydrochloride

Step 1: 4-fluorophenoxy-3-nitropyridine

Sodium hydride (7.2 g, 180.4 mmol) was slowly added at 0° C. to a solution of 4-fluorophenol (17.11 g, 152.6 mmol) in 200 ml of N,N-dimethylformamide and then the reaction mixture was stirred for 30 minutes at room temperature. 4-Chloro-3-nitropyridine (22.0 g, 138.8 mmol) prepared in Step 1 of Preparation 1 was added at 0° C. to the reaction mixture, which was stirred for 1 hour at room temperature, diluted with 200 ml of ethyl acetate, and then washed with 200 ml of water three times. The separated organic layer was dried on anhydrous magnesium sulfate and then concentrated under reduced pressure to give the titled compound as a pale yellow solid (25.2 g, 76.8%).

$^1$H-NMR (CDCl$_3$) δ9.13 (s, 1H), 8.57 (d, 1H), 7.15 (m, 4H), 6.76 (d, 1H)

Step 2: 7-(4-fluorophenoxy)-2,3-dimethyl-1H-pyrrolo[3,2-b]pyridine

In accordance with the same procedures as in Step 1 of Example 33, except for using 4-fluorophenoxy-3-nitropyridine prepared in Step 1, the titled compound was obtained as a white solid. (Yield: 18.5%)

$^1$H-NMR (CDCl$_3$) δ8.22 (d, 1H), 7.99 (br s, 1H), 7.08 (m, 4H), 6.38 (d, 1H), 2.55 (s, 3H), 2.32 (s, 3H)

Step 3: 1-benzyl-7-(4-fluorophenoxy)-2,3-dimethyl-1H-pyrrolo[3,2-b]pyridine hydrochloride In accordance with the same procedures as in Step 2 of Example 33, except for using 7-(4-fluorophenoxy)-2,3-dimethyl-1H-pyrrolo[3,2-b]pyridine prepared in Step 2 and benzyl bromide, the titled compound was obtained as a white solid. (Yield: 63.8%)

$^1$H-NMR (CDCl$_3$) δ8.27 (t, 1H), 7.31 (m, 3H), 7.13 (t, 2H), 6.87 (m, 4H), 6.44 (d, 1H), 5.71 (s, 2H), 2.64 (s, 3H), 2.47 (s, 3H)

Examples 242 AND 243

The titled compounds of Examples 242 and 243 were prepared, in accordance with the same procedures as in Step 2 of Example 33, using 7-(4-fluorophenoxy)-2,3-dimethyl-1H-pyrrolo[3,2-b]pyridine prepared in Step 2 of Example 241; and, allyl bromide or (bromomethyl)cyclobutane.

Example 242

1-allyl-7-(4-fluorophenoxy)-2,3-dimethyl-1H-pyrrolo[3,2-b]pyridine hydrochloride $^1$H-NMR (CDCl$_3$) δ8.25 (t, 1H), 7.20-7.12 (m, 4H), 6.47 (d, 1H), 6.04 (m, 1H), 5.22 (d, 1H), 5.10 (d, 2H), 4.72 (d, 1H), 2.61 (s, 3H), 2.46 (s, 3H); (Yield: 73.3%)

Example 243

1-cyclobutylmethyl-7-(4-fluorophenoxy)-2,3-dimethyl-1H-pyrrolo[3,2-b]pyridine hydrochloride $^1$H-NMR (CDCl$_3$) δ8.22 (t, 1H), 7.23-7.17 (m, 4H), 6.42 (d, 1H), 4.50 (d, 2H), 2.74 (m, 1H), 2.58 (s, 3H), 2.48 (s, 3H), 1.91-1.76 (m, 7H); (Yield: 83.4%)

Example 244

(2,3-dimethyl-1-propyl-1H-pyrrolo[3,2-b]pyridin-7-yl)-(4-fluorobenzyl)carbamic acid tert-butyl ester hydrochloride (2,3-dimethyl-1H-pyrrolo[3,2-b]pyridin-7-yl)-(4-fluorobenzyl)carbamic acid tert-butyl ester (20 mg, 0.089 mmol) prepared in Preparation 3, potassium tert-butoxide (10.6 mg, 0.143 mmol), and a catalytic amount of 18-crown-6 were added to anhydrous tetrahydrofuran (2 ml). 1-Iodopropane (0.089 ml, 0.130 mmol) was added to the reaction mixture, which was then stirred for 12 hours at room temperature. The reaction mixture was concentrated under reduced pressure. The resulting residue was purified with silica gel column chromatography (ethyl acetate/methylene chloride/methanol=10/10/1, (v/v/v)), dissolved in ethyl acetate (1 ml), and then saturated with hydrochloric acid gas. The resulting precipitate was filtered to give the titled compound as a white solid (16.3 mg, 58.6%).

$^1$H-NMR (CDCl$_3$) δ8.32 (d, 1H), 7.38 (m, 1H), 7.15 (d, 2H), 7.03 (d, 2H), 5.29 (m, 2H), 4.35 (m, 2H), 3.40 (m, 2H), 3.16 (s, 3H), 2.53 (s, 3H), 2.48 (s, 3H), 1.41 (s, 9H)

Examples 245 to 253

The titled compounds of Examples 245 to 253 were prepared, in accordance with the same procedures as in Example 244, using (2,3-dimethyl-1H-pyrrolo[3,2-b]pyridin-7-yl)-(4-fluorobenzyl)carbamic acid tert-butyl ester prepared in Preparation 3; and, 2-bromoethyl methyl ether, (bromomethyl)cyclopropane, iodoethane, benzyl bromide, 3-fluorobenzyl chloride, 3-methoxybenzyl chloride, 4-methoxybenzyl chloride, 3-methylbenzyl chloride, or 4-methylbenzyl chloride.

Example 245

[2,3-dimethyl-1-(2-methoxyethyl)-1H-pyrrolo[3,2-b]pyridin-7-yl]-(4-fluorobenzyl)carbamic acid tert-butyl ester hydrochloride $^1$H-NMR (CDCl$_3$) δ8.32 (d, 1H), 7.38 (m, 1H), 7.15 (d, 2H), 7.03 (d, 2H), 5.29 (m, 2H), 4.35 (m, 2H), 3.40 (m, 2H), 3.16 (s, 3H), 2.53 (s, 3H), 2.48 (s, 3H), 1.41 (s, 9H); (Yield: 75.8%)

Example 246

(2,3-dimethyl-1-cyclopropylmethyl-1H-pyrrolo[3,2-b]pyridin-7-yl)-(4-fluorobenzyl)carbamic acid tert-butyl ester hydrochloride $^1$H-NMR (CDCl$_3$) δ8.27 (t, 1H), 7.06 (m, 2H), 6.98 (m, 2H), 6.68 (m, 1H), 5.32 (m, 2H), 4.20 (m, 2H), 2.64 (s, 3H), 2.55 (s, 3H), 1.42 (s, 9H), 0.97 (m, 1H), 0.55 (m, 2H), 0.28 (m, 2H); (Yield: 63.8%)

Example 247

(2,3-dimethyl-1-ethyl-1H-pyrrolo[3,2-b]pyridin-7-yl)-(4-fluorobenzyl)carbamic acid tert-butyl ester hydrochloride $^1$H-NMR (CDCl$_3$) δ8.29 (m, 1H), 7.11 (t, 2H), 6.99 (t, 2H), 6.70 (m, 1H), 5.28 (m, 2H), 4.28 (m, 2H), 4.17 (m, 2H), 2.62 (s, 3H), 2.50 (s, 3H), 1.34 (s, 9H), 1.18 (t, 3H); (Yield: 58.4%)

Example 248

1-benzyl-(2,3-dimethyl-1H-pyrrolo[3,2-b]pyridin-7-yl)-(4-fluorobenzyl)carbamic acid tert-butyl ester hydrochloride $^1$H-NMR (CDCl$_3$) δ8.31 (t, 1H), 7.30 (m, 2H), 7.02 (m, 2H), 6.98 (m, 2H), 6.62 (m, 3H), 5.45 (m, 4H), 2.62 (s, 3H), 2.38 (s, 3H), 1.41 (s, 9H); (Yield: 75.0%)

Example 249

[2,3-dimethyl-1-(3-fluorobenzyl)-1H-pyrrolo[3,2-b]pyridin-7-yl]-(4-fluorobenzyl)carbamic acid tert-butyl ester hydrochloride $^1$H-NMR (CDCl$_3$) δ8.35 (t, 1H), 7.00 (m, 3H), 6.91 (m, 2H), 6.70 (m, 1H), 6.37 (m, 2H), 5.48 (m, 4H), 2.67 (s, 3H), 2.36 (s, 3H), 1.41 (s, 9H); (Yield: 63.3%)

Example 250

[2,3-dimethyl-1-(3-methoxybenzyl)-1H-pyrrolo[3,2-b]pyridin-7-yl]-(4-fluorobenzyl)carbamic acid tert-butyl ester hydrochloride $^1$H-NMR (CDCl$_3$) δ8.31 (t, 1H), 7.22 (t, 1H), 7.02 (m, 2H), 6.92 (m, 2H), 6.80 (d, 1H), 6.66 (m, 1H), 6.17 (s, 2H), 5.44 (m, 2H), 4.96 (br, s, 2H), 3.73 (s, 3H), 2.66 (s, 3H), 2.38 (s, 3H), 1.34 (s, 9H); (Yield: 58.8%)

Example 251

[2,3-dimethyl-1-(4-methoxybenzyl)-1H-pyrrolo[3,2-b]pyridin-7-yl]-(4-fluorobenzyl)carbamic acid tert-butyl ester hydrochloride $^1$H-NMR (CDCl$_3$) δ8.31 (t, 1H), 7.03 (m, 2H), 6.99 (m, 2H), 6.81 (m, 3H), 6.55 (d, 2H), 5.43 (m, 4H), 3.79 (s, 3H), 2.55 (s, 3H), 2.40 (s, 3H), 1.30 (s, 9H); (Yield: 75.0%)

Example 252

[2,3-dimethyl-1-(3-methylbenzyl)-1H-pyrrolo[3,2-b]pyridin-7-yl]-(4-fluorobenzyl)carbamic acid tert-butyl ester hydrochloride $^1$H-NMR (CDCl$_3$) δ 8.31 (t, 1H), 7.18 (m, 1H), 7.15 (m, 1H), 7.09 (m, 2H), 6.96 (m, 2H), 6.64 (m, 1H), 6.44 (s, 1H), 6.37 (m, 1H), 5.50 (m, 4H), 2.63 (s, 3H), 2.41 (s, 3H), 2.24 (s, 3H), 1.31 (s, 9H); (Yield: 63.8%)

Example 253

[2,3-dimethyl-1-(4-methylbenzyl)-1H-pyrrolo[3,2-b]pyridin-7-yl]-(4-fluorobenzyl)carbamic acid tert-butyl ester hydrochloride $^1$H-NMR (CDCl$_3$) δ 8.30 (t, 1H), 7.09 (d, 2H), 7.02 (m, 3H), 6.91 (t, 2H), 6.64 (d, 2H), 5.45 (m, 4H), 2.56 (s, 3H), 2.41 (s, 3H), 2.34 (s, 3H), 1.16 (s, 9H); (Yield: 61.0%)

Example 254

N-(1-allyl-2,3-dimethyl-1H-pyrrolo[3,2-b]pyridin-7-yl)-4-fluorobenzylamine hydrochloride Step 1: (1-allyl-2,3-dimethyl-1H-pyrrolo[3,2-b]pyridin-7-yl)-(4-fluorobenzyl)carbamic acid tert-butyl ester hydrochloride In accordance with the same procedures as in Example 244, except for using (2,3-dimethyl-1H-pyrrolo[3,2-b]pyridin-7-yl)-(4-fluorobenzyl)carbamic acid tert-butyl ester prepared in Preparation 3 and allyl bromide, the titled compound was obtained as a white solid. (Yield: 88.6%) The product was used in the subsequent reaction without further purification.

Step 2: N-(1-allyl-2,3-dimethyl-1H-pyrrolo[3,2-b]pyridin-7-yl)-4-fluorobenzylamine hydrochloride A solution of (1-allyl-2,3-dimethyl-1H-pyrrolo[3,2-b]pyridin-7-yl)-(4-fluorobenzyl)carbamic acid tert-butyl ester hydrochloride (101.3 mg) prepared in Step 1 in ethyl acetate (10 ml) was saturated with hydrochloric acid gas and then stirred for 1 hour at room temperature. The resulting precipitate was filtered and then dried to give the titled compound as a white solid (35.3 mg, 44.1%).

$^1$H-NMR (CDCl$_3$) δ 7.91 (t, 1H), 7.11 (m, 2H), 6.48 (s, 1H), 6.48 (m, 1H), 6.35 (m, 1H), 6.11 (m, 1H), 5.26 (d, 1H), 5.05 (s, 2H), 4.71 (d, 1H), 4.56 (d, 2H), 2.42 (s, 3H), 2.28 (s, 3H)

Examples 255 to 263

The titled compounds of Examples 255 to 263 were prepared, in accordance with the same procedures as in Example 244 and/or Step 2 of Example 254, using (2,3-dimethyl-1H-pyrrolo[3,2-b]pyridin-7-yl)-(4-fluorobenzyl)carbamic acid tert-butyl ester prepared in Preparation 3; and, (bromomethyl)cyclopropane, 2-bromoethyl methyl ether, 3-methoxybenzyl bromide, 4-methoxybenzyl bromide, iodoethane, 1-iodopropane, benzyl bromide, 3-fluorobenzyl chloride, or 4-methylbenzyl chloride.

Example 255

N-(1-cyclopropylmethyl-2,3-dimethyl-1H-pyrrolo[3,2-b]pyridin-7-yl)-4-fluorobenzylamine hydrochloride $^1$H-NMR (CDCl$_3$) δ 7.87 (t, 1H), 7.38 (m, 2H), 7.08 (t, 2H), 6.59 (s, 1H), 6.27 (d, 1H), 4.63 (d, 2H), 4.39 (d, 2H), 2.37 (s, 3H), 2.32 (s, 3H), 1.04 (m, 1H), 0.54 (m, 2H), 0.24 (m, 2H); (Yield: 53.8%)

Example 256

N-[1-(2-methoxyethyl)-2,3-dimethyl-1H-pyrrolo[3,2-b]pyridin-7-yl]-4-fluorobenzylamine hydrochloride $^1$H-NMR (CDCl$_3$) δ 8.04 (t, 1H), 7.71 (t, 1H), 7.34 (m, 2H), 7.10 (t, 2H), 6.40 (d, 1H), 4.49 (d, 2H), 4.39 (t, 2H), 3.75 (t, 2H), 3.19 (s, 3H), 2.47 (s, 3H), 2.35 (s, 3H); (Yield: 48.3%)

Example 257

N-[1-(3-methoxybenzyl)-2,3-dimethyl-1H-pyrrolo[3,2-b]pyridin-7-yl]-4-fluorobenzylamine hydrochloride $^1$H-NMR (CDCl$_3$) δ 8.02 (s, 1H), 7.20 (t, 1H), 6.95 (t, 2H), 6.85 (m, 2H), 6.37 (d, 2H), 6.25 (s, 1H), 5.60 (s, 1H), 5.49 (s, 2H), 4.27 (s, 2H), 3.65 (s, 3H), 2.53 (s, 3H), 2.40 (s, 3H); (Yield: 55.1%)

Example 258

N-[1-(4-methoxybenzyl)-2,3-dimethyl-1H-pyrrolo[3,2-b]pyridin-7-yl]-4-fluorobenzylamine hydrochloride $^1$H-NMR (CDCl$_3$) δ 7.94 (s, 1H), 6.93 (t, 2H), 6.85 (m, 2H), 6.76 (s, 3H), 6.18 (s, 1H), 5.89 (s, 1H), 5.51 (s, 2H), 4.29 (s, 2H), 3.78 (s, 3H), 2.51 (s, 3H), 2.40 (s, 3H); (Yield: 44.2%)

Example 259

N-(1-ethyl-2,3-dimethyl-1H-pyrrolo[3,2-b]pyridin-7-yl)-4-fluorobenzylamine hydrochloride $^1$H-NMR (CDCl$_3$) δ 7.77 (s, 1H), 7.34 (s, 2H), 7.03 (t, 2H), 6.87 (s, 1H), 6.19 (s, 1H), 4.66 (s, 2H), 4.52 (s, 2H), 2.35 (s, 3H), 2.34 (s, 3H), 1.28 (t, 3H); (Yield: 65.3%)

Example 260

N-(2,3-dimethyl-1-propyl-1H-pyrrolo[3,2-b]pyridin-7-yl)-4-fluorobenzylamine hydrochloride $^1$H-NMR (CDCl$_3$) δ 7.85 (t, 1H), 7.36 (m, 2H), 7.07 (t, 2H), 6.36 (s, 1H), 6.21 (d, 1H), 4.60 (d, 2H), 4.30 (t, 2H), 2.38 (s, 3H), 2.33 (s, 3H), 1.72 (m, 2H), 0.84 (t, 3H); (Yield: 70.8%)

Example 261

N-(1-benzyl-2,3-dimethyl-1H-pyrrolo[3,2-b]pyridin-7-yl)-4-fluorobenzylamine hydrochloride H-NMR (CDCl$_3$) δ 8.00 (t, 1H), 7.33 (m, 2H), 6.93 (t, 2H), 6.81 (m, 4H), 6.23 (d, 1H), 5.60 (m, 1H), 5.53 (s, 2H), 4.26 (d, 2H), 2.54 (s, 3H), 2.40 (s, 3H); (Yield: 89.3%)

Example 262

N-[1-(3-fluorobenzyl)-2,3-dimethyl-1H-pyrrolo[3,2-b]pyridin-7-yl]-4-fluorobenzylamine hydrochloride $^1$H-NMR (CDCl$_3$) δ7.88 (s, 1H), 7.21 (m, 1H), 6.99 (t, 1H), 6.91 (t, 2H), 6.83 (m, 1H), 6.65 (d, 1H), 6.50 (d, 1H), 6.23 (s, 1H), 6.14 (s, 1H), 5.70 (s, 2H), 4.35 (s, 2H), 2.49 (s, 3H), 2.39 (s, 3H); (Yield: 77.5%)

Example 263

N-[1-(4-methylbenzyl)-2,3-dimethyl-1H-pyrrolo[3,2-b]pyridin-7-yl]-4-fluorobenzylamine hydrochloride $^1$H-NMR (CDCl$_3$) δ7.97 (s, 1H), 7.07 (d, 2H), 6.92 (t, 2H), 6.81 (d, 2H), 6.73 (d, 2H), 6.20 (s, 1H), 5.75 (s, 1H), 5.51 (s, 2H), 4.27 (s, 2H), 2.53 (s, 3H), 2.40 (s, 3H), 2.34 (s, 3H); (Yield: 69.3%)

Example 264

1-benzyl-7-(4-fluorobenzyloxy)-2,3,5,6-tetramethyl-1H-pyrrolo[3,2-b]pyridine hydrochloride

Step 1: 2,3-dimethyl-4-nitropyridin-N-oxide

30% hydrogen peroxide (100 ml) was added to a solution of 2,3-lutidine (2 g) in 50 ml of acetic acid, which was stirred for 12 hours at 90° C., and then the reaction mixture was concentrated under reduced pressure. The resulting residue was added to a mixture (30 ml) of concentrated sulfuric acid and nitric acid (7:3). The reaction mixture was refluxed under stirring for 3.5 hours, cooled to room temperature, and then added to ice water. The reaction mixture was alkalized with a sodium hydroxide solution, extracted with methylene chloride, dried on anhydrous sodium sulfate, and then concentrated under reduced pressure. The resulting residue was recrystallized with ethyl alcohol to give 2.4 g of the titled compound as a pale yellow solid.

Step 2: 2,3-dimethyl-4-nitropyridine 2,3-Dimethyl-4-nitropyridin-N-oxide (75.6 g, 0.45 mol) prepared in Step 1 was dissolved in 300 ml of methylene chloride. A solution of phosphorus trichloride (44 ml) in methylene chloride (60 ml) was slowly added to the solution for 30 minutes at −15° C.~−20° C. The reaction mixture was stirred for 15 minutes at the same temperature and further stirred for 15 minutes at room temperature. The reaction mixture was cooled to −78° C. 50 ml of water was added to the reaction mixture, which was neutralized with a sodium hydroxide solution and then extracted with methylene chloride. The separated organic layer was dried on anhydrous magnesium sulfate and then concentrated under reduced pressure to give the titled compound as a pale yellow solid (65 g, 95%).

$^1$H-NMR (CDCl$_3$) δ2.43 (s, 3H), 2.66 (s, 3H), 7.43 (d, 1H), 8.55 (d, 1H)

Step 3: 2,3-dimethyl-4-hydroxy-5-nitropyridine

Anhydrous potassium acetate (49 g, 0.5 mol) was added to a solution of 2,3-dimethyl-4-nitropyridine (45.6 g, 0.3 mol) prepared in Step 2 in 300 ml of acetic anhydride and then refluxed under stirring for 16 hours. The reaction mixture was cooled to room temperature and then 400 ml of anhydrous ether was added thereto. The reaction mixture was stirred for 1 hour, filtered with Celite, and then concentrated under reduced pressure to give 4-acetoxy-2,3-dimethylpyridine (45 g, 91%). The resulting residue was added to 250 ml of water, refluxed under stirring for 4 hours, and then left overnight at room temperature. The reaction mixture was concentrated under reduced pressure to give 32.6 g of 2,3-dimethyl-4-hydroxypyridine as a liquid form. The liquid product was dissolved in 120 ml of concentrated sulfuric acid and heated to 60° C. A mixture of 90% nitric acid (40 ml) and sulfuric acid (30 ml) was slowly added to the reaction mixture for 45 minutes, while maintaining the temperature at 60-65° C. The reaction mixture was heated for 2 hours at 65° C. and then for 30 minutes at 75° C. The reaction mixture was cooled to room temperature and then added to ice water. The resulting solution was brought to pH 5~6 with ammonium hydroxide to give a pale yellow solid. The resulting solid was filtered, washed with cold water, and then dried at 80~90° C. to give 34.5 g of the titled compound.

$^1$H-NMR (CDCl$_3$) δ2.54 (s, 3H), 2.87 (s, 3H), 9.35 (s, 1H)

Step 4: 2,3-dimethyl-4-chloro-5-nitropyridine 2,3-Dimethyl-4-hydroxy-5-nitropyridine (26.8 g, 0.16 mol) prepared in Step 3 was added to 85 ml of phosphorus oxychloride. Phosphorus pentachloride (33.3 g, 0.16 mol) was added to the reaction mixture, which was then refluxed under stirring for 2 hours. The reaction mixture was left overnight at room temperature, added to ice water, brought to pH 5 with 28% ammonium hydroxide, and then extracted with ether. The separated organic layer was dried on anhydrous magnesium sulfate and then concentrated to give 28.3 g of the titled compound.

$^1$H-NMR (CDCl$_3$) δ2.47 (s, 3H), 2.66 (s, 3H), 8.77 (s, 1H)

Step 5: 4-(4-fluorobenzyloxy)-2,3-dimethyl-5-nitropyridine

In accordance with the same procedures as in Preparation 2, except for using 2,3-dimethyl-4-chloro-5-nitropyridine (1.0 g, 5.36 mmol) prepared in Step 4, the titled compound was obtained as pale yellow oil. (Yield: 85.4%)

$^1$H-NMR (CDCl$_3$) δ8.80 (s, 1H), 7.43 (m, 2H), 7.04 (m, 2H), 4.99 (s, 2H), 2.56 (s, 3H), 2.19 (s, 3H)

Step 6: 7-(4-fluorobenzyloxy)-2,3,5,6-tetramethyl-1H-pyrrolo[3,2-b]pyridine

In accordance with the same procedures as in Step 1 of Example 33, except for using 4-(4-fluorobenzyloxy)-2,3-dimethyl-5-nitropyridine prepared in Step 5, the titled compound was obtained as a white solid. (Yield: 23.4%)

$^1$H-NMR (CDCl$_3$) δ7.31 (m, 2H), 6.67 (m, 2H), 5.48 (s, 2H), 4.78 (s, 2H), 3.04 (s, 3H), 2.70 (s, 3H), 2.33 (s, 3H), 2.25 (s, 3H)

Step 7: 1-benzyl-7-(4-fluorobenzyloxy)-2,3,5,6-tetramethyl-1H-pyrrolo[3,2-b]pyridine hydrochloride In accordance with the same procedures as in Step 2 of Example 33, except for using 7-(4-fluorobenzyloxy)-2,3,5,6-tetramethyl-1H-pyrrolo[3,2-b]pyridine prepared in Step 6, the titled compound was obtained as a white solid. (Yield: 85.1%)

¹H-NMR (CDCl₃) δ7.27 (m, 3H), 7.09 (m, 4H), 6.67 (m, 2H), 5.499 (s, 2H), 4.77 (s, 2H), 3.05 (s, 3H), 2.69 (s, 3H), 2.32 (s, 3H), 2.28 (s, 3H)

Examples 265 AND 266

The titled compounds of Examples 265 and 266 were prepared, in accordance with the same procedures as in Step 2 of Example 33, using 7-(4-fluorobenzyloxy)-2,3,5,6-tetramethyl-1H-pyrrolo[3,2-b]pyridine prepared in Step 6 of Example 264; and, 1-iodopropane or 2-bromoethyl methyl ether.

Example 265

1-propyl-7-(4-fluorobenzyloxy)-2,3,5,6-tetramethyl-1H-pyrrolo[3,2-b]pyridine hydrochloride ¹H-NMR (CDCl₃) δ7.41 (m, 2H), 7.14 (m, 2H), 5.07 (s, 2H), 4.02 (t, 2H), 3.03 (s, 3H), 2.63 (s, 3H), 2.38 (s, 3H), 2.34 (s, 3H)(, 0.18 (m, 2H), 0.72 (t, 3H); (Yield: 66.4%)

Example 266

7-(4-fluorobenzyloxy)-1-(2-methoxyethyl)-2,3,5,6-tetramethyl-1H-pyrrolo[3,2-b]pyridine hydrochloride ¹H-NMR (CDCl₃) δ7.39 (m, 2H), 7.15 (m, 2H), 5.11 (s, 2H), 4.29 (s, 2H), 3.47 (s, 2H), 3.16 (s, 3H), 3.04 (s, 3H), 2.64 (s, 3H), 2.41 (s, 3H), 2.36 (s, 3H); (Yield: 77.4%)

Example 267

N-(1-allyl-2,3,5,6-tetramethyl-1H-pyrrolo[3,2-b]pyridin-7-yl)-4-fluorobenzylamine hydrochloride Step 1: (4-fluorobenzyl)-(2,3,5,6-tetramethyl-1H-pyrrolo[3,2-b]pyridin-7-yl)-carbamic acid tert-butyl ester In accordance with the same procedures as in Preparation 3, except for using 2,3-dimethyl-4-chloro-5-nitropyridine prepared in Step 4 of Example 264 and 4-fluorobenzylamine, the titled compound was obtained as a white solid. (Yield: 12.4%)

¹H-NMR (CDCl₃) δ8.31 (d, 1H), 8.12 (s, 1H), 7.40 (m, 1H), 7.18 (d, 2H), 7.09 (d, 2H), 3.16 (s, 3H), 2.53 (s, 3H), 2.48 (s, 3H), 1.41 (s, 9H)

Step 2: N-(I-allyl-2,3,5,6-tetramethyl-1H-pyrrolo[3,2-b]pyridin-7-yl)-4-fluorobenzylamine hydrochloride In accordance with the same procedures as in Example 244 and/or Step 2 of Example 254, except for using (4-fluorobenzyl)-(2,3,5,6-tetramethyl-1H-pyrrolo[3,2-b]pyridin-7-yl) carbamic acid tert-butyl ester prepared in Step 1 and allyl bromide, the titled compound was obtained as a white solid. (Yield: 58.5%)

¹H-NMR (CDCl₃) δ7.06 (t, 2H), 6.96 (t, 2H), 5.77 (m, 1H), 5.12 (m, 2H), 4.704 (m, 3H), 4.31 (m, 1H), 2.95 (s, 3H), 2.68 (s, 3H), 2.40 (s, 3H), 1.67 (s, 3H)

Examples 268 to 271

The titled compounds of Examples 268 to 271 were prepared, in accordance with the same procedures as in Example 244 and/or Step 2 of Example 254, using (4-fluorobenzyl)-(2,3,5,6-tetramethyl-1H-pyrrolo[3,2-b]pyridin-7-yl)-carbamic acid tert-butyl ester prepared in Step 1 of Example 267; and, benzyl bromide, (bromomethyl)cyclopropane, 1-iodopropane, or 2-bromoethyl methyl ether.

Example 268

N-(1-benzyl-2,3,5,6-tetramethyl-1H-pyrrolo[3,2-b]pyridin-7-yl)-4-fluorobenzylamine hydrochloride ¹H-NMR (CDCl₃) δ7.56 (m, 4H), 7.24 (m, 2H), 7.08 (t, 1H), 6.94 (t, 1H), 6.76 (d, 1H), 5.52 (d, 1H), 5.24 (d, 1H), 5.02 (d, 1H), 4.18 (d, 1H), 2.90 (s, 3H), 2.62 (s, 3H), 2.30 (s, 3H), 1.70 (s, 3H); (Yield: 75.6%)

Example 269

N-(1-cyclopropylmethyl-2,3,5,6-tetramethyl-1H-pyrrolo[3,2-b]pyridin-7-yl)-4-fluorobenzylamine hydrochloride ¹H-NMR (CDCl₃) δ7.01 (t, 2H), 6.94 (t, 2H), 5.22 (d, 1H), 4.19 (m, 2H), 3.86 (m, 2H), 2.88 (s, 3H), 2.69 (s, 3H), 2.49 (s, 3H), 1.65 (s, 3H), 0.97 (m, 1H), 0.53 (m, 1H), 0.44 (m, 1H), 0.25 (brs, 1H); (Yield: 45.9%)

Example 270

N-(1-propyl-2,3,5,6-tetramethyl-1H-pyrrolo[3,2-b]pyridin-7-yl)-4-fluorobenzylamine hydrochloride ¹H-NMR (CDCl₃) δ7.03 (t, 2H), 6.95 (t, 2H), 5.19 (d, 1H), 4.27 (d, 1H), 4.03 (m, 1H), 3.90 (m, 1H), 2.95 (s, 3H), 2.67 (s, 3H), 2.45 (s, 3H), 1.67 (s, 3H), 1.55 (m, 2H), 0.88 (t, 3H); (Yield: 74.1%)

Example 271

N-[1-(2-methoxyethyl)-2,3,5,6-tetramethyl-1H-pyrrolo[3,2-b]pyridin-7-yl]-4-fluorobenzylamine hydrochloride ¹H-NMR (CDCl₃) δ7.03 (d, 2H), 6.94 (t, 2H), 5.20 (d, 1H), 4.26 (d, 2H), 4.21 (d, 1H), 3.47 (d, 2H), 3.15 (s, 3H), 2.92 (s, 3H), 2.66 (s, 3H), 2.47 (s, 3H), 1.63 (s, 3H); (Yield: 65.3%)

Example 272

6-bromo-7-(4-fluorobenzyloxy)-2,3-dimethyl-1H-pyrrolo[3,2-b]pyridine

Step 1: 3-bromo-5-nitropyridin-4-ol 4-hydroxy-3-nitropyridine (40 g, 0.285 mol) was added to 200 ml of water and then bromine (18.44 ml, 0.36 mol) was slowly added thereto at room temperature. The reaction mixture was stirred under heating for 2 hours at 50° C. and then cooled to room temperature. The resulting precipitate was filtered, washed with water, and then dried to give the titled compound as a pale yellow solid (49.8 g, 87.8%). The product was used in the subsequent step without further purification.

Step 2: 3-bromo-4-chloro-5-nitropyridine 3-bromo-5-nitropyridin-4-ol (49.8 g, 0.227 mol) prepared in Step 1 was slowly added at 0° C. to 200 ml of phosphorus trichloride. N,N-diethylaniline (34.65 ml, 0.227 mol) was slowly added thereto at the same temperature. The reaction mixture was refluxed under stirring for 2 hours and then concentrated under reduced pressure. The resulting residue was added to ice water and then extracted with 300 ml of ether. The separated organic layer was dried on anhydrous magnesium sulfate and then concentrated under reduced pressure to give 32.4 g of the titled compound as a pale yellow solid. The product was used in the subsequent step without further purification.

Step 3:
3-bromo-4-(4-fluorobenzyloxy)-5-nitropyridine

In accordance with the same procedures as in Preparation 2, except for using 3-bromo-4-chloro-5-nitropyridine (1.0 g, 4.21 mmol) prepared in Step 2, the titled compound was obtained as a white solid. (Yield: 78.3%)
$^1$H-NMR (CDCl$_3$) δ8.75 (s, 1H), 8.26 (s, 1H), 7.43 (m, 2H), 7.04 (m, 2H), 5.04 (s, 2H), Step 4: 6-bromo-7-(4-fluorobenzyloxy)-2,3-dimethyl-1H-pyrrolo[3,2-b]pyridine In accordance with the same procedures as in Step 1 of Example 33, except for using 3-bromo-4-(4-fluorobenzyloxy)-5-nitropyridine (1.28 g, 3.91 mmol) prepared in Step 3, the titled compound was obtained as a white solid. (Yield: 18.3%)
H-NMR (CDCl$_3$) δ8.43 (s, 1H), 7.71 (s, 1H), 7.40 (m, 2H), 7.06 (m, 2H), 5.22 (s, 2H), 2.30 (s, 3H), 2.24 (s, 3H)

Examples 273 to 275

The titled compounds of Examples 273 to 275 were prepared, in accordance with the same procedures as in Step 2 of Example 33, using 6-bromo-7-(4-fluorobenzyloxy)-2,3-dimethyl-1H-pyrrolo[3,2-b]pyridine prepared in Step 4 of Example 272; and, benzyl bromide, 1-iodopropane, or 2-bromoethyl methyl ether.

Example 273

1-benzyl-6-bromo-7-(4-fluorobenzyloxy)-2,3-dimethyl-1H-pyrrolo[3,2-b]pyridine hydrochloride $^1$H-NMR (CDCl$_3$) δ8.66 (s, 1H), 7.31 (m, 3H), 7.12 (m, 2H), 7.01 (t, 2H), 6.65 (brs, 2H), 5.50 (s, 2H), 5.11 (s, 2H), 2.61 (s, 3H), 2.11 (s, 3H); (Yield: 45.3%)

Example 274

6-bromo-7-(4-fluorobenzyloxy)-1-propyl-2,3-dimethyl-1H-pyrrolo[3,2-b]pyridine hydrochloride $^1$H-NMR (CDCl$_3$) δ8.60 (s, 1H), 7.45 (m, 2H), 7.14 (t, 2H), 5.44 (s, 2H), 4.01 (t, 2H), 2.55 (s, 3H), 2.41 (s, 3H), 1.59 (m, 2H), 0.70 (t, 3H); (Yield: 65.3%)

Example 275

6-bromo-7-(4-fluorobenzyloxy)-1-(2-methoxyethyl)-2,3-dimethyl-1H-pyrrolo[3,2-b]pyridine hydrochloride $^1$H-NMR (CDCl$_3$) δ8.60 (s, 1H), 7.44 (m, 2H), 7.14 (t, 2H), 5.47 (s, 2H), 4.28 (t, 2H), 3.44 (t, 2H), 3.17 (s, 2H), 2.55 (s, 3H), 2.40 (s, 3H); (Yield: 45.8%)

Example 276

1-benzyl-7-(4-fluorobenzyloxy)-2,3-dimethyl-1H-pyrrolo[3,2-b]pyridine-6-carbonitrile 1-Benzyl-6-bromo-7-(4-fluorobenzyloxy)-2,3-dimethyl-1H-pyrrolo[3,2-b]pyridine hydrochloride prepared in Example 273 was neutralized with a saturated sodium carbonate solution to obtain 1-benzyl-6-bromo-7-(4-fluoro-benzyloxy)-2,3-dimethyl-1H-pyrrolo[3,2-b]pyridine (1.4 g, 3.18 mmol). A solution of 1-benzyl-6-bromo-7-(4-fluoro-benzyloxy)-2,3-dimethyl-1H-pyrrolo[3,2-b]pyridine (1.4 g, 3.18 mmol) and copper (I) cyanide (700 mg, 7.52 mmol) in anhydrous N,N-dimethylformamide (30 ml) was refluxed for 48 hours and then cooled to room temperature. Ethyl acetate was added to the reaction mixture, which was then filtered to discard insoluble solid. Water was added to the resulting solution, which was then extracted with ethyl acetate. The resulting organic layer was dried on anhydrous magnesium sulfate and then concentrated under reduced pressure. The resulting residue was purified with silica gel column chromatography (ethyl acetate/methanol=10/1, v/v) to give 278 mg of the titled compound as a white solid.
$^1$H-NMR (CDCl$_3$) δ8.54 (s, 1H), 7.28 (m, 3H), 7.11 (m, 2H), 7.05 (t, 2H), 6.45 (s, 2H), 5.43 (s, 2H), 5.21 (s, 2H), 2.53 (s, 3H), 2.12 (s, 3H)

Example 277

1-benzyl-7-(4-fluorobenzyloxy)-2,3-dimethyl-1H-pyrrolo[3,2-b]pyridine-6-carboxamide 1-Benzyl-7-(4-fluorobenzyloxy)-2,3-dimethyl-1H-pyrrolo[3,2-b]pyridine-6-carbonitrile (500 mg, 1.30 mmol) prepared in Example 276 was diluted with a mixture of ethanol (8 ml) and water (2 ml). Potassium hydroxide (650 mg, 13.0 mmol) was added to the reaction mixture, which was then refluxed for 2 hours. Water was added to the reaction mixture, which was then extracted with ethyl acetate. The separated organic layer was dried on anhydrous magnesium sulfate and then concentrated under reduced pressure. The resulting residue was purified with silica gel column chromatography (ethyl acetate/methanol=10/1, (v/v)) to give 350 mg of the titled compound as a white solid.
$^1$H-NMR (CDCl$_3$) δ8.32 (s, 1H), 7.33 (m, 3H), 7.21 (m, 2H), 7.12 (t, 2H), 6.35 (s, 2H), 5.43 (s, 2H), 5.21 (s, 2H), 4.01 (brs, 2H), 2.41 (s, 3H), 2.23 (s, 3H)

Example 278

7-(4-fluorophenyl)-1-(2-methoxyethyl)-2,3-dimethyl-1H-pyrrolo[3,2-b]pyridine hydrochloride Step 1: 4-(4-fluorophenyl)-3-nitropyridine 4-Chloro-3-nitropyridine (3 g, 18.9 mmol) prepared in Step 1 of Preparation 1, 4-fluorophenylboronic acid (2.9 g, 20.79 mmol), tetrakis(triphenylphosphine)palladium(0) (2.1 g, 1.89 mmol), and potassium carbonate (7.8 g, 56.7 mmol) were suspended in 120 ml of 1,4-dioxane. The resulting suspension was refluxed under stirring for 24 hours, filtered with Celite, and then concentrated under reduced pressure. The resulting residue was purified with silica gel column chromatography to give 1.76 g of the titled compound as a pale yellow solid.
$^1$H-NMR (CDCl$_3$) δ9.09 (s, 1H), 8.82 (d, 1H), 7.40 (d, 1H), 7.34 (m, 2H), 7.20 (m, 2H)

Step 2: 7-(4-fluorophenyl)-2,3-dimethyl-1H-pyrrolo[3,2-b]pyridine

In accordance with the same procedures as in Step 1 of Example 33, except for using 4-(4-fluorophenyl)-3-nitropyridine prepared in Step 1, the titled compound was obtained as a white solid. (Yield: 14.8%) The product was used in the subsequent step without further purification.

Step 3: 7-(4-fluorophenyl)-1-(2-methoxyethyl)-2,3-dimethyl-1H-pyrrolo[3,2-b]pyridine hydrochloride In accordance with the same procedures as in Step 2 of Example 33, except for using 7-(4-fluorophenyl)-2,3-dimethyl-1H-pyrrolo[3,2-b]pyridine prepared in Step 2 and 2-bromoethyl methyl ether, the titled compound was obtained as a white solid. (Yield: 82.3%)
$^1$H-NMR (CDCl$_3$) δ8.43 (t, 1H), 7.44 (m, 2H), 7.28 (m, 2H), 7.13 (d, 1H), 4.00 (t, 2H), 3.08 (t, 2H), 3.05 (s, 3H), 2.64 (s, 3H), 2.50 (s, 3H)

Examples 279 to 287

The titled compounds of Examples 279 to 287 were prepared, in accordance with the same procedures as in Step 2 of Example 33, using 7-(4-fluorophenyl)-2,3-dimethyl-1H-pyrrolo[3,2-b]pyridine prepared in Step 2 of Example 278; and, (bromomethyl)cyclopropane, 3-fluorobenzyl chloride, iodoethane, 1-iodopropane, 3-methoxybenzyl chloride, 4-methylbenzyl chloride, 4-fluorobenzyl chloride, allyl bromide, or 3-chlorobenzyl bromide.

Example 279

7-(4-fluorophenyl)-1-cyclopropylmethyl-2,3-dimethyl-1H-pyrrolo[3,2-b]pyridine hydrochloride $^1$H-NMR (CDCl$_3$) δ8.45 (t, 1H), 7.45 (m, 2H), 7.28 (m, 2H), 7.15 (d, 1H), 3.76 (d, 2H), 2.67 (s, 3H), 2.52 (s, 3H), 0.62 (m, 1H), 0.30 (m, 2H), 0.11 (m, 2H); (Yield: 66.0%)

Example 280

7-(4-fluorophenyl)-1-(3-fluorobenzyl)-2,3-dimethyl-1H-pyrrolo[3,2-b]pyridine hydrochloride $^1$H-NMR (CDCl$_3$) δ8.48 (t, 1H), 7.17 (m, 1H), 7.11 (m, 3H), 7.03 (t, 2H), 6.95 (t, 1H), 6.11 (t, 2H), 5.03 (s, 2H), 2.73 (s, 3H), 2.42 (s, 3H); (Yield: 78.0%)

Example 281

1-ethyl-7-(4-fluorophenyl)-2,3-dimethyl-1H-pyrrolo[3,2-b]pyridine hydrochloride $^1$H-NMR (CDCl$_3$) δ8.44 (t, 1H), 7.46 (m, 2H), 7.28 (m, 2H), 7.13 (d, 1H), 3.83 (q, 2H), 2.65 (s, 3H), 2.48 (s, 3H), 0.92 (t, 3H); (Yield: 65.5%)

Example 282

7-(4-fluorophenyl)-1-propyl-2,3-dimethyl-1H-pyrrolo[3,2-b]pyridine hydrochloride $^1$H-NMR (CDCl$_3$) δ8.44 (t, 1H), 7.45 (m, 2H), 7.29 (m, 2H), 7.13 (d, 1H), 3.75 (t, 2H), 2.65 (s, 3H), 2.50 (t, 3H), 2.47 (s, 3H), 0.85 (m, 2H); (Yield: 66.2%)

Example 283

7-(4-fluorophenyl)-1-(3-methoxybenzyl)-2,3-dimethyl-1H-pyrrolo[3,2-b]pyridine hydrochloride $^1$H-NMR (CDCl$_3$) δ8.46 (t, 1H), 7.09 (m, 4H), 7.01 (t, 2H), 6.76 (d, 1H), 5.91 (s, 2H), 4.99 (s, 2H), 3.69 (s, 3H), 2.71 (s, 3H), 2.41 (s, 3H); (Yield: 70.5%)

Example 284

7-(4-fluorophenyl)-1-(4-methylbenzyl)-2,3-dimethyl-1H-pyrrolo[3,2-b]pyridine hydrochloride $^1$H-NMR (CDCl$_3$) δ8.46 (t, 1H), 7.10 (m, 3H), 7.03 (m, 3H), 7.91 (d, 1H), 4.98 (s, 2H), 4.71 (s, 2H), 2.38 (s, 3H), 2.40 (s, 3H), 2.29 (s, 3H); (Yield: 63.9%)

Example 285

7-(4-fluorophenyl)-1-(4-fluorobenzyl)-2,3-dimethyl-1H-pyrrolo[3,2-b]pyridine hydrochloride $^1$H-NMR (CDCl$_3$) δ8.47 (t, 1H), 7.12 (m, 3H), 7.01 (t, 2H), 6.89 (t, 2H), 6.30 (m, 2H), 5.01 (s, 2H), 2.72 (s, 3H), 2.42 (s, 3H); (Yield: 72.5%)

Example 286

1-allyl-7-(4-fluorophenyl)-2,3-dimethyl-1H-pyrrolo[3,2-b]pyridine hydrochloride $^1$H-NMR (CDCl$_3$) δ8.47 (t, 1H), 7.38 (m, 2H), 7.22 (t, 2H), 7.13 (d, 1H), 5.54 (m, 1H), 5.09 (d, 1H), 4.36 (s, 2H), 4.32 (d, 1H), 2.67 (s, 3H), 2.44 (s, 3H); (Yield: 66.5%)

Example 287

1-(3-chlorobenzyl)-7-(4-fluorophenyl)-2,3-dimethyl-1H-pyrrolo[3,2-b]pyridine hydrochloride $^1$H-NMR (CDCl$_3$) δ8.48 (t, 1H), 7.20 (d, 1H), 7.09 (m, 6H), 6.35 (s, 1H), 6.17 (d, 1H), 5.02 (s, 2H), 2.73 (s, 3H), 2.43 (s, 3H); (Yield: 78.8%)

Example 288

1-benzyl-7-(4-fluorobenzyloxy)-2,3-dimethyl-1H-pyrrolo[3,2-b]pyridine-6-carboxylic acid 1-Benzyl-7-(4-fluorobenzyloxy)-2,3-dimethyl-1H-pyrrolo[3,2-b]pyridine-6-carbonitrile (500 mg, 1.30 mmol) prepared in Example 276 was diluted with a mixture of ethanol (8 ml) and water (2 ml). Potassium hydroxide (650 mg, 13.0 mmol) was added to the solution, which was then refluxed for 24 hours. Water was added to the reaction mixture, which was then extracted with ethyl acetate. The separated organic layer was dried on anhydrous magnesium sulfate and then concentrated under reduced pressure. The resulting residue was purified with silica gel column chromatography (ethyl acetate/methanol=5/1, (v/v)) to give 280 mg of the titled compound as a white solid.
$^1$H-NMR (DMSO-d$_6$) δ10.7 (brs, 1H), 8.33 (s, 1H), 7.35 (m, 3H), 7.25 (m, 2H), 7.11 (t, 2H), 6.45 (s, 2H), 5.33 (s, 2H), 5.11 (s, 2H), 2.42 (s, 3H), 2.28 (s, 3H)

Example 289

1-benzyl-7-(4-fluorobenzyloxy)-2,3-dimethyl-N-cyclopropyl-1H-pyrrolo[3,2-b]pyridine-6-carboxamide 1-Benzyl-7-(4-fluorobenzyloxy)-2,3-dimethyl-1H-pyrrolo[3,2-b]pyridine-6-carboxylic acid (24.16 mg, 0.056 mmol) prepared in Example 288, 1-hydroxybenzotriazole hydrate (11.4 mg, 0.085 mmol), 1-(3-dimethylaminopropyl)-3-ethylcarbodiimide hydrochloride (16.3 mg, 0.085 mmol), diisopropylethyl amine (0.029 ml, 0.168 mmol), and cyclopropyl amine (5.8 ul, 0.084 mmol) were dissolved in dichloromethane (1 ml). The resulting solution was stirred for 2 hours at room temperature and then concentrated under reduced pressure. The resulting residue was purified with silica gel column chromatography (ethyl acetate/methanol=10/1, (v/v)) to give the titled compound as a white solid (12.3 mg, 58%).

$^1$H-NMR (DMSO-d$_6$) δ8.34 (s, 1H), 7.36 (m, 3H), 7.28 (m, 2H), 7.15 (t, 2H), 6.55 (s, 2H), 5.38 (s, 2H), 5.11 (s, 2H), 4.24 (d, 2H), 2.42 (s, 3H), 2.28 (s, 3H), 1.38 (m, 1H), 0.78 (m, 2H), 0.14 (m, 2H)

Test Example 1

Inhibitory Effects on Proton Pump (H$^+$/K$^+$-ATPase) Activity 1-1. Preparation of Gastric Proton Pump Vesicles The hog fundic regions containing parietal and peptic cells were scraped with slide-glass. The collected cells were suspended in 10 ml of 0.25M sucrose buffer and homogenized using a tight-fitting Teflon-glass homogenizer. The homogenate was centrifuged for 35 min at 8,000 rpm and the pellet was discarded. The supernatant was further centrifuged for 75 min at 25,000 rpm. The resulting pellets were re-suspended in the sucrose buffer (10 ml), and then the suspension was laid onto discontinuous density gradients consisting of 0.25M sucrose buffer and isolation medium containing 9% Ficoll (w/w). After being centrifuged for 3 hours and 15 minutes at 100,000×g, the material at the interface of sucrose buffer and Ficoll solution was collected and then centrifuged for 40 minutes at 100,000×g. The resulting pellets were re-suspended in 1 ml of 5 mM Hepes/Tris buffer (pH 6.1). This material was lyophilized and stored at −70° C. and used as an enzyme source of the in vitro enzyme reaction assay of proton pump.

1-2. Measurement of Inhibitory Effects on Proton Pump (H+/K+-ATPase) activity

The inhibitory effects of the compounds of the present invention against proton pump activity were evaluated in 96-well plate. In this assay, the K$^+$ specific H$^+$/K$^+$-ATPase activity was calculated based on the difference between the activity of H$^+$/K$^+$-ATPase activity with K$^+$ and without K$^+$ ion. In 96-well plate, 1% dimethylsulfoxide (DMSO) in buffer was added to negative and positive control groups and the diluted compounds of the present invention in buffer were added to test group. All assays were performed in 100 μl reaction volume at room temperature, and the hog gastric vesicle was kept in ice before use. At the beginning of the reaction, 10 μl of reaction buffer containing 1% DMSO was added to the negative and positive control groups and to each concentration of compounds in the test group. Then lyophilized vesicle in 5 mM Pipes/Tris buffer (pH 6.1) was pre-incubated in the presence of various concentrations of test compounds. After a 5 minute incubation, negative and positive buffers were respectively added to the previous reaction mixture. As the substrate, ATP was added to the reaction buffer, and incubated for 30 minutes at 37° C. Enzymatic activity was stopped by the addition of colorimetric reagent (2× malachite green, 1× ammonium molybdate, 1× polyvinyl alcohol, 2× H$_2$O) and the amount of mono phosphate (Pi) in the reaction was measured at 620 nm using the micro plate reader (Genios Pro, TECAN). The difference between the Pi production with K$^+$ and without K$^+$ is taken as K$^+$ stimulated H$^+$/K$^+$-ATPase activity. The IC$_{50}$S of test compounds were calculated from each % inhibition value of compounds using the method of Litchfield-Wilcoxon (*J. Pharmacol. Exp. Ther.* (1949) 96, 99). The results are shown in Table 1.

TABLE 1

| Example | IC$_{50}$ (uM) | Example | IC$_{50}$ (uM) |
|---|---|---|---|
| 1 | 0.65 | 2 | 1.06 |
| 3 | 0.64 | 5 | 0.32 |
| 6 | 0.20 | 7 | 0.22 |
| 8 | 0.44 | 9 | 0.33 |
| 10 | 0.69 | 12 | 0.97 |
| 13 | 0.80 | 14 | 0.53 |
| 15 | 3.81 | 16 | 0.19 |
| 23 | 2.29 | 33 | 0.65 |
| 34 | 0.23 | 35 | 1.09 |
| 37 | 1.26 | 38 | 1.31 |
| 39 | 0.22 | 40 | 0.19 |
| 50 | 2.44 | 54 | 2.30 |
| 55 | 0.07 | 56 | 0.57 |
| 57 | 0.27 | 58 | 0.23 |
| 61 | 0.10 | 62 | 0.11 |
| 64 | 0.05 | 65 | 0.06 |
| 66 | 0.05 | 67 | 0.05 |
| 68 | 0.06 | 69 | 0.06 |
| 70 | 0.04 | 71 | 0.06 |
| 72 | 0.03 | 73 | 0.04 |
| 74 | 1.08 | 79 | 1.59 |
| 80 | 2.87 | 81 | 1.25 |
| 82 | 4.70 | 83 | 3.82 |
| 84 | 0.39 | 85 | 0.17 |
| 86 | 0.05 | 87 | 0.16 |
| 88 | 0.67 | 89 | 0.34 |
| 90 | 0.14 | 91 | 0.46 |
| 92 | 0.05 | 93 | 0.05 |
| 94 | 0.89 | 95 | 0.52 |
| 96 | 0.13 | 97 | 0.09 |
| 98 | 0.62 | 99 | 0.63 |
| 100 | 2.82 | 101 | 1.01 |
| 113 | 1.42 | 114 | 0.07 |
| 115 | 0.13 | 116 | 0.15 |
| 117 | 0.72 | 118 | 0.46 |
| 119 | 0.23 | 120 | 0.12 |
| 121 | 0.32 | 122 | 0.02 |
| 123 | 0.06 | 124 | 0.05 |
| 125 | 0.05 | 126 | 0.05 |
| 127 | 0.04 | 128 | 0.05 |
| 129 | 0.04 | 130 | 0.04 |
| 131 | 0.06 | 132 | 0.05 |
| 133 | 0.06 | 134 | 0.54 |
| 135 | 0.15 | 136 | 0.05 |
| 137 | 0.06 | 138 | 0.46 |
| 139 | 0.02 | 140 | 0.08 |
| 141 | 0.09 | 144 | 0.24 |
| 145 | 0.53 | 146 | 3.15 |
| 147 | 3.45 | 153 | 1.03 |
| 154 | 0.24 | 155 | 0.57 |
| 156 | 0.61 | 157 | 0.57 |
| 158 | 0.32 | 159 | 0.88 |
| 161 | 0.58 | 162 | 1.15 |
| 163 | 1.01 | 164 | 3.00 |
| 177 | 0.29 | 178 | 0.84 |
| 179 | 0.57 | 180 | 0.83 |
| 181 | 4.71 | 182 | 3.88 |
| 183 | 1.21 | 184 | 1.07 |
| 195 | 0.68 | 196 | 0.38 |
| 200 | 0.60 | 201 | 0.68 |

TABLE 1-continued

| Example | IC$_{50}$ (uM) | Example | IC$_{50}$ (uM) |
|---|---|---|---|
| 218 | 3.28 | 219 | 0.06 |
| 220 | 0.05 | 221 | 0.18 |
| 222 | 0.06 | 223 | 1.21 |
| 224 | 0.12 | 225 | 0.62 |
| 226 | 0.45 | 227 | 0.09 |
| 228 | 0.03 | 229 | 0.07 |
| 254 | 0.21 | 255 | 0.55 |
| 256 | 2.08 | 260 | 1.21 |
| 261 | 2.06 | 263 | 1.45 |
| 264 | 3.07 | 268 | 1.25 |

As shown in Table 1, the compounds of the present invention have excellent inhibitory effects on gastric $H^+/K^+$-ATPase.

Test Example 2

Inhibitory Effects on Basal Gastric Acid Secretion in Pylorus-Ligated Rats

Inhibitory effects of the compounds of the present invention on basal gastric acid secretion were performed according to Shay's rat model (Shay, H., et al., 1945, gastroenterology, 5, 43-61). Male Sprague Dawley (SD) rats (200±10 g body weight) were divided into 3 groups (n=5) and fasted for 24 hours with free access to water. Control group was orally administered with 0.5% methylcellulose alone and the other groups were orally administered with test compounds suspended in 0.5% methyl-cellulose solution at doses of 1, 3 and 10 mg/kg/5 ml one hour before pylorus ligation.

Under ether anesthesia, the abdomens of the rats were incised and then the pylorus was ligated. 5 hours after ligation, the animals were sacrificed, and the gastric contents were collected. The collected contents were centrifuged at 1,000×g for 10 minutes to obtain the gastric juice. Total acid output was measured by 0.01N NaOH volume (ueq/ml) for automatic titration of the gastric juice to pH 7.0 and the ED$_{50}$s of test compounds were calculated using the Litchfield-Wilcoxon method. % inhibitory activity was calculated from the following equation and the results are shown in Table 2.

% inhibitory activity of test compound=(total acid output of control group−total acid output of the group treated with test compounds)/total acid output of control group X 100

TABLE 2

| Example | ED$_{50}$ (mg/kg) |
|---|---|
| 50 | 2.4 |
| 54 | 2.3 |
| 55 | 1.3 |
| 61 | 3.0 |
| 62 | 1.6 |
| 72 | 2.0 |
| 73 | 2.5 |
| 86 | 1.1 |
| 97 | 2.0 |
| 139 | 1.6 |

As shown in Table 2, the compounds of the present invention have potent inhibition activities against basal gastric acid secretion in pylorus-ligated rats.

Test Example 3

Reversible Inhibition of Hog Gastric $H^+/K^+$-ATPase 3-1. Preparation of Gastric Vesicles Gastric vesicles were prepared from hog fundic mucosa using the method of Saccomani et al. (Saccomani G, Stewart H B, Shqw D, Lewin M and Sachs G, Characterization of gastric mucosal membranes. IX. Fraction and purification of K-ATPase-containing vesicles by zonal centrifugation and free-flow electrophoresis technique. *Biochem. Biophy. Acta.* (BBA)—Biomembranes 465, 311-330, 1977.). This material was lyophilized and stored at −70° C. The protein content of gastric vesicles was determined by the Bradford method using bovine serum albumin as a standard (Bradford M M, A rapid and sensitive method for the quantitation of microgram quantities of protein utilizing the principle of protein-dye binding. *Anal Biochem.* 72, 248-254, 1976).

3-2. Determination of reversible inhibition of hog gastric $H^+/K^+$-ATPase

Activity of $H^+/K^+$-ATPase in hog microsome (lyophilized vesicle) was measured by the inorganic phosphate released from ATP using an one-step colorimetric detection method at the concentration at which the test compounds have 50% inhibition of the proton pump (Chan K M, Delfert D, and Junger K D, A direct colorimetric assay for $Ca^{2+}$-stimulated ATPase activity. *Anal Biochem,* 157, 375-380, 1986). The mode of action of test compounds on $H^+/K^+$-ATPase was investigated according to the Washout method (Beil W, Staar U, and Sewing K F, Substituted thieno[3,4-d]imidazoles, a novel group of $H^+/K^+$-ATPase inhibitors. Differentiation of their inhibition characteristics from those of omeprazole. *Eur. J. Pharmacol.,* 187, 455-67, 1990).

Lyophilized vesicle in the solution of 5 mM Pipes/Tris buffer was pre-incubated in the presence of the test compounds (the compounds of Examples 50, 64, and 94) at the concentration at which it has 50% inhibition of the proton pump. The previous reaction buffer was added with 2 mM $MgCl_2$, 50 mM KCl, 5 uM Valinomycin, and 0.5 mM ATP and then incubated for 30 minutes at 37° C. The $H^+/K^+$-ATPase activity was measured using the calorimetric detection method and then the test sample was centrifuged at 100,000×g for 1 hr. The vesicles are present in the form of pellets in the test sample. The supernatant thereof was replaced with the same buffer not having the test compound. The test sample was pre-incubated for 5 minutes at room temperature and then incubated further for 30 minutes at 37° C. The $H^+/K^+$-ATPase activity was also measured using the calorimetric detection method. The $H^+/K^+$-ATPase activity before washout and after washout in the test sample was analyzed, in comparison with those in the non-treated group.

As a result, the compounds of Examples 50, 64, and 94 inhibited $H^+/K^+$-ATPase activity by 50% before washout and did not inhibit $H^+/K^+$-ATPase activity after washout; the gastric $H^+/K^+$-ATPase activities by the compounds of Examples 50, 64, and 94 were completely recovered to non-treated group level after washout. These results confirm that the compounds of formula (I) exhibited reversible inhibition of the gastric $H^+/K^+$-ATPase.

The invention claimed is:

1. A compound of the formula (I) or a pharmaceutically acceptable salt thereof:

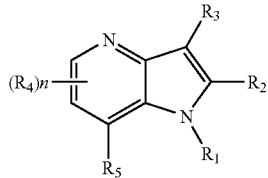

wherein:
$R_1$ is hydrogen; a straight or branched $C_1$-$C_6$ alkyl group, optionally substituted with one or more substituents selected from the group consisting of $C_1$-$C_5$ alkoxy, hydroxy, $C_3$-$C_7$ cycloalkyl, acetoxy, $C_2$-$C_6$ alkenyloxy, $C_1$-$C_3$ alkoxycarbonyl, amino optionally one or two substituted with $C_1$-$C_3$ alkyl, cyano, naphthyl, pyridyl, oxiranyl, oxazolidinonyl, isoxazolyl optionally one or more substituted with $C_1$-$C_3$ alkyl, 1,3-dioxolanyl, and 2,3-dihydrobenzo[1,4]dioxinyl; a straight or branched $C_2$-$C_6$ alkenyl group; a straight or branched $C_2$-$C_6$ alkynyl group; or a benzyl group, optionally substituted with one or more substituents selected from the group consisting of halogen, $C_1$-$C_3$ alkyl, $C_1$-$C_3$ alkoxy, cyano, $C_1$-$C_3$ alkoxycarbonyl, and trifluoro-$C_1$-$C_3$ alkyl, $R_2$ is a straight or branched $C_1$-$C_6$ alkyl group, $R_3$ is a straight or branched $C_1$-$C_6$ alkyl group optionally substituted with hydroxy, $R_4$ is hydrogen; a straight or branched $C_1$-$C_6$ alkyl group; halogen; cyano; hydroxycarbonyl; aminocarbonyl; or $C_3$-$C_7$ cycloalkyl-aminocarbonyl, $R_5$ is a 1,2,3,4-tetrahydroisoquinolinyl group optionally one or more substituted with halogen or $C_1$-$C_5$ alkyl; a benzyloxy group optionally substituted with one or more substituents selected from the group consisting of halogen, $C_1$-$C_5$ alkyl, $C_1$-$C_5$ alkoxy, and trifluoro-$C_1$-$C_3$ alkyl; an amino group optionally substituted with one or two substituents selected from the group consisting of $C_1$-$C_5$ alkoxy-carbonyl and benzyl optionally substituted with halogen; a phenyl group optionally one or more substituted with halogen; a phenoxy group optionally one or more substituted with halogen; a pyridyl-$C_1$-$C_3$ alkoxy group; or a piperonyloxy group, and n is 1 or 2.

2. The compound or a pharmaceutically acceptable salt thereof according to claim 1, wherein $R_1$ is hydrogen; a straight or branched $C_1$-$C_6$ alkyl group; a $C_1$-$C_3$ alkyl group substituted with one or more substituents selected from the group consisting of methoxy, hydroxy, cyclopropyl, cyclobutyl, acetoxy, vinyloxy, methoxycarbonyl, dimethylamino, cyano, naphthyl, pyridyl, oxiranyl, oxazolidinonyl, dimethylisoxazolyl, 1,3-dioxolanyl, and 2,3-dihydrobenzo[1,4]dioxinyl; a straight or branched $C_2$-$C_6$ alkenyl group; a straight or branched $C_2$-$C_6$ alkynyl group; or a benzyl group, optionally substituted with one or more substituents selected from the group consisting of halogen, $C_1$-$C_3$ alkyl, $C_1$-$C_3$ alkoxy, cyano, methoxycarbonyl, and trifluoromethyl, $R_2$ is a methyl group, $R_3$ is a methyl group or a hydroxymethyl group, $R_4$ is hydrogen; a methyl group; halogen; cyano; hydroxycarbonyl; aminocarbonyl; or cyclopropylaminocarbonyl;

$R_5$ is 1,2,3,4-tetrahydroisoquinolinyl; 6-fluoro-1-methyl-1,2,3,4-tetrahydroisoquinolinyl; a benzyloxy group substituted with one or more substituents selected from the group consisting of halogen, $C_1$-$C_3$ alkyl, $C_1$-$C_5$ alkoxy, and trifluoromethyl; an amino group one or two substituted with tert-butoxycarbonyl or fluorobenzyl; a fluorophenyl group; a fluorophenoxy group; pyridyl-methoxy; or piperonyloxy, and n is 1 or 2.

3. The compound or a pharmaceutically acceptable salt thereof according to claim 1, which is selected from the group consisting of:

1-(4-chlorobenzyl)-7-(1,2,3,4-tetrahydroisoquinolin-2-yl)-2,3-dimethyl-1H-pyrrolo[3,2-b]pyridine hydrochloride;

1-(2-naphthylmethyl)-7-(1,2,3,4-tetrahydroisoquinolin-2-yl)-2,3-dimethyl-1H-pyrrolo[3,2-b]pyridine hydrochloride;

1-(1,3-dioxolan-2-ylmethyl)-7-(1,2,3,4-tetrahydroisoquinolin-2-yl)-2,3-dimethyl-1H-pyrrolo[3,2-b]pyridine hydrochloride;

1-cyclopropylmethyl-7-(1,2,3,4-tetrahydroisoquinolin-2-yl)-2,3-dimethyl-1H-pyrrolo[3,2-b]pyridine hydrochloride;

1-(2-methoxyethyl)-7-(1,2,3,4-tetrahydroisoquinolin-2-yl)-2,3-dimethyl-1H-pyrrolo[3,2-b]pyridine hydrochloride;

1-benzyl-7-(1,2,3,4-tetrahydroisoquinolin-2-yl)-2,3-dimethyl-1H-pyrrolo[3,2-b]pyridine hydrochloride;

1-allyl-7-(1,2,3,4-tetrahydroisoquinolin-2-yl)-2,3-dimethyl-1H-pyrrolo[3,2-b]pyridine hydrochloride;

1-(3-methoxybenzyl)-7-(1,2,3,4-tetrahydroisoquinolin-2-yl)-2,3-dimethyl-1H-pyrrolo[3,2-b]pyridine hydrochloride;

1-(2-fluorobenzyl)-7-(1,2,3,4-tetrahydroisoquinolin-2-yl)-2,3-dimethyl-1H-pyrrolo[3,2-b]pyridine hydrochloride;

1-(4-methoxybenzyl)-7-(1,2,3,4-tetrahydroisoquinolin-2-yl)-2,3-dimethyl-1H-pyrrolo[3,2-b]pyridine hydrochloride;

1-propyl-7-(1,2,3,4-tetrahydroisoquinolin-2-yl)-2,3-dimethyl-1H-pyrrolo[3,2-b]pyridine hydrochloride;

1-(3-methylbenzyl)-7-(1,2,3,4-tetrahydroisoquinolin-2-yl)-2,3-dimethyl-1H-pyrrolo[3,2-b]pyridine hydrochloride;

1-ethyl-7-(1,2,3,4-tetrahydroisoquinolin-2-yl)-2,3-dimethyl-1H-pyrrolo[3,2-b]pyridine hydrochloride;

1-[2-(1,3-dioxolan-2-yl)ethyl]-7-(1,2,3,4-tetrahydroisoquinolin-2-yl)-2,3-dimethyl-1H-pyrrolo[3,2-b]pyridine hydrochloride;

1-(2,3-dihydrobenzo[1,4]dioxin-6-ylmethyl)-7-(1,2,3,4-tetrahydroisoquinolin-2-yl)-2,3-dimethyl-1H-pyrrolo[3,2-b]pyridine hydrochloride;

1-(3-methylbuten-2-yl)-7-(1,2,3,4-tetrahydroisoquinolin-2-yl)-2,3-dimethyl-1H-pyrrolo[3,2-b]pyridine hydrochloride;

1-(3,5-dimethylisoxazol-4-ylmethyl)-7-(1,2,3,4-tetrahydroisoquinolin-2-yl)-2,3-dimethyl-1H-pyrrolo[3,2-b]pyridine hydrochloride;

1-(2-chlorobenzyl)-7-(1,2,3,4-tetrahydroisoquinolin-2-yl)-2,3-dimethyl-1H-pyrrolo[3,2-b]pyridine hydrochloride;

1-methoxycarbonylethyl-7-(1,2,3,4-tetrahydroisoquinolin-2-yl)-2,3-dimethyl-1H-pyrrolo[3,2-b]pyridine hydrochloride;

1-methoxymethyl-7-(1,2,3,4-tetrahydroisoquinolin-2-yl)-2,3-dimethyl-1H-pyrrolo[3,2-b]pyridine hydrochloride;

1-(4-tert-butylbenzyl)-7-(1,2,3,4-tetrahydroisoquinolin-2-yl)-2,3-dimethyl-1H-pyrrolo[3,2-b]pyridine hydrochloride;

1-cyclobutylmethyl-7-(1,2,3,4-tetrahydroisoquinolin-2-yl)-2,3-dimethyl-1H-pyrrolo[3,2-b]pyridine hydrochloride;

1-(3-cyanobenzyl)-7-(1,2,3,4-tetrahydroisoquinolin-2-yl)-2,3-dimethyl-1H-pyrrolo[3,2-b]pyridine hydrochloride;

1-methoxycarbonylmethyl-7-(1,2,3,4-tetrahydroisoquinolin-2-yl)-2,3-dimethyl-1H-pyrrolo[3,2-b]pyridine hydrochloride;

1-(2,4-dimethylbenzyl)-7-(1,2,3,4-tetrahydroisoquinolin-2-yl)-2,3-dimethyl-1H-pyrrolo[3,2-b]pyridine hydrochloride;

1-(4-methoxycarbonylbenzyl)-7-(1,2,3,4-tetrahydroisoquinolin-2-yl)-2,3-dimethyl-1H-pyrrolo[3,2-b]pyridine hydrochloride;

1-(2-vinyloxyethyl)-7-(1,2,3,4-tetrahydroisoquinolin-2-yl)-2,3-dimethyl-1H-pyrrolo[3,2-b]pyridine hydrochloride;

1-isobutyl-7-(1,2,3,4-tetrahydroisoquinolin-2-yl)-2,3-dimethyl-1H-pyrrolo[3,2-b]pyridine hydrochloride;

1-oxiranylmethyl-7-(1,2,3,4-tetrahydroisoquinolin-2-yl)-2,3-dimethyl-1H-pyrrolo[3,2-b]pyridine hydrochloride;

1-benzyl-7-(1,2,3,4-tetrahydroisoquinolin-2-yl)-3-hydroxymethyl-2-methyl-1H-pyrrolo[3,2-b]pyridine hydrochloride;

2-(2,3-dimethyl-1H-pyrrolo[3,2-b]pyridin-7-yl)-6-fluoro-1-methyl-1,2,3,4-tetrahydroisoquinoline;

2-(1-benzyl-2,3-dimethyl-1H-pyrrolo[3,2-b]pyridin-7-yl)-6-fluoro-1-methyl-1,2,3,4-tetrahydroisoquinoline hydrochloride;

1-(4-chlorobenzyl)-7-(4-fluorobenzyloxy)-2,3-dimethyl-1H-pyrrolo[3,2-b]pyridine hydrochloride;

7-(4-fluorobenzyloxy)-2,3-dimethyl-1-(4-methylbenzyl)-1H-pyrrolo[3,2-b]pyridine hydrochloride;

4-[7-(4-fluorobenzyloxy)-2,3-dimethyl-pyrrolo[3,2-b]pyridin-1-ylmethyl]-benzoic acid methyl ester hydrochloride;

1-(4-tert-butylbenzyl)-7-(4-fluorobenzyloxy)-2,3-dimethyl-1H-pyrrolo[3,2-b]pyridine hydrochloride;

7-(4-fluorobenzyloxy)-2,3-dimethyl-1-(naphthalen-2-ylmethyl)-1H-pyrrolo[3,2-b]pyridine hydrochloride;

7-(4-fluorobenzyloxy)-2,3-dimethyl-1-(2-vinyloxyethyl)-1H-pyrrolo[3,2-b]pyridine hydrochloride;

1-(1,3-dioxolan-2-ylmethyl)-7-(4-fluorobenzyloxy)-2,3-dimethyl-1H-pyrrolo[3,2-b]pyridine hydrochloride;

1-(3-fluorobenzyl)-7-(4-fluorobenzyloxy)-2,3-dimethyl-1H-pyrrolo[3,2-b]pyridine hydrochloride;

1-(2,5-dimethylbenzyl)-7-(4-fluorobenzyloxy)-2,3-dimethyl-1H-pyrrolo[3,2-b]pyridine hydrochloride;

1-(3,5-dimethylisoxazol-4-ylmethyl)-7-(4-fluorobenzyloxy)-2,3-dimethyl-1H-pyrrolo[3,2-b]pyridine hydrochloride;

1-(3-chlorobenzyl)-7-(4-fluorobenzyloxy)-2,3-dimethyl-1H-pyrrolo[3,2-b]pyridine hydrochloride;

1-(pyridin-2-ylmethyl)-7-(4-fluorobenzyloxy)-2,3-dimethyl-1H-pyrrolo[3,2-b]pyridine hydrochloride;

1-(2,3-dihydrobenzo[1,4]dioxin-6-ylmethyl)-7-(4-fluorobenzyloxy)-2,3-dimethyl-1H-pyrrolo[3,2-b]pyridine hydrochloride;

1-(3-cyanobenzyl)-7-(4-fluorobenzyloxy)-2,3-dimethyl-1H-pyrrolo[3,2-b]pyridine hydrochloride;

1-oxiranylmethyl-7-(4-fluorobenzyloxy)-2,3-dimethyl-1H-pyrrolo[3,2-b]pyridine hydrochloride;

1-(pyridin-3-ylmethyl)-7-(4-fluorobenzyloxy)-2,3-dimethyl-1H-pyrrolo[3,2-b]pyridine hydrochloride;

1-allyl-7-(4-fluorobenzyloxy)-2,3-dimethyl-1H-pyrrolo[3,2-b]pyridine hydrochloride;

7-(4-fluorobenzyloxy)-1-isobutyl-2,3-dimethyl-1H-pyrrolo[3,2-b]pyridine hydrochloride;

7-(4-fluorobenzyloxy)-2,3-dimethyl-1-(prop-2-ynyl)-1H-pyrrolo[3,2-b]pyridine hydrochloride;

7-(4-fluorobenzyloxy)-1-(3-methoxybenzyl)-2,3-dimethyl-1H-pyrrolo[3,2-b]pyridine hydrochloride;

7-(4-fluorobenzyloxy)-1-(3-methylbenzyl)-2,3-dimethyl-1H-pyrrolo[3,2-b]pyridine hydrochloride;

1-benzyl-7-(4-fluorobenzyloxy)-2,3-dimethyl-1H-pyrrolo[3,2-b]pyridine hydrochloride;

1-cyclobutylmethyl-7-(4-fluorobenzyloxy)-2,3-dimethyl-1H-pyrrolo[3,2-b]pyridine hydrochloride;

7-(4-fluorobenzyloxy)-2,3-dimethyl-1-(3-methyl-2-buten-2-yl)-1H-pyrrolo[3,2-b]pyridine hydrochloride;

1-[2-(methoxycarbonyl)ethyl]-7-(4-fluorobenzyloxy)-2,3-dimethyl-1H-pyrrolo[3,2-b]pyridine hydrochloride;

7-(4-fluorobenzyloxy)-1-(4-methoxybenzyl)-2,3-dimethyl-1H-pyrrolo[3,2-b]pyridine hydrochloride;

1-(2-fluorobenzyl)-7-(4-fluorobenzyloxy)-2,3-dimethyl-1H-pyrrolo[3,2-b]pyridine hydrochloride;

1-cyclopropylmethyl-7-(4-fluorobenzyloxy)-2,3-dimethyl-1H-pyrrolo[3,2-b]pyridine hydrochloride;

7-(4-fluorobenzyloxy)-1-(2-methoxyethyl)-2,3-dimethyl-1H-pyrrolo[3,2-b]pyridine hydrochloride;

7-(4-fluorobenzyloxy)-2,3-dimethyl-1-propyl-1H-pyrrolo[3,2-b]pyridine hydrochloride;

1-benzyl-7-(4-fluorobenzyloxy)-2,3-dimethyl-1H-pyrrolo[3,2-b]pyridine methanesulfonate;

1-benzyl-7-(4-fluorobenzyloxy)-2,3-dimethyl-1H-pyrrolo[3,2-b]pyridine benzenesulfonate;

1-benzyl-7-(4-fluorobenzyloxy)-2,3-dimethyl-1H-pyrrolo[3,2-b]pyridine p-toluenesulfonate;

1-benzyl-7-(4-fluorobenzyloxy)-2,3-dimethyl-1H-pyrrolo[3,2-b]pyridine nitrate;

1-benzyl-7-(4-fluorobenzyloxy)-2,3-dimethyl-1H-pyrrolo[3,2-b]pyridine sulfate;

1-benzyl-7-(4-fluorobenzyloxy)-2,3-dimethyl-1H-pyrrolo[3,2-b]pyridine maleate;

1-benzyl-7-(4-fluorobenzyloxy)-2,3-dimethyl-1H-pyrrolo[3,2-b]pyridine phosphate;

1-benzyl-7-(4-fluorobenzyloxy)-2,3-dimethyl-1H-pyrrolo[3,2-b]pyridine malonate;

1-benzyl-7-(4-fluorobenzyloxy)-2,3-dimethyl-1H-pyrrolo[3,2-b]pyridine hydrobromide;

1-allyl-7-(4-chlorobenzyloxy)-2,3-dimethyl-1H-pyrrolo[3,2-b]pyridine hydrochloride;

1-benzyl-7-(4-chlorobenzyloxy)-2,3-dimethyl-1H-pyrrolo[3,2-b]pyridine hydrochloride;

7-(4-chlorobenzyloxy)-1-methoxymethyl-2,3-dimethyl-1H-pyrrolo[3,2-b]pyridine hydrochloride;

1-(2-cyanobenzyl)-7-(4-chlorobenzyloxy)-2,3-dimethyl-1H-pyrrolo[3,2-b]pyridine hydrochloride;

1-(2-chlorobenzyl)-7-(4-chlorobenzyloxy)-2,3-dimethyl-1H-pyrrolo[3,2-b]pyridine hydrochloride;

1-cyanomethyl-7-(4-chlorobenzyloxy)-2,3-dimethyl-1H-pyrrolo[3,2-b]pyridine hydrochloride;

7-(4-chlorobenzyloxy)-2,3-dimethyl-1-(4-trifluoromethylbenzyl)-1H-pyrrolo[3,2-b]pyridine hydrochloride;

1-(4-tert-butylbenzyl)-7-(4-chlorobenzyloxy)-2,3-dimethyl-1H-pyrrolo[3,2-b]pyridine hydrochloride;

7-(4-chlorobenzyloxy)-2,3-dimethyl-1-(pyridin-4-ylmethyl)-1H-pyrrolo[3,2-b]pyridine hydrochloride;

5-[7-(4-chlorobenzyloxy)-2,3-dimethyl-pyrrolo[3,2-b]pyridin-1-ylmethyl]-oxazolidin-2-one hydrochloride;

7-(4-chlorobenzyloxy)-1-(2,5-dimethylbenzyl)-2,3-dimethyl-1H-pyrrolo[3,2-b]pyridine hydrochloride;

[7-(4-chlorobenzyloxy)-2,3-dimethyl-pyrrolo[3,2-b]pyridin-1-yl]-acetic acid methyl ester hydrochloride;

7-(4-chlorobenzyloxy)-2,3-dimethyl-1-(3-methylbut-2-enyl)-1H-pyrrolo[3,2-b]pyridine hydrochloride;

1-(2-acetoxyethyl)-7-(4-chlorobenzyloxy)-2,3-dimethyl-1H-pyrrolo[3,2-b]pyridine hydrochloride;

7-(4-chlorobenzyloxy)-1-(2-methoxyethyl)-2,3-dimethyl-1H-pyrrolo[3,2-b]pyridine hydrochloride;

7-(4-chlorobenzyloxy)-1-(1,3-dioxolan-2-ylmethyl)-2,3-dimethyl-1H-pyrrolo[3,2-b]pyridine hydrochloride;

7-(4-chlorobenzyloxy)-1-(4-chlorobenzyl)-2,3-dimethyl-1H-pyrrolo[3,2-b]pyridine hydrochloride;

7-(4-chlorobenzyloxy)-1-(2-fluorobenzyl)-2,3-dimethyl-1H-pyrrolo[3,2-b]pyridine hydrochloride;

7-(4-chlorobenzyloxy)-1-ethyl-2,3-dimethyl-1H-pyrrolo[3,2-b]pyridine hydrochloride;

7-(4-chlorobenzyloxy)-1-(4-fluorobenzyl)-2,3-dimethyl-1H-pyrrolo[3,2-b]pyridine hydrochloride;

7-(4-chlorobenzyloxy)-1-(3-methoxybenzyl)-2,3-dimethyl-1H-pyrrolo[3,2-b]pyridine hydrochloride;

7-(4-chlorobenzyloxy)-1-(3-fluorobenzyl)-2,3-dimethyl-1H-pyrrolo[3,2-b]pyridine hydrochloride;

7-(4-chlorobenzyloxy)-1-(4-methoxycarbonylbenzyl)-2,3-dimethyl-1H-pyrrolo[3,2-b]pyridine hydrochloride;

7-(4-chlorobenzyloxy)-1-(3-methylbenzyl)-2,3-dimethyl-1H-pyrrolo[3,2-b]pyridine hydrochloride;

7-(4-chlorobenzyloxy)-1-(4-methylbenzyl)-2,3-dimethyl-1H-pyrrolo[3,2-b]pyridine hydrochloride;

7-(4-chlorobenzyloxy)-1-cyclopropylmethyl-2,3-dimethyl-1H-pyrrolo[3,2-b]pyridine hydrochloride;

1-allyl-7-(benzo[1,3]dioxol-5-ylmethoxy)-2,3-dimethyl-1H-pyrrolo[3,2-b]pyridine hydrochloride;

7-(benzo[1,3]dioxol-5-ylmethoxy)-1-(2-methoxyethyl)-2,3-dimethyl-1H-pyrrolo[3,2-b]pyridine hydrochloride;

7-(benzo[1,3]dioxol-5-ylmethoxy)-1-(1,3-dioxolan-2-ylmethyl)-2,3-dimethyl-1H-pyrrolo[3,2-b]pyridine hydrochloride;

7-(benzo[1,3]dioxol-5-ylmethoxy)-1-(2-fluorobenzyl)-2,3-dimethyl-1H-pyrrolo[3,2-b]pyridine hydrochloride;

7-(benzo[1,3]dioxol-5-ylmethoxy)-1-(4-tert-butylbenzyl)-2,3-dimethyl-1H-pyrrolo[3,2-b]pyridine hydrochloride;

7-(benzo[1,3]dioxol-5-ylmethoxy)-1-methoxycarbonylmethyl-2,3-dimethyl-1H-pyrrolo[3,2-b]pyridine hydrochloride;

7-(benzo[1,3]dioxol-5-ylmethoxy)-1-(3,5-dimethylisoxazol-4-ylmethyl)-2,3-dimethyl-1H-pyrrolo[3,2-b]pyridine hydrochloride;

7-(benzo[1,3]dioxol-5-ylmethoxy)-1-(2-oxazolidinon-5-ylmethyl)-2,3-dimethyl-1H-pyrrolo[3,2-b]pyridine hydrochloride;

7-(benzo[1,3]dioxol-5-ylmethoxy)-1-(2-chlorobenzyl)-2,3-dimethyl-1H-pyrrolo[3,2-b]pyridine hydrochloride;

7-(benzo[1,3]dioxol-5-ylmethoxy)-2,3-dimethyl-1-(4-trifluoromethylbenzyl)-1H-pyrrolo[3,2-b]pyridine hydrochloride;

7-(benzo[1,3]dioxol-5-ylmethoxy)-1-(2-hydroxyethyl)-2,3-dimethyl-1H-pyrrolo[3,2-b]pyridine hydrochloride;

7-(benzo[1,3]dioxol-5-ylmethoxy)-1-methoxymethyl-2,3-dimethyl-1H-pyrrolo[3,2-b]pyridine hydrochloride;

7-(benzo[1,3]dioxol-5-ylmethoxy)-1-(2,5-dimethylbenzyl)-2,3-dimethyl-1H-pyrrolo[3,2-b]pyridine hydrochloride;

7-(benzo[1,3]dioxol-5-ylmethoxy)-1-(4-methoxycarbonylbenzyl)-2,3-dimethyl-1H-pyrrolo[3,2-b]pyridine hydrochloride;

7-(benzo[1,3]dioxol-5-ylmethoxy)-1-(3-methylbut-2-enyl)-2,3-dimethyl-1H-pyrrolo[3,2-b]pyridine hydrochloride;

7-(benzo[1,3]dioxol-5-ylmethoxy)-2,3-dimethyl-1-(3-methylbenzyl)-1H-pyrrolo[3,2-b]pyridine hydrochloride;

7-(benzo[1,3]dioxol-5-ylmethoxy)-1-(4-methylbenzyl)-2,3-dimethyl-1H-pyrrolo[3,2-b]pyridine hydrochloride;

7-(benzo[1,3]dioxol-5-ylmethoxy)-1-benzyl-2,3-dimethyl-1H-pyrrolo[3,2-b]pyridine hydrochloride;

7-(benzo[1,3]dioxol-5-ylmethoxy)-1-(3-fluorobenzyl)-2,3-dimethyl-1H-pyrrolo[3,2-b]pyridine hydrochloride;

7-(benzo[1,3]dioxol-5-ylmethoxy)-1-ethyl-2,3-dimethyl-1H-pyrrolo[3,2-b]pyridine hydrochloride;

7-(benzo[1,3]dioxol-5-ylmethoxy)-1-(4-fluorobenzyl)-2,3-dimethyl-1H-pyrrolo[3,2-b]pyridine hydrochloride;

7-(benzo[1,3]dioxol-5-ylmethoxy)-1-(3-methoxybenzyl)-2,3-dimethyl-1H-pyrrolo[3,2-b]pyridine hydrochloride;

7-(benzo[1,3]dioxol-5-ylmethoxy)-1-isobutyl-2,3-dimethyl-1H-pyrrolo[3,2-b]pyridine hydrochloride;

7-(benzo[1,3]dioxol-5-ylmethoxy)-1-cyclopropylmethyl-2,3-dimethyl-1H-pyrrolo[3,2-b]pyridine hydrochloride;

7-(4-fluorobenzyloxy)-1-(2-methoxyethyl)-2,3-dimethyl-1H-pyrrolo[3,2-b]pyridine;

7-(4-fluorobenzyloxy)-1-(2-methoxyethyl)-2,3-dimethyl-1H-pyrrolo[3,2-b]pyridine methanesulfonate;

7-(4-fluorobenzyloxy)-1-(2-methoxyethyl)-2,3-dimethyl-1H-pyrrolo[3,2-b]pyridine benzenesulfonate;

7-(4-fluorobenzyloxy)-1-(2-methoxyethyl)-2,3-dimethyl-1H-pyrrolo[3,2-b]pyridine p-toluenesulfonate;

7-(4-fluorobenzyloxy)-1-(2-methoxyethyl)-2,3-dimethyl-1H-pyrrolo[3,2-b]pyridine nitrate;

7-(4-fluorobenzyloxy)-1-(2-methoxyethyl)-2,3-dimethyl-1H-pyrrolo[3,2-b]pyridine sulfate;

7-(4-fluorobenzyloxy)-1-(2-methoxyethyl)-2,3-dimethyl-1H-pyrrolo[3,2-b]pyridine maleate;

7-(4-fluorobenzyloxy)-1-(2-methoxyethyl)-2,3-dimethyl-1H-pyrrolo[3,2-b]pyridine phosphate;

7-(4-fluorobenzyloxy)-1-(2-methoxyethyl)-2,3-dimethyl-1H-pyrrolo[3,2-b]pyridine malonate;

7-(4-fluorobenzyloxy)-1-(2-methoxyethyl)-2,3-dimethyl-1H-pyrrolo[3,2-b]pyridine camphosulfonate;

7-(4-fluorobenzyloxy)-1-(2-methoxyethyl)-2,3-dimethyl-1H-pyrrolo[3,2-b]pyridine oxalate;

7-(4-fluorobenzyloxy)-1-(2-methoxyethyl)-2,3-dimethyl-1H-pyrrolo[3,2-b]pyridine hydrobromide;

7-(2,4-dichlorobenzyloxy)-1-methoxymethyl-2,3-dimethyl-1H-pyrrolo[3,2-b]pyridine hydrochloride;

7-(2,4-dichlorobenzyloxy)-2,3-dimethyl-1-(3-methylbut-2-enyl)-1H-pyrrolo[3,2-b]pyridine hydrochloride;

1-benzyl-7-(2,4-dichlorobenzyloxy)-2,3-dimethyl-1H-pyrrolo[3,2-b]pyridine hydrochloride;

7-(2,4-dichlorobenzyloxy)-1-ethyl-2,3-dimethyl-1H-pyrrolo[3,2-b]pyridine hydrochloride;

7-(2,4-dichlorobenzyloxy)-1-methoxycarbonylmethyl-2,3-dimethyl-1H-pyrrolo[3,2-b]pyridine hydrochloride;

1-cyclopropylmethyl-7-(2,4-dichlorobenzyloxy)-2,3-dimethyl-1H-pyrrolo[3,2-b]pyridine hydrochloride;

7-(2,4-dichlorobenzyloxy)-1-(4-fluorobenzyl)-2,3-dimethyl-1H-pyrrolo[3,2-b]pyridine hydrochloride;

7-(2,4-dichlorobenzyloxy)-1-(3-methoxybenzyl)-2,3-dimethyl-1H-pyrrolo[3,2-b]pyridine hydrochloride;

1-(2-chlorobenzyl)-7-(2,4-dichlorobenzyloxy)-2,3-dimethyl-1H-pyrrolo[3,2-b]pyridine hydrochloride;

1-(4-tert-butylbenzyl)-7-(2,4-dichlorobenzyloxy)-2,3-dimethyl-1H-pyrrolo[3,2-b]pyridine hydrochloride;

1-benzyl-2,3-dimethyl-7-(3-methylbenzyloxy)-1H-pyrrolo[3,2-b]pyridine hydrochloride;

1-ethyl-2,3-dimethyl-7-(3-methylbenzyloxy)-1H-pyrrolo[3,2-b]pyridine hydrochloride;

1-(3-fluorobenzyl)-2,3-dimethyl-7-(3-methylbenzyloxy)-1H-pyrrolo[3,2-b]pyridine hydrochloride;

1-(4-chlorobenzyl)-2,3-dimethyl-7-(3-methylbenzyloxy)-1H-pyrrolo[3,2-b]pyridine hydrochloride;

2,3-dimethyl-1-(3-methylbenzyl)-7-(3-methylbenzyloxy)-1H-pyrrolo[3,2-b]pyridine hydrochloride;

2,3-dimethyl-7-(3-methylbenzyloxy)-1-(pyridin-2-ylmethyl)-1H-pyrrolo[3,2-b]pyridine hydrochloride;
1-(2,5-dimethylbenzyl)-2,3-dimethyl-7-(3-methylbenzyloxy)-1H-pyrrolo[3,2-b]pyridine hydrochloride;
1-(4-tert-butylbenzyl)-2,3-dimethyl-7-(3-methylbenzyloxy)-1H-pyrrolo[3,2-b]pyridine hydrochloride;
2,3-dimethyl-7-(3-methylbenzyloxy)-1-(3-methylbut-2-enyl)-1H-pyrrolo[3,2-b]pyridine hydrochloride;
2,3-dimethyl-7-(3-methylbenzyloxy)-1-propyl-1H-pyrrolo[3,2-b]pyridine hydrochloride;
1-cyclopropylmethyl-2,3-dimethyl-7-(3-methylbenzyloxy)-1H-pyrrolo[3,2-b]pyridine hydrochloride;
1-allyl-2,3-dimethyl-7-(3-methylbenzyloxy)-1H-pyrrolo[3,2-b]pyridine hydrochloride;
2,3-dimethyl-1-(4-methylbenzyl)-7-(3-methylbenzyloxy)-1H-pyrrolo[3,2-b]pyridine hydrochloride;
1-(2-methoxyethyl)-2,3-dimethyl-7-(3-methylbenzyloxy)-1H-pyrrolo[3,2-b]pyridine hydrochloride;
1-(4-fluorobenzyl)-2,3-dimethyl-7-(3-methylbenzyloxy)-1H-pyrrolo[3,2-b]pyridine hydrochloride;
1-(3-methoxybenzyl)-2,3-dimethyl-7-(3-methylbenzyloxy)-1H-pyrrolo[3,2-b]pyridine hydrochloride;
1-(3-chlorobenzyl)-7-(2-ethoxybenzyloxy)-2,3-dimethyl-1H-pyrrolo[3,2-b]pyridine hydrochloride;
1-cyclopropylmethyl-7-(2-ethoxybenzyloxy)-2,3-dimethyl-1H-pyrrolo[3,2-b]pyridine hydrochloride;
7-(2-ethoxybenzyloxy)-1-(2-methoxyethyl)-2,3-dimethyl-1H-pyrrolo[3,2-b]pyridine hydrochloride;
1-cyclobutylmethyl-7-(2-ethoxybenzyloxy)-2,3-dimethyl-1H-pyrrolo[3,2-b]pyridine hydrochloride;
1-allyl-7-(2-ethoxybenzyloxy)-2,3-dimethyl-1H-pyrrolo[3,2-b]pyridine hydrochloride;
7-(2-ethoxybenzyloxy)-1-ethyl-2,3-dimethyl-1H-pyrrolo[3,2-b]pyridine hydrochloride;
1-(3,4-dichlorobenzyl)-7-(2-ethoxybenzyloxy)-2,3-dimethyl-1H-pyrrolo[3,2-b]pyridine hydrochloride;
7-(2-ethoxybenzyloxy)-1-(2-methoxybenzyl)-2,3-dimethyl-1H-pyrrolo[3,2-b]pyridine hydrochloride;
1-(2-chlorobenzyl)-7-(2-ethoxybenzyloxy)-2,3-dimethyl-1H-pyrrolo[3,2-b]pyridine hydrochloride;
7-(2-ethoxybenzyloxy)-1-(2-fluorobenzyl)-2,3-dimethyl-1H-pyrrolo[3,2-b]pyridine hydrochloride;
7-(2-ethoxybenzyloxy)-2,3-dimethyl-1-propyl-1H-pyrrolo[3,2-b]pyridine hydrochloride;
7-(2-ethoxybenzyloxy)-1-(4-methoxybenzyl)-2,3-dimethyl-1H-pyrrolo[3,2-b]pyridine hydrochloride;
1-(4-chlorobenzyl)-7-(2-ethoxybenzyloxy)-2,3-dimethyl-1H-pyrrolo[3,2-b]pyridine hydrochloride;
7-(2-ethoxybenzyloxy)-1-(3-methylbenzyl)-2,3-dimethyl-1H-pyrrolo[3,2-b]pyridine hydrochloride;
7-(2-ethoxybenzyloxy)-1-(4-methylbenzyl)-2,3-dimethyl-1H-pyrrolo[3,2-b]pyridine hydrochloride;
7-(2-ethoxybenzyloxy)-1-(4-fluorobenzyl)-2,3-dimethyl-1H-pyrrolo[3,2-b]pyridine hydrochloride;
1-(1,3-dioxolan-2-ylmethyl)-7-(2-ethoxybenzyloxy)-2,3-dimethyl-1H-pyrrolo[3,2-b]pyridine hydrochloride;
7-(2-ethoxybenzyloxy)-1-(3-methoxybenzyl)-2,3-dimethyl-1H-pyrrolo[3,2-b]pyridine hydrochloride;
1-(3-fluorobenzyl)-7-(2-ethoxybenzyloxy)-2,3-dimethyl-1H-pyrrolo[3,2-b]pyridine hydrochloride;
1-cyclobutylmethyl-7-(3,5-difluorobenzyloxy)-2,3-dimethyl-1H-pyrrolo[3,2-b]pyridine hydrochloride;
1-cyclopropylmethyl-7-(3,5-difluorobenzyloxy)-2,3-dimethyl-1H-pyrrolo[3,2-b]pyridine hydrochloride;
7-(3,5-difluorobenzyloxy)-1-(2-methoxyethyl)-2,3-dimethyl-1H-pyrrolo[3,2-b]pyridine hydrochloride;
7-(3,5-difluorobenzyloxy)-2,3-dimethyl-1-propyl-1H-pyrrolo[3,2-b]pyridine hydrochloride;
1-(4-chlorobenzyl)-7-(3,5-difluorobenzyloxy)-2,3-dimethyl-1H-pyrrolo[3,2-b]pyridine hydrochloride;
7-(3,5-difluorobenzyloxy)-1-(4-fluorobenzyl)-2,3-dimethyl-1H-pyrrolo[3,2-b]pyridine hydrochloride;
7-(3,5-difluorobenzyloxy)-1-ethyl-2,3-dimethyl-1H-pyrrolo[3,2-b]pyridine hydrochloride;
7-(3,5-difluorobenzyloxy)-1-(3,4-dichlorobenzyl)-2,3-dimethyl-1H-pyrrolo[3,2-b]pyridine hydrochloride;
7-(3,5-difluorobenzyloxy)-1,2,3-trimethyl-1H-pyrrolo[3,2-b]pyridine hydrochloride;
1-(2-chlorobenzyl)-7-(3,5-difluorobenzyloxy)-2,3-dimethyl-1H-pyrrolo[3,2-b]pyridine hydrochloride;
7-(3,5-difluorobenzyloxy)-1-(3,4-dimethoxybenzyl)-2,3-dimethyl-1H-pyrrolo[3,2-b]pyridine hydrochloride;
7-(3,5-difluorobenzyloxy)-1-(2-methoxybenzyl)-2,3-dimethyl-1H-pyrrolo[3,2-b]pyridine hydrochloride;
7-(3,5-difluorobenzyloxy)-1-(2-fluorobenzyl)-2,3-dimethyl-1H-pyrrolo[3,2-b]pyridine hydrochloride;
1-(3-chlorobenzyl)-7-(3,5-difluorobenzyloxy)-2,3-dimethyl-1H-pyrrolo[3,2-b]pyridine hydrochloride;
7-(3,5-difluorobenzyloxy)-1-(4-methoxybenzyl)-2,3-dimethyl-1H-pyrrolo[3,2-b]pyridine hydrochloride;
7-(3,5-difluorobenzyloxy)-1-(3-methoxybenzyl)-2,3-dimethyl-1H-pyrrolo[3,2-b]pyridine hydrochloride;
1-benzyl-7-(3,5-difluorobenzyloxy)-2,3-dimethyl-1H-pyrrolo[3,2-b]pyridine hydrochloride;
7-(3,5-difluorobenzyloxy)-1-(4-methylbenzyl)-2,3-dimethyl-1H-pyrrolo[3,2-b]pyridine hydrochloride;
1-(pyridin-2-ylmethyl)-7-(3,5-difluorobenzyloxy)-2,3-dimethyl-1H-pyrrolo[3,2-b]pyridine hydrochloride;
1-(pyridin-3-ylmethyl)-7-(3,5-difluorobenzyloxy)-2,3-dimethyl-1H-pyrrolo[3,2-b]pyridine hydrochloride;
1-(2,2-dimethylaminoethyl)-7-(3,5-difluorobenzyloxy)-2,3-dimethyl-1H-pyrrolo[3,2-b]pyridine hydrochloride;
2,3-dimethyl-1-(4-methylbenzyl)-7-(4-trifluoromethylbenzyloxy)-1H-pyrrolo[3,2-b]pyridine hydrochloride;
1-(3-methoxybenzyl)-2,3-dimethyl-7-(4-trifluoromethylbenzyloxy)-1H-pyrrolo[3,2-b]pyridine hydrochloride;
1-(2-chlorobenzyl)-2,3-dimethyl-7-(4-trifluoromethylbenzyloxy)-1H-pyrrolo[3,2-b]pyridine hydrochloride;
1-ethyl-2,3-dimethyl-7-(4-trifluoromethylbenzyloxy)-1H-pyrrolo[3,2-b]pyridine hydrochloride;
1-(4-chlorobenzyl)-2,3-dimethyl-7-(4-trifluoromethylbenzyloxy)-1H-pyrrolo[3,2-b]pyridine hydrochloride;
1-cyclopropylmethyl-2,3-dimethyl-7-(4-trifluoromethylbenzyloxy)-1H-pyrrolo[3,2-b]pyridine hydrochloride;
1-(4-methoxybenzyl)-2,3-dimethyl-7-(4-trifluoromethylbenzyloxy)-1H-pyrrolo[3,2-b]pyridine hydrochloride;
1-(3-fluorobenzyl)-2,3-dimethyl-7-(4-trifluoromethylbenzyloxy)-1H-pyrrolo[3,2-b]pyridine hydrochloride;
1-(3,4-dichlorobenzyl)-2,3-dimethyl-7-(4-trifluoromethylbenzyloxy)-1H-pyrrolo[3,2-b]pyridine hydrochloride;
1-benzyl-2,3-dimethyl-7-(pyridin-3-ylmethoxy)-1H-pyrrolo[3,2-b]pyridine hydrochloride;
2,3-dimethyl-1-propyl-7-(pyridin-3-ylmethoxy)-1H-pyrrolo[3,2-b]pyridine hydrochloride;
1-isobutyl-2,3-dimethyl-7-(pyridin-3-ylmethoxy)-1H-pyrrolo[3,2-b]pyridine hydrochloride;
1-allyl-2,3-dimethyl-7-(pyridin-3-ylmethoxy)-1H-pyrrolo[3,2-b]pyridine hydrochloride;
1-(2-methoxyethyl)-2,3-dimethyl-7-(pyridin-3-ylmethoxy)-1H-pyrrolo[3,2-b]pyridine hydrochloride;
1-cyclobutylmethyl-2,3-dimethyl-7-(pyridin-3-ylmethoxy)-1H-pyrrolo[3,2-b]pyridine hydrochloride;

1-benzyl-2,3-dimethyl-7-(pyridin-2-ylmethoxy)-1H-pyrrolo[3,2-b]pyridine hydrochloride;

2,3-dimethyl-1-propyl-7-(pyridin-2-ylmethoxy)-1H-pyrrolo[3,2-b]pyridine hydrochloride;

1-(2-methoxyethyl)-2,3-dimethyl-7-(pyridin-2-ylmethoxy)-1H-pyrrolo[3,2-b]pyridine hydrochloride;

7-(4-bromobenzyloxy)-2,3-dimethyl-1H-pyrrolo[3,2-b]pyridine;

1-benzyl-7-(4-bromobenzyloxy)-2,3-dimethyl-1H-pyrrolo[3,2-b]pyridine hydrochloride;

1-allyl-7-(4-bromobenzyloxy)-2,3-dimethyl-1H-pyrrolo[3,2-b]pyridine hydrochloride;

7-(4-bromobenzyloxy)-1-(4-fluorobenzyl)-2,3-dimethyl-1H-pyrrolo[3,2-b]pyridine hydrochloride;

7-(4-bromobenzyloxy)-1-(3-fluorobenzyl)-2,3-dimethyl-1H-pyrrolo[3,2-b]pyridine hydrochloride;

7-(4-bromobenzyloxy)-2,3-dimethyl-1-(3-methylbenzyl)-1H-pyrrolo[3,2-b]pyridine hydrochloride;

7-(4-bromobenzyloxy)-1-(4-methylbenzyl)-2,3-dimethyl-1H-pyrrolo[3,2-b]pyridine hydrochloride;

7-(4-bromobenzyloxy)-1-(2-fluorobenzyl)-2,3-dimethyl-1H-pyrrolo[3,2-b]pyridine hydrochloride;

7-(4-bromobenzyloxy)-1-(3-chlorobenzyl)-2,3-dimethyl-1H-pyrrolo[3,2-b]pyridine hydrochloride;

7-(4-bromobenzyloxy)-1-cyclobutylmethyl-2,3-dimethyl-1H-pyrrolo[3,2-b]pyridine hydrochloride;

7-(4-bromobenzyloxy)-1-isobutyl-2,3-dimethyl-1H-pyrrolo[3,2-b]pyridine hydrochloride;

7-(4-bromobenzyloxy)-2,3-dimethyl-1-propyl-1H-pyrrolo[3,2-b]pyridine hydrochloride;

7-(4-bromobenzyloxy)-1-(2-methoxybenzyl)-2,3-dimethyl-1H-pyrrolo[3,2-b]pyridine hydrochloride;

1-benzyl-7-(4-isopropylbenzyloxy)-2,3-dimethyl-1H-pyrrolo[3,2-b]pyridine hydrochloride;

1-(4-fluorobenzyl)-7-(4-isopropylbenzyloxy)-2,3-dimethyl-1H-pyrrolo[3,2-b]pyridine hydrochloride;

7-(4-isopropylbenzyloxy)-2,3-dimethyl-1-(3-methylbenzyl)-1H-pyrrolo[3,2-b]pyridine hydrochloride;

1-(3-fluorobenzyl)-7-(4-isopropylbenzyloxy)-2,3-dimethyl-1H-pyrrolo[3,2-b]pyridine hydrochloride;

7-(4-isopropylbenzyloxy)-2,3-dimethyl-1-(4-methylbenzyl)-1H-pyrrolo[3,2-b]pyridine hydrochloride;

7-(4-isopropylbenzyloxy)-1-(2-methoxybenzyl)-2,3-dimethyl-1H-pyrrolo[3,2-b]pyridine hydrochloride;

1-(3-chlorobenzyl)-7-(4-isopropylbenzyloxy)-2,3-dimethyl-1H-pyrrolo[3,2-b]pyridine hydrochloride;

1-(2-fluorobenzyl)-7-(4-isopropylbenzyloxy)-2,3-dimethyl-1H-pyrrolo[3,2-b]pyridine hydrochloride;

1-cyclobutylmethyl-7-(4-isopropylbenzyloxy)-2,3-dimethyl-1H-pyrrolo[3,2-b]pyridine hydrochloride;

7-(4-isopropylbenzyloxy)-1-propyl-2,3-dimethyl-1H-pyrrolo[3,2-b]pyridine hydrochloride;

1-benzyl-7-(4-fluorophenoxy)-2,3-dimethyl-1H-pyrrolo[3,2-b]pyridine hydrochloride;

1-allyl-7-(4-fluorophenoxy)-2,3-dimethyl-1H-pyrrolo[3,2-b]pyridine hydrochloride;

1-cyclobutylmethyl-7-(4-fluorophenoxy)-2,3-dimethyl-1H-pyrrolo[3,2-b]pyridine hydrochloride;

(2,3-dimethyl-1-propyl-1H-pyrrolo[3,2-b]pyridin-7-yl)-(4-fluorobenzyl)carbamic acid tert-butyl ester hydrochloride;

[2,3-dimethyl-1-(2-methoxyethyl)-1H-pyrrolo[3,2-b]pyridin-7-yl]-(4-fluorobenzyl)carbamic acid tert-butyl ester hydrochloride;

(2,3-dimethyl-1-cyclopropylmethyl-1H-pyrrolo[3,2-b]pyridin-7-yl)-(4-fluorobenzyl)carbamic acid tert-butyl ester hydrochloride;

(2,3-dimethyl-1-ethyl-1H-pyrrolo[3,2-b]pyridin-7-yl)-(4-fluorobenzyl)carbamic acid tert-butyl ester hydrochloride;

(1-benzyl-2,3-dimethyl-1H-pyrrolo[3,2-b]pyridin-7-yl)-(4-fluorobenzyl)carbamic acid tert-butyl ester hydrochloride;

[2,3-dimethyl-1-(3-fluorobenzyl)-1H-pyrrolo[3,2-b]pyridin-7-yl]-(4-fluorobenzyl)carbamic acid tert-butyl ester hydrochloride;

[2,3-dimethyl-1-(3-methoxybenzyl)-1H-pyrrolo[3,2-b]pyridin-7-yl]-(4-fluorobenzyl)carbamic acid tert-butyl ester hydrochloride;

[2,3-dimethyl-1-(4-methoxybenzyl)-1H-pyrrolo[3,2-b]pyridin-7-yl]-(4-fluorobenzyl)carbamic acid tert-butyl ester hydrochloride;

[2,3-dimethyl-1-(3-methylbenzyl)-1H-pyrrolo[3,2-b]pyridin-7-yl]-(4-fluorobenzyl)carbamic acid tert-butyl ester hydrochloride;

[2,3-dimethyl-1-(4-methylbenzyl)-1H-pyrrolo[3,2-b]pyridin-7-yl]-(4-fluorobenzyl)carbamic acid tert-butyl ester hydrochloride;

N-(1-allyl-2,3-dimethyl-1H-pyrrolo[3,2-b]pyridin-7-yl)-4-fluorobenzylamine hydrochloride;

N-(1-cyclopropylmethyl-2,3-dimethyl-1H-pyrrolo[3,2-b]pyridin-7-yl)-4-fluorobenzylamine hydrochloride;

N-[1-(2-methoxyethyl)-2,3-dimethyl-1H-pyrrolo[3,2-b]pyridin-7-yl]-4-fluorobenzylamine hydrochloride;

N-[1-(3-methoxybenzyl)-2,3-dimethyl-1H-pyrrolo[3,2-b]pyridin-7-yl]-4-fluorobenzylamine hydrochloride;

N-[1-(4-methoxybenzyl)-2,3-dimethyl-1H-pyrrolo[3,2-b]pyridin-7-yl]-4-fluorobenzylamine hydrochloride;

N-(1-ethyl-2,3-dimethyl-1H-pyrrolo[3,2-b]pyridin-7-yl)-4-fluorobenzylamine hydrochloride;

N-(2,3-dimethyl-1-propyl-1H-pyrrolo[3,2-b]pyridin-7-yl)-4-fluorobenzylamine hydrochloride;

N-(1-benzyl-2,3-dimethyl-1H-pyrrolo[3,2-b]pyridin-7-yl)-4-fluorobenzylamine hydrochloride;

N-[1-(3-fluorobenzyl)-2,3-dimethyl-1H-pyrrolo[3,2-b]pyridin-7-yl]-4-fluorobenzylamine hydrochloride;

N-[1-(4-methylbenzyl)-2,3-dimethyl-1H-pyrrolo[3,2-b]pyridin-7-yl]-4-fluorobenzylamine hydrochloride;

1-benzyl-7-(4-fluorobenzyloxy)-2,3,5,6-tetramethyl-1H-pyrrolo[3,2-b]pyridine hydrochloride;

1-propyl-7-(4-fluorobenzyloxy)-1-(2-methoxyethyl)-2,3,5,6-tetramethyl-1H-pyrrolo[3,2-b]pyridine hydrochloride;

7-(4-fluorobenzyloxy)-2,3,5,6-tetramethyl-1H-pyrrolo[3,2-b]pyridine hydrochloride;

N-(1-allyl-2,3,5,6-tetramethyl-1H-pyrrolo[3,2-b]pyridin-7-yl)-4-fluorobenzylamine hydrochloride;

N-(1-benzyl-2,3,5,6-tetramethyl-1H-pyrrolo[3,2-b]pyridin-7-yl)-4-fluorobenzylamine hydrochloride;

N-(1-cyclopropylmethyl-2,3,5,6-tetramethyl-1H-pyrrolo[3,2-b]pyridin-7-yl)-4-fluorobenzylamine hydrochloride;

N-(1-propyl-2,3,5,6-tetramethyl-1H-pyrrolo[3,2-b]pyridin-7-yl)-4-fluorobenzylamine hydrochloride;

N-[1-(2-methoxyethyl)-2,3,5,6-tetramethyl-1H-pyrrolo[3,2-b]pyridin-7-yl]-4-fluorobenzylamine hydrochloride;

6-bromo-7-(4-fluorobenzyloxy)-2,3-dimethyl-1H-pyrrolo[3,2-b]pyridine;

1-benzyl-6-bromo-7-(4-fluorobenzyloxy)-2,3-dimethyl-1H-pyrrolo[3,2-b]pyridine hydrochloride;

6-bromo-7-(4-fluorobenzyloxy)-1-propyl-2,3-dimethyl-1H-pyrrolo[3,2-b]pyridine hydrochloride;

6-bromo-7-(4-fluorobenzyloxy)-1-(2-methoxyethyl)-2,3-dimethyl-1H-pyrrolo[3,2-b]pyridine hydrochloride;

1-benzyl-7-(4-fluorobenzyloxy)-2,3-dimethyl-1H-pyrrolo[3,2-b]pyridine-6-carbonitrile;

1-benzyl-7-(4-fluorobenzyloxy)-2,3-dimethyl-1H-pyrrolo[3,2-b]pyridine-6-carboxamide;

7-(4-fluorophenyl)-1-(2-methoxyethyl)-2,3-dimethyl-1H-pyrrolo[3,2-b]pyridine hydrochloride;
7-(4-fluorophenyl)-1-cyclopropylmethyl-2,3-dimethyl-1H-pyrrolo[3,2-b]pyridine hydrochloride;
7-(4-fluorophenyl)-1-(3-fluorobenzyl)-2,3-dimethyl-1H-pyrrolo[3,2-b]pyridine hydrochloride;
1-ethyl-7-(4-fluorophenyl)-2,3-dimethyl-1H-pyrrolo[3,2-b]pyridine hydrochloride;
7-(4-fluorophenyl)-1-propyl-2,3-dimethyl-1H-pyrrolo[3,2-b]pyridine hydrochloride;
7-(4-fluorophenyl)-1-(3-methoxybenzyl)-2,3-dimethyl-1H-pyrrolo[3,2-b]pyridine hydrochloride;
7-(4-fluorophenyl)-1-(4-methylbenzyl)-2,3-dimethyl-1H-pyrrolo[3,2-b]pyridine hydrochloride;
7-(4-fluorophenyl)-1-(4-fluorobenzyl)-2,3-dimethyl-1H-pyrrolo[3,2-b]pyridine hydrochloride;
1-allyl-7-(4-fluorophenyl)-2,3-dimethyl-1H-pyrrolo[3,2-b]pyridine hydrochloride;
1-(3-chlorobenzyl)-7-(4-fluorophenyl)-2,3-dimethyl-1H-pyrrolo[3,2-b]pyridine hydrochloride;
1-benzyl-7-(4-fluorobenzyloxy)-2,3-dimethyl-1H-pyrrolo[3,2-b]pyridine-6-carboxylic acid; and
1-benzyl-7-(4-fluorobenzyloxy)-2,3-dimethyl-N-cyclopropyl-1H-pyrrolo[3,2-b]pyridine-6-carboxamide.

4. A process for preparing a compound of formula (I) or a pharmaceutically acceptable salt thereof, which comprises:
reacting a compound of formula (II) with $R_5$—H to obtain a compound of formula (III),
reacting the compound of formula (III) with a compound of formula (IV) to obtain a compound of formula (Ia), and
reacting the compound of formula (Ia) with $R_1$—X to obtain a compound of formula (I):

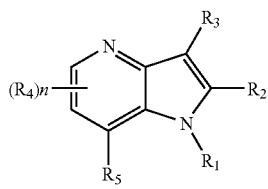
(I)

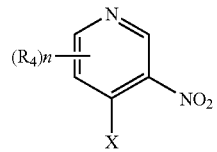
(II)

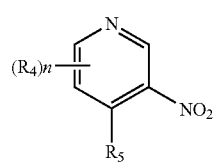
(III)

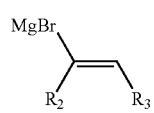
(IV)

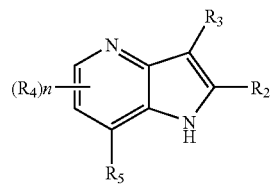
(Ia)

wherein, $R_1$, $R_2$, $R_3$, $R_4$, $R_5$, and n are the same as defined in claim 1 and X is halogen.

5. A pharmaceutical composition comprising a therapeutically effective amount of any of the compound of formula (I) or a pharmaceutically acceptable salt thereof according to claim 1 and a pharmaceutically acceptable carrier.

* * * * *

UNITED STATES PATENT AND TRADEMARK OFFICE
CERTIFICATE OF CORRECTION

PATENT NO. : 7,642,269 B2
APPLICATION NO. : 11/574398
DATED : January 5, 2010
INVENTOR(S) : Jae-Gyu Kim et al.

It is certified that error appears in the above-identified patent and that said Letters Patent is hereby corrected as shown below:

Column 72, line 7, delete "$C_1$-$C_3$" and insert -- $C_1$-$C_5$ --.

Signed and Sealed this

Sixteenth Day of March, 2010

David J. Kappos
*Director of the United States Patent and Trademark Office*